US006694976B1

(12) United States Patent
Takaki et al.

(10) Patent No.: US 6,694,976 B1
(45) Date of Patent: Feb. 24, 2004

(54) OSCILLATING AIR PRESSURE GENERATOR, DIAPHRAGM UNIT, AND HIGH-FREQUENCY ARTIFICIAL RESPIRATION APPARATUS USING THE SAME

(75) Inventors: Toshihisa Takaki, Shizuoka (JP); Mikio Yasukawa, Shizuoka (JP); Yasuhito Sugiura, Shizuoka (JP); Katsuyoshi Suzuki, Shizuoka (JP); Masahiro Kamada, Shizuoka (JP); Tomohisa Ohtake, Shizuoka (JP)

(73) Assignee: Suzuki Motor Corporation, Shizuoka (JP)

( * ) Notice: Subject to any disclaimer, the term of this patent is extended or adjusted under 35 U.S.C. 154(b) by 0 days.

(21) Appl. No.: 09/455,725

(22) Filed: Dec. 6, 1999

(30) Foreign Application Priority Data

Dec. 7, 1998 (JP) .......................... 10-347512
Dec. 15, 1998 (JP) .......................... 10-356668
Dec. 17, 1998 (JP) .......................... 10-359300
Dec. 24, 1998 (JP) .......................... 10-366721

(51) Int. Cl.[7] .......................... A61M 16/00; A62B 7/00
(52) U.S. Cl. .......................... 128/204.18; 128/204.21; 128/204.25; 128/205.24; 128/205.19
(58) Field of Search .................. 128/209.18, 204.21, 128/204.25, 205.24, 205.19

(56) References Cited

U.S. PATENT DOCUMENTS 3,913,703 A * 10/1975 Parker .......................... 181/206
4,190,045 A * 2/1980 Bartels .................. 128/205.24
4,930,498 A * 6/1990 Hayek .................... 128/205.26
5,526,805 A * 6/1996 Lutz et al. ............. 128/202.13
5,850,835 A * 12/1998 Takaki et al. .......... 128/204.18
5,988,166 A * 11/1999 Hayek .................... 128/202.12
6,152,135 A * 11/2000 DeVries et al. ........ 128/205.24

FOREIGN PATENT DOCUMENTS

EP          0625659 A1 * 11/1994
JP          2-131774        5/1990

* cited by examiner

*Primary Examiner*—Weilun Lo
*Assistant Examiner*—Darwin P. Erezo
(74) *Attorney, Agent, or Firm*—Greenblum & Bernstein, P.L.C.

(57) ABSTRACT

An artificial respiration apparatus includes a frame having a positive pressure input port, a negative pressure input port, an atmospheric port and an output port. A switching member switches between a first state in which the positive pressure input port is connected to the output port while the negative pressure input port is connected to the atmospheric port, and a second state in which the positive pressure input port is connected to the atmospheric port while the negative pressure input port is connected to the output port. A drive unit successively drives the switching operation of the switching member such that the connection between the negative pressure input port and the atmospheric port slightly precedes the connection between the positive pressure input port and the output port.

25 Claims, 59 Drawing Sheets

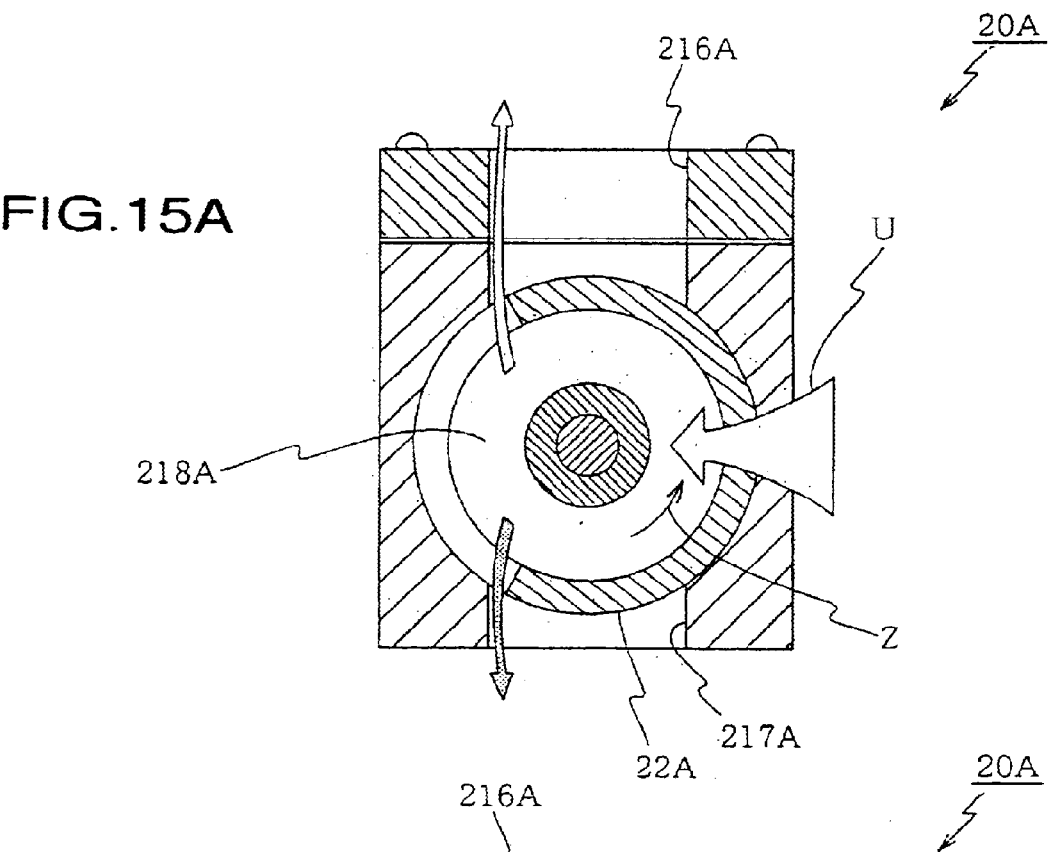
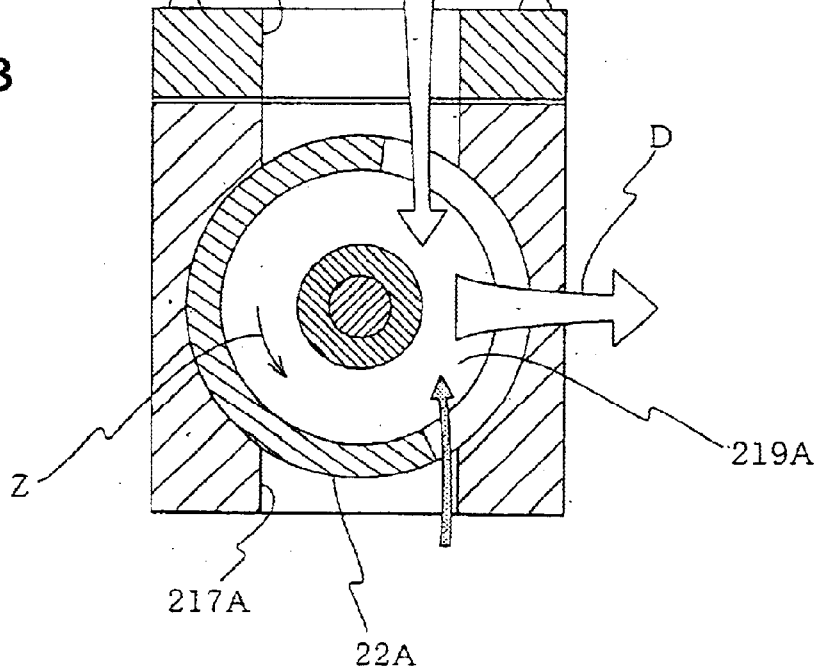

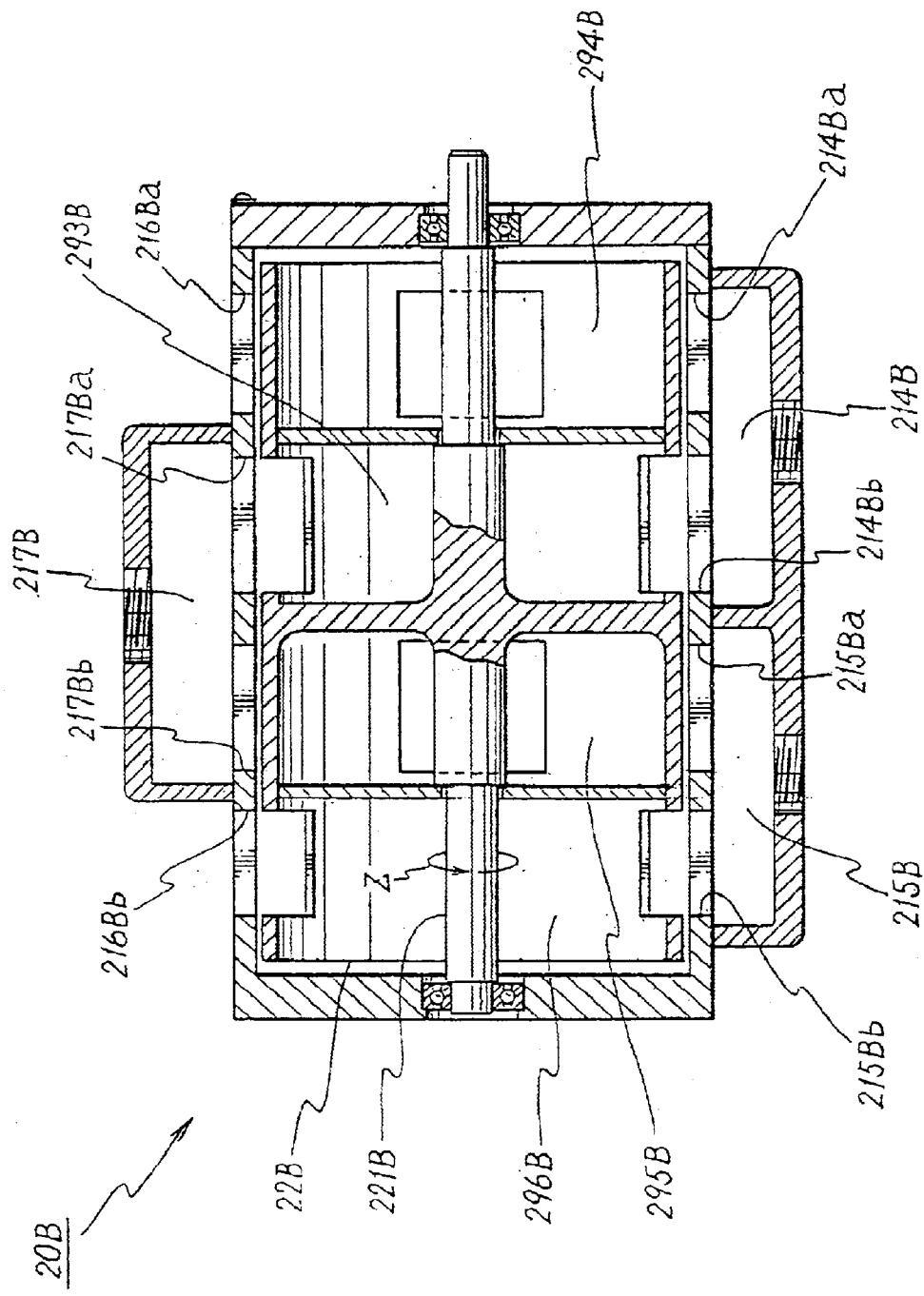

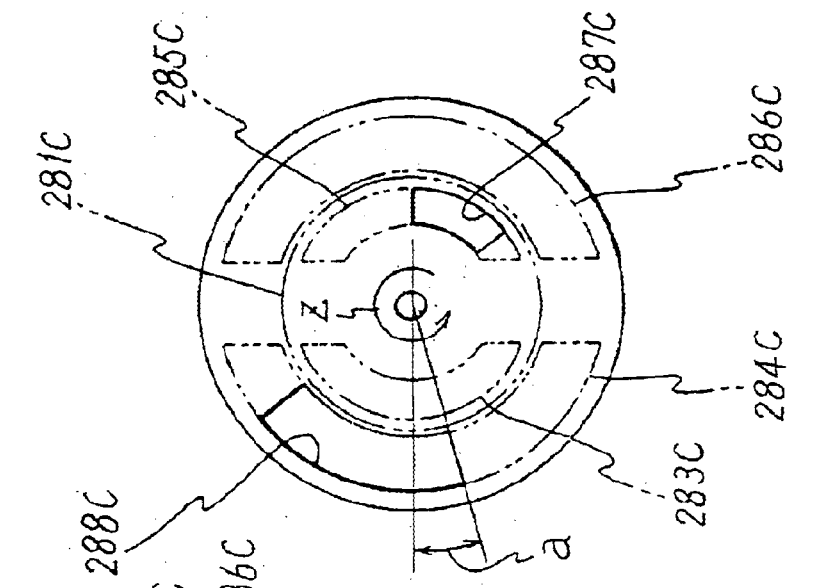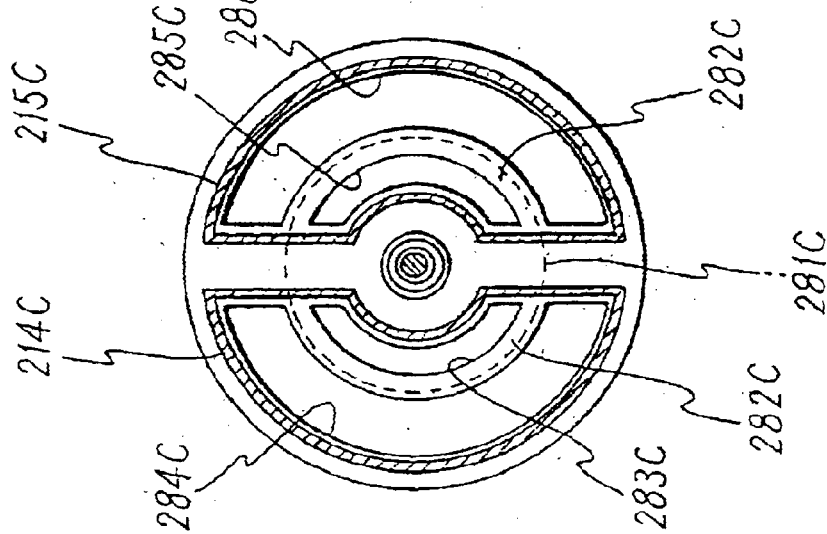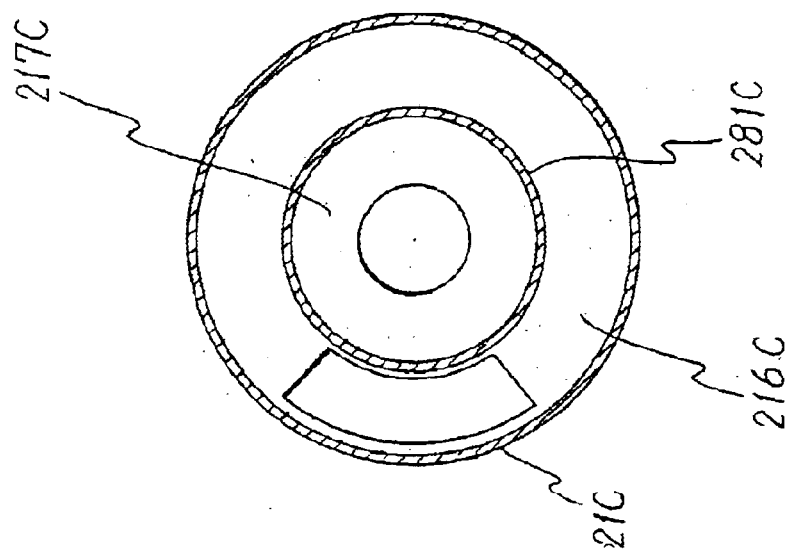

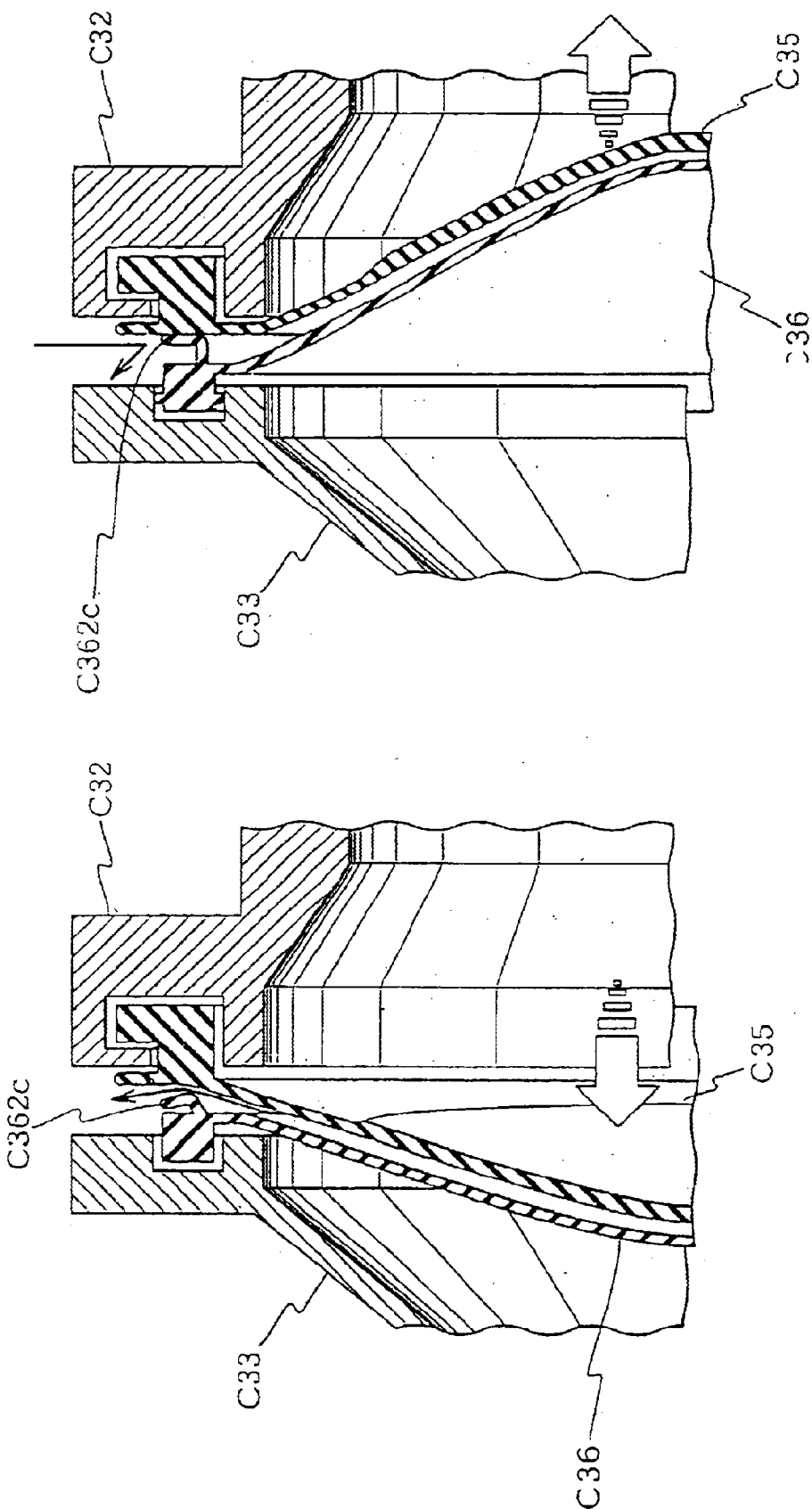

——— : Rotary Valve Discharge Side Open

------- : Rotary Valve Inhale Side Open

OSCILLATING AIR PRESSURE GENERATOR, DIAPHRAGM UNIT, AND HIGH-FREQUENCY ARTIFICIAL RESPIRATION APPARATUS USING THE SAME

BACKGROUND OF THE INVENTION

1. Field of the Invention

The present invention relates to an oscillating air pressure generator, diaphragm unit, and a high-frequency artificial respiration apparatus using the same.

2. Description of the Related Art

As a conventional example, Japanese Patent Publication No. A2-141774 discloses a high-frequency artificial respiration apparatus for performing oxygen inhale for a patient who cannot inhale and exhale by himself/herself. This high-frequency artificial respiration apparatus includes: a blower capable of simultaneously generating a positive pressure air and a negative pressure air; an oscillating air pressure generator connected to the blower and generating an oscillating air pressure; a diaphragm urged by the oscillating air pressure for transmitting the oscillating air pressure to oxygen for inhale; an oxygen supply source; and an exhale pipe path.

FIG. 53 shows an oscillating air pressure generator 100 mounted on the high-frequency artificial respiration apparatus. This oscillating air generator includes a frame 105 having a positive pressure input port 101 urged by a positive pressure from the blower, a negative pressure input port 102 urged by a negative pressure from the blower; an atmospheric port 103 opening into the atmosphere, and an output port 104 for outputting an oscillating air. Moreover, the oscillating air pressure generator 100 has a switching valve member 106 between a first state and a second state. In the first state, the positive pressure input port 101 is connected to the output port 104, and the negative input port 102 is connected to the atmospheric port 103. In the second state, the positive pressure input port 101 is connected to the atmospheric port 103, and the negative input port 102 is connected to the output port. Switching operation of this switching valve member is continuously urged by a drive unit (not depicted).

The switching valve member 106 is a modified-cylindrical body rotatably arranged in the frame. The drive unit urges this modified-cylindrical body to rotate in a predetermined rotation direction. Moreover, in the frame 105, the positive pressure input port 101 faces one and of the switching valve member 106 and the negative pressure input port 102 faces the other end of the switching valve member. The output port 103 and the atmospheric port 104 are arranged to face the outer circumference of the modified-cylindrical body to sandwich the center shaft of the switching valve member 106.

Furthermore, the switching valve member 106 has a first flow path 107 formed at one end of the switching valve member 106 and a second flow path 108 formed on the other end of the switching valve member 106. These flow paths 107 and 108 are arranged at the opposing positions with respect to the center shaft.

FIG. 54(A) is a cross sectional view about the line X—X in FIG. 53, and FIG. 54(B) is a cross sectional view about the line Y—Y in FIG. 53. The arrow Z shows the direction of rotation urged by the drive unit. The switching valve member 106 has cut-off portions at the both ends, forming the first and the second flow paths 107 and 108. Each of the cut-off portions are cut off in the range of 180 degrees from the center axis. As shown in FIG. 54(A) and FIG. 54(B), the cut-off portions are symmetric with respect to a diameter of the end surface of the switching valve member 106.

The output port 103 and the atmospheric port 104 have identical width in the rotation direction Z of the switching valve member 106. Thus, the timing of opening and closing of the ports 103 and 104 by the flow paths 107 and 108 are matched each other.

Referring to FIG. 54 through FIG. 57, explanation will be given on the operation of the oscillating air pressure generator 100. In this oscillating air pressure generator 100, according to rotation of the switching valve member 106, the first and the second flow paths 107 and 108 change their states as shown FIG. 54 through FIG. 47. That is, when the positive pressure input port 101 is connected to the output port 103 in the first flow path 107, the negative pressure input port 102 is connected to the atmospheric port 104 in the second flow path 108. Moreover, when the positive pressure input port 101 is connected to the atmospheric port 104 in the first flow path 107, the negative pressure input port 102 is connected to the atmospheric port 104 in the second flow path 108. These connections are performed alternately.

Thus, an oscillating air pressure is generated from the output port 103 at the periodicity defined by the rpm urged by the drive unit, and the atmosphere is taken in and out from the atmospheric port 104 at the same periodicity.

As a second conventional example, there has been developed a high-frequency artificial respiration apparatus for performing oxygen intake to a patient who cannot breath by himself/herself. This high-frequency artificial respiration apparatus includes: a blower for simultaneously generating a positive pressure and a negative pressure; an oscillating air pressure generator connected to blower, for generating an oscillating air pressure; a diaphragm urged to oscillate by the oscillating air pressure and transmitting the oscillating air pressure to oxygen to be supplied; an oxygen source; and pipe paths for supplying oxygen and exhausting exhaled gas.

FIG. 58 shows an oscillating air pressure generator B100 provided in the aforementioned high-frequency artificial respiration apparatus. This oscillating air pressure generator B100 includes a frame 105 having: a positive pressure input port B101 urged by the positive pressure from the blower; a negative input port B102 urged by negative pressure from the blower; an atmospheric port B103 opened to the atmosphere; and an output port B104 for outputting an oscillating air pressure. Moreover, the oscillating air pressure generator B100 includes a switching valve member B106 for selectively switching between a first connection state and a second connection state. In the first connection state, the positive pressure input port B101 is connected to the output port B104, and the negative pressure input port B102 is connected to the atmospheric port B103. In the second connection state, the positive pressure input port B101 is connected to the atmospheric port B103, and the negative pressure input port B102 is connected to the output port B104. The switching operation of this switching valve member 106 is continuously urged by a drive unit (not depicted).

The switching valve member B106 is a valve rotatably mounted in the frame B105. This valve by its rotation can switch between the aforementioned connection states, i.e., the first connection state (FIG. 58 (A)) and the second connection state (FIG. 58 (B)). These connection states are changed from one to the other repeatedly. Thus, the output port B103 outputs an oscillating air pressure at a periodicity identical to the rpm urged by the drive unit while the atmospheric port B104 performs take-in and take-out of the atmosphere at the same periodicity.

Furthermore, in the aforementioned oscillating air pressure generator B100, the output port B104 is connected to the diaphragm and accordingly, not so much noise is caused. However, the atmospheric port B103 is opened to the atmosphere and causes much noise. To cope with this, a silencer 110 is provided in the atmospheric port B103 (see FIG. 59).

The current high-frequency artificial respiration apparatus has a need of improvement in the ventilation amount of the oxygen for the patient and gas from the patient. In order to increase this ventilation amount, it has been confirmed medically that it is advantageous to increase the amplitude pressure of the oscillating air pressure generated by the oscillating air pressure generator.

In the aforementioned first conventional example, the connection of the positive pressure input port 101 with the output port 103 is performed completely simultaneously with the connection of the negative pressure input port 102 with the atmospheric port 104. Accordingly, supply of atmosphere to the blower via the atmospheric port and the negative pressure input port is performed simultaneously with output of the positive pressure air from the output port via the blower and the positive pressure input port. Here, the atmosphere taken in from the atmospheric port takes a certain time until it is finally exhausted from the output port. That is, even if the output port is connected to the blower, the atmosphere cannot reach there so quickly. That is, it is impossible to obtain a sufficient positive pressure gas. Accordingly, in the conventional oscillating air pressure generator cannot effectively convert the positive pressure supplied from the blower, into the oscillating air pressure. And the oscillation amplitude is also too small.

To cope with this, it can be considered to increase the amplitude pressure by using a blower of a greater size. However, this brings about increase of the power consumption and increase of the size and cost of the entire artificial respiration apparatus, which is not desirable.

Moreover, the aforementioned second conventional example has only one atmospheric port B103 through which excess positive pressure air is exhausted and the atmosphere is taken in. Accordingly, only one silencer B110 has been provided.

On the other hand, the noise caused by the excess positive pressure air and the noise caused by take-in of the atmosphere have different frequency characteristics (sound pressure levels for the respective frequency) and the single silencer cannot work for the two different frequency characteristics. That is, it has been impossible to sufficiently reduce the noise.

Moreover, the positive pressure air supplied from the blower has been compressed and normally has a high temperature. As has been mentioned above, when the atmospheric port B103 is commonly used as has been described above, the a portion of positive pressure air remains in the atmospheric port B103 and in the silencer are returned to the bower, which may decrease the service life of the blower.

Moreover, the diaphragm film mounted on the diaphragm unit has the oscillating portion of a uniform thickness. The diaphragm film is preferably oscillated in the vertical direction of the film with a leading head at its center portion. However, when the film thickness is uniform, there is a case that the film surface constitutes a wave instead of reciprocal movement of the entire film. In this state, the oscillating air pressure cannot be transmitted effectively to the oxygen. That is, ventilation between the oxygen and the exhaled gas cannot be performed effectively for the lungs of a patient.

Furthermore, in the aforementioned diaphragm unit, back flow of exhaled gas may be caused. And for hygiene, the entire diaphragm unit is washed each time it is used. The diaphragm unit having the diaphragm film is separated from the blower, so as to wash the entire diaphragm unit including the diaphragm film. Furthermore, care should also be taken for the blower, i.e., the connection portion with the diaphragm unit, so that no dusts come into the blower. Thus, the aforementioned diaphragm unit requires a troublesome work.

Moreover, the conventional high-frequency artificial respiration apparatus generates an oscillating air pressure by alternately selecting the positive and the negative pressures from the blower. In this case, during the output of the positive pressure, the negative pressure output is opened to the atmosphere to take in the atmosphere. That is, these two operations are simultaneously performed. Accordingly, the atmosphere taken in needs time to reach the output as a positive pressure. That is, it is impossible to obtain a sufficiently high positive pressure, disabling to obtain effective ventilation between oxygen and exhaled gas for lungs of a patient.

Furthermore, in the oscillating air pressure generator, during a negative pressure output, the positive pressure output side is open to the atmosphere. And this oscillating air pressure generator has only one atmospheric port for exhausting the positive output and for taking in the atmosphere. Accordingly, a positive pressure air at an increased temperature by compression is taken in to be supplied to the blower, which significantly decreases the service life of the blower.

Moreover, it is desired to reduce the aforementioned two noises, i.e., the noise caused when exhausting the positive pressure by the atmospheric port of the oscillating air pressure generator and the noise caused by take-in of the atmosphere.

Moreover, it has been desired to reduce the noise caused when the atmospheric air is exhausted and the noise caused when the atmospheric air is taken in.

SUMMARY OF THE INVENTION

It is therefore an object of the present invention to provide an oscillating air pressure generator and a diaphragm unit capable of reducing the power consumption and costs as well as reducing their size and to provide a high-frequency artificial respiration apparatus using such oscillating air pressure generator and diaphragm unit.

The present invention provides an oscillating air pressure generator connected to an air pressure supplier for simultaneously generating a positive pressure and a negative pressure, said oscillating air pressure generator alternately selecting the positive pressure or the negative pressure for output for generating an oscillating air pressure and comprising:

a frame including a positive pressure input port urged by the positive pressure from the air pressure supplier, a negative pressure input port urged by the negative pressure from the air pressure supplier, an atmospheric port open to the atmosphere, and an output port for outputting the oscillating air pressure;

a switching member for selectively switching between a connection state where the positive pressure input port is connected to the output port while the negative pressure input port is connected to the atmospheric port and a connection state where the positive pressure input port is connected to the atmospheric port while the negative pressure input port is connected to the output port; and a drive unit for continuously driving the switching operation of the switching member.

Here, the connection between the positive pressure input port and the output port and the connection between the negative pressure input port and the atmospheric port are performed by the switching member in such a manner that the connection between the negative pressure input port and the atmospheric port slightly precedes the connection between the positive pressure input port and the output port.

In this configuration, the positive pressure input port and the negative pressure input port are connected to the air pressure supplier. The air pressure supplier take in the atmospheric air through its negative pressure generation section and exhausts the atmospheric air through its positive pressure output section. Accordingly, when the atmospheric air is taken in effectively by the negative pressure, the positive pressure can be effectively output.

In the oscillating air pressure generator, when the switching member connects the positive pressure input port with the output port, and the negative pressure input port with the atmospheric port, the atmospheric air is taken in from the atmospheric port and supplied via the negative input port to the air pressure supplier. Moreover, the atmospheric air take in is output as a positive pressure from the output port via the positive pressure input port.

When the switching member has made a connection between the positive pressure input port and the atmospheric port and a connection between the negative pressure input port and the output port, a gas is sucked at the output port. Furthermore, the gas taken in is sucked via the negative input port by the air pressure supplier and exhausted via the positive pressure input port and the atmospheric port.

The switching member continuously repeats the aforementioned connection states, and at the output port, suction and exhaust are successively performed, generating an oscillating air pressure.

Here, in the aforementioned invention, when the positive pressure input port is connected to the output port and the negative port is connected to the atmospheric port by the switching member, the connection between the negative pressure input port slightly precedes the connection between the positive pressure input port and the output port, so that the atmospheric air is supplied to the air pressure earlier and the positive pressure gas supplied from the air pressure supplier is output immediately after the output port and the positive pressure input port is connected.

Here, the switching member may be constituted by a cylindrical body rotatably mounted on the frame and driven to rotate in a predetermined direction by the drive unit, wherein the positive pressure port faces one end of the switching member, the negative pressure port faces the other end of the switching member, and the output port and the atmospheric port are arranged on the outer circumference so as to sandwich the center shaft;

a first flow path is arranged from one end of the switching member to its outer circumference, and a second flow path is arranged from the other end of the switching member to its outer circumference;

the second flow path or the atmospheric port is arranged in such a manner that the second flow path has already made connection with the atmospheric port when the first flow path is at a position to start connection with the output path.

Moreover, the switching member may be a body of revolution mounted rotatably on the frame and the drive unit urges the switching member to rotate in a predetermined direction; wherein in the switching member there are formed a third flow path for communication the positive pressure input port with the output port, a fourth flow path for communicating the positive pressure input port with the atmospheric port, a fifth flow path for communicating the negative pressure input port with the output port, and a sixth flow path for communicating the negative input port with the atmospheric port;

when the switching member is at a first rotation angle, the fourth flow path and the fifth flow path are established;

when the switching member is at a second rotation angle, the sixth flow path is established, and when the switching member is at a third rotation angle, the third flow path is established, wherein a difference between the first rotation angle and the second rotation angle is slightly smaller than the difference between the first rotation angle and the third rotation angle.

Moreover, the switching member may be constituted by a rotary disc rotatably mounted on the frame and is driven to rotate in a predetermined direction by the drive unit, one side of the rotary disc is divided into an inner area and an outer area by a cylinder having a smaller diameter than the rotary disc, so that the output port area is arranged in the inner area and the atmospheric port is arranged in the outer area or vice versa, the other side of the rotary disc is divided into two semicircles for serving as the positive pressure input port and the negative pressure input port, two lines passing through the center of the rotary disc defines four areas, from which two sector areas having an angle no greater than 90 degrees are further divided into inner areas and outer areas, and a through hole is provided in one of the inner areas and in an outer area of the other sector, and the through hole facing the atmospheric port has a continuous additional opening at the upstream side of the rotation.

Furthermore, the switching member may be constituted by a rotary disc rotatably mounted on the frame and is driven to rotate in a predetermined direction by the drive unit, one side of the rotary disc is divided into an inner area and an outer area by a cylinder having a smaller diameter than the rotary disc, so that the positive air pressure input port is arranged in the inner area and the the negative pressure input port is arranged in the outer area or vice versa, the other side of the rotary disc is divided into two semicircles for serving as the output port and the atmospheric port, two lines passing through the center of the rotary disc defines four areas, from which two sector areas having an angle no greater than 90 degrees are further divided into inner areas and outer areas, and a through hole is provided in one of the inner areas and in an outer area of the other sector, and the through hole facing the negative pressure input port has a continuous additional opening at the upstream side of the rotation.

Furthermore, two of the atmospheric ports may be provided, one for connection with the positive pressure input port and the other for connection with the negative pressure input port.

Moreover, the present invention provides an oscillating air pressure generator for use in a high-frequency artificial respiration apparatus, the oscillating air pressure generator being connected to an air pressure supplier for simultaneously generating a positive pressure and a negative pressure, and alternately selecting the positive pressure or the negative pressure for output for generating an oscillating air pressure and comprising: a take-in opening for introducing the atmospheric air and an exhaust opening for exhausting an excess positive pressure air, wherein the take-in opening has an inhale silencer based on the frequency characteristic of a noise generated at the take-in opening and the exhaust opening has an exhaust silencer based on the frequency characteristic of a noise generated at the exhaust opening.

That is, the oscillating air pressure generator of the high-frequency artificial respiration apparatus has a take-in opening for taking in the atmospheric air and an exhaust opening for exhausting an excessive positive pressure air and the former has an inhale silencer and the latter has an exhaust silencer. This can separate the position for exhausting an excessive positive pressure air from the position for taking in the atmospheric air. Thus, the excessive positive air will not be introduced into the oscillating air pressure generator of the high-frequency artificial respiration apparatus.

Furthermore, since the exhaust silencer and the inhale silencer are provided separately, it is possible to sufficiently reduce the noise having different frequency characteristics at the exhaust opening and at the take-in opening.

Furthermore, the inhale silencer may include: a sound absorbing path forming a flow path for the atmospheric air; and a resonance chamber having a partition to form a closed space adjacent to the atmospheric air flow path, and a single communication hole provided in this partition for communication between the closed space and the atmospheric air flow path.

Moreover, the inhale silencer may include an air filter having a net filter portion of a cylindrical shape for preventing dusts and a cover portion of a cylindrical shape.

Furthermore, the inhale silencer may have a sound absorbing path having a sufficient length in comparison to its width. In this case, the sound absorbing path is preferably formed in a spiral shape.

Moreover, the exhaust silencer may include: a sound absorbing path surrounded by a sound absorbing material for passing the positive pressure air; and an expansion chamber having a partition to define a closed space and an entrance and an exit formed in this partition for the positive pressure air.

Moreover, the exhaust silencer may include: a partition to form a closed space in the positive pressure air path; and a resonance chamber having a single communication opening provided in the partition for communication between the closed space and the positive pressure air path.

The aforementioned spiral flow path member can reduce the sound pressure level of the entire frequency band.

The aforementioned expansion chamber has been found experimentally to reduce the sound pressure level of almost the entire frequency band.

The aforementioned resonance chamber includes a partition to form a closed space adjacent to the gas flow passage and a single communication hole provided in the partition communicating with the gas flow passage. In the chamber serving as the gas flow passage adjacent to the resonance chamber via the communication hole, a low-frequency noise around 100 Hz is reduced. This has been confirmed experimentally (see FIG. 37(B)).

The aforementioned sound absorbing path is made from a sound absorbing material. When the gas passes through this sound absorbing path, the frequency of 500 Hz or higher can be reduced. This has been experimentally confirmed (see FIG. 37(C)).

These are used in combination according to the noise frequency characteristic, so that the silencer can effectively lower the noise.

Moreover, the high-frequency artificial respiration apparatus according to the present invention comprises: an inhale gas supply unit for supplying oxygen to a patient; an air pressure supplier for simultaneously generating positive pressure air and a negative pressure air; an oscillating air pressure generator for alternately selecting the positive or the negative pressure for output of an oscillating air pressure; a diaphragm unit urged by the oscillating air to apply the oscillating air pressure to the oxygen to be supplied to the patient from the inhale gas supply unit.

The diaphragm unit includes: a hollow container having an input opening for taking in the oscillating air pressure and an output opening for outputting the oscillating air pressure to the oxygen; and an elastic diaphragm film to divide the container into the side of the input opening and the side of the output opening, wherein the diaphragm has a thicker portion at its center portion than the peripheral portion.

Since the diaphragm film has a thicker portion at its center portion, when the diaphragm film, when subjected to the oscillating air pressure, reciprocally moves in a vertical direction to the diaphragm film and accordingly the entire diaphragm film simultaneously moves reciprocally. Thus, the oscillating air pressure is effectively transmitted to the oxygen.

The oscillating air pressure generator includes a frame, a switching member, and a drive unit. The frame includes a positive pressure input port subjected to the positive pressure from the air pressure supplier, a negative pressure input port subjected to the negative pressure from the air pressure supplier, an atmospheric port open to the atmospheric air, and an output port for outputting an oscillating air pressure.

Furthermore, the switching member selectively switches between a connection state where the positive pressure input port is connected to the output port while the negative pressure input port is connected to the atmospheric port and a connection state where the positive pressure input port is connected to the atmospheric port while the negative pressure input port is connected to the output port.

Moreover, the drive unit continuously drives switching operation of the switching member.

Furthermore, when the positive pressure input port is connected to the output port while the negative pressure input port is connected to the atmospheric port by the switching member, the connection between the negative pressure input port and the atmospheric port is made slightly earlier than the connection between the positive pressure input port and the output port.

Thus, the atmospheric air is supplied to the air pressure supplier in advance, and the positive pressure gas supplied from the air pressure supplier is output immediately after the output port is connected to the positive pressure input port. Accordingly, it is possible to maintain a high positive pressure output.

The diaphragm unit has a container which can be divided into a first diaphragm section having an input opening and a second diaphragm section having an output opening. Each of the first and the second diaphragm sections has a match plane which is matched with each other when the first and the second diaphragm sections are connected.

The diaphragm unit also has a holding mechanism for maintaining the connected state and two diaphragm films, at least one of which has a thicker portion at its center portion.

After a use of the high-frequency artificial respiration apparatus, the holding mechanism is released to separate the diaphragm container into the first diaphragm section and the second diaphragm section. Here one of the diaphragm films attached to the first diaphragm section is left as it is, and only the diaphragm of the second diaphragm section is replaced with a new one or washed and sterilized. And only the second diaphragm section is washed.

After the washing, the diaphragm film is set on the second diaphragm section and connected to the first diaphragm section with their match planes matched. The first and the second diaphragm sections are linked and fixed by the holding mechanism.

Since two diaphragm films are used, and the diaphragm film of the first diaphragm section is not in contact with the inhale gas, it does not require washing or sterilization. When the second diaphragm section is disconnected, the diaphragm of the first diaphragm section can remain as it is. Accordingly there is no danger of intrusion of dusts or germs into the first diaphragm section.

Accordingly, by washing and sterilizing only the second diaphragm section and its diaphragm film, it is possible to maintain a sufficiently clean state. The first diaphragm section need not be disconnected from the oscillating air pressure generator.

The switching member is constituted by a cylindrical body rotatably mounted on the frame and the drive unit urges the cylindrical body to rotate in a predetermined direction.

Furthermore, the positive pressure input port faces one end of the switching member and the negative pressure input port faces the other end of the switching member.

The output port and the atmospheric port are arranged on the outer circumference of the switching member so as to sandwich the rotary shaft of the switching member.

A first flow path is arranged at a location from one end to the outer circumference of the switching member, and a second flow path is arranged at a location from the other end to the outer circumference of the switching member. The second flow path or the atmospheric port is arranged in the following manner. When the first flow path is to be connected with the output port, the second flow path has been already connected with the atmospheric port and at the upstream position by 20 to 50 degrees.

With the aforementioned configuration, the atmospheric air is taken in earlier by the 20 to 50 degrees prior to the output of the positive air pressure.

Moreover, the atmospheric port of the oscillating air pressure generator consists of a take-in opening for taking in the atmospheric air and an exhaust opening for exhausting an excessive positive pressure air. This prevents introduction of positive pressure air.

Moreover, an inhale silencer is provided at the take-in opening for the frequency characteristic of the noise caused at the take-in opening, and an exhaust silencer is provided at the exhaust opening for the frequency characteristic of the noise caused at the exhaust opening.

Thus, the inhale silencer and the exhaust silencer are employed for reducing the noises of different frequency characteristics and accordingly, the two different noises can be effectively reduced.

Furthermore, the diaphragm unit according to the present invention for transmitting the oscillating air pressure output from the oscillating air pressure generator includes: a hollow container having an input opening for taking in the oscillating air pressure and an output opening for outputting the oscillating air pressure to the oxygen.

The hollow container can be divided into a first diaphragm section having the input opening and a second diaphragm section having the output opening. The first and the second diaphragm sections have match planes facing to each other when the first and the second diaphragm sections are connected. The diaphragm unit includes a holding mechanism for maintaining the aforementioned connected state and two diaphragm films. One of the diaphragm films is attached to the first diaphragm section and the other is attached to the second diaphragm section, so that the diaphragm films are adjacent to each other when the first and the second diaphragm sections are connected.

Here, the diaphragm film of the first diaphragm section may be detachably attached to the match plane. Similarly, the diaphragm film of the second diaphragm section may also be detachably attached to the match plane of the second diaphragm section.

With this configuration, when the first diaphragm section is separated from the second diaphragm section, the diaphragm films are respectively attached to the match planes. Accordingly, there is no danger of unnecessary removal of the diaphragm films. The diaphragm of the second diaphragm section is removed for washing and sterilization.

Moreover, each of the diaphragm films has a flange portion at its periphery and each of the match planes has an insert groove for inserting the diaphragm film. Furthermore, at least one of the diaphragm films may have a tab.

In this case, each of the diaphragm films is mounted on the corresponding match plane by inserting the flange portion into the insert groove, and is separated from the match plane by pulling out the flange portion. When the tab is present, it is possible to pull the tab so as to pull out the flange portion from the insert groove.

Furthermore, one of the diaphragm films may have a protrusion continuously arranged around the periphery to serve as a check valve.

In this case, when the diaphragm films are held adjacent to each other, the end of the protrusion is in contact with the other diaphragm film. Here, the end of the protrusion is slanting outwardly, and the air present in a clearance between the diaphragm films can easily be discharged by further slanting the protrusion. On the contrary, intrusion of the atmospheric air into the clearance is prevented by the protrusion. Thus, the protrusion functions as a one-way valve.

Furthermore, the holding mechanism may include: a first holding frame for holding the first diaphragm section; a second holding frame for holding the second diaphragm section; a linkage body for rotatably linking the holding frames; and a connection urging mechanism for urging the first diaphragm section and the second diaphragm section to each other in a direction for bringing the match planes to be in contact with each other.

In this case, the linkage body is preferably arranged on one of the holding frames and includes: a rotary shaft arranged in the vicinity of one of the holding frames and capable of moving toward the holding frame; and an engagement member rotatably engaged with the rotary shaft. The connection urging mechanism includes: a claw member arranged on one of the holding frames so as to be slidable along the matching plate of the diaphragm section held by the holding frame; an engagement member arranged on the other holding frame, where the claw member is to be engaged; and a lever unit to move the claw member by a user. The claw member has a slanting portion to guide the claw into the engagement member.

In the aforementioned holding mechanism, the connection urging mechanism is released and one of the support frames is rotated with respect to the other support frame so as to separate the first diaphragm section and the second diaphragm section.

Explanation will be given on the engagement by the connection urging mechanism and release of the engagement. For engagement, the support frames holding the first diaphragm section and the second diaphragm section are brought into close positions where the claw member can reach the engagement member. The claw member is moved by the lever unit, so that the engagement member is brought into abutment with the slanting portion of the claw member, which slides along the slanting portion. Thus, the support frame having the engagement member is pulled toward the other support frame. Here, a rotary shaft linking the support frames can move closer to the support frame having the rotary shaft. Thus, the diaphragm films are held between the match planes.

When releasing the engagement, the claw member is moved to slide in the opposite direction, so that the engagement member is moved apart from the support frame having the claw member and apart from the end of the claw member. Accordingly, each of the support frames is in a rotatable state and the support frames are separated from each other.

The present invention has the aforementioned function to attain the aforementioned object.

BRIEF DESCRIPTION OF THE DRAWINGS

FIG. 3 shows flow paths and gas flows according to the rotation angle of a switching valve member of the oscillating air pressure generator.

FIG. 4 is a continuation of FIG. 3 and shows gas flows according to the rotation angle of the switching valve member of the oscillating air pressure generator.

FIG. 5 is a continuation of FIG. 4 and shows gas flows according to the rotation angle of the switching valve member of the oscillating air pressure generator.

FIG. 6 is a continuation of FIG. 5 and shows gas flows according to the rotation angle of the switching valve member of the oscillating air pressure generator.

FIG. 7 is a continuation of FIG. 6 and shows gas flows according to the rotation angle of the switching valve member of the oscillating air pressure generator.

FIG. 8 is a continuation of FIG. 7 and shows gas flows according to the rotation angle of the switching valve member of the oscillating air pressure generator.

FIG. 9 is a continuation of FIG. 8 and shows gas flows according to the rotation angle of the switching valve member of the oscillating air pressure generator.

FIG. 10 is a continuation of FIG. 8 and shows gas flows according to the rotation angle of the switching valve member of the oscillating air pressure generator.

FIG. 13 shows a gas flow according to the rotation angle of the switching valve member of the oscillating air pressure generator having the output port and the atmospheric port of identical width, and a reduced open angle.

FIG. 15 is a continuation of FIG. 14 and shows a gas flow according to the rotation angle of the switching valve member of the oscillating air pressure generator. 15(A) shows a gas flow in the first flow path and FIG. 15(B) shows a gas flow in the second flow path.

FIG. 20 is a cross sectional view about a rotary shaft of another (second) example of the oscillating air pressure generator.

FIG. 21 is a cross sectional view along a plane vertical to the rotary shaft of the second example of the oscillating air pressure generator.

FIG. 23(A) is a cross sectional view about the line L—L in FIG. 22; FIG. 23(B) is a cross sectional view about the line M—M; and FIG. 23(C) shows a rotary disc viewed from the line N—N.

FIG. 41 explains the function of a protrusion from the diaphragm film. FIG. 41(A) shows a state in which the air between the diaphragm films is discharged outside; and FIG. 41(B) shows a state preventing intrusion of the atmospheric air into the clearance between the diaphragms.

FIG. 42 shows a claw member engaged with an engagement member.

FIG. 44 shows flow paths and gas flows according to the rotary angle of the switching member of the oscillating air pressure generator.

FIG. 45 shows flow paths and gas flows following FIG. 44.

FIG. 46 shows flow paths and gas flows following FIG. 45.

FIG. 47 shows flow paths and gas flows following FIG. 46.

FIG. 48 shows flow paths and gas flows following FIG. 47.

FIG. 49 shows flow paths and gas flows following FIG. 48.

FIG. 50 shows flow paths and gas flows following FIG. 49.

FIG. 51 shows flow paths and gas flows following FIG. 50.

FIG. 54 is a cross sectional view showing flow paths and gas flows during operation.

DESCRIPTION OF THE PREFERRED EMBODIMENTS

Embodiment 1

Figure 1:
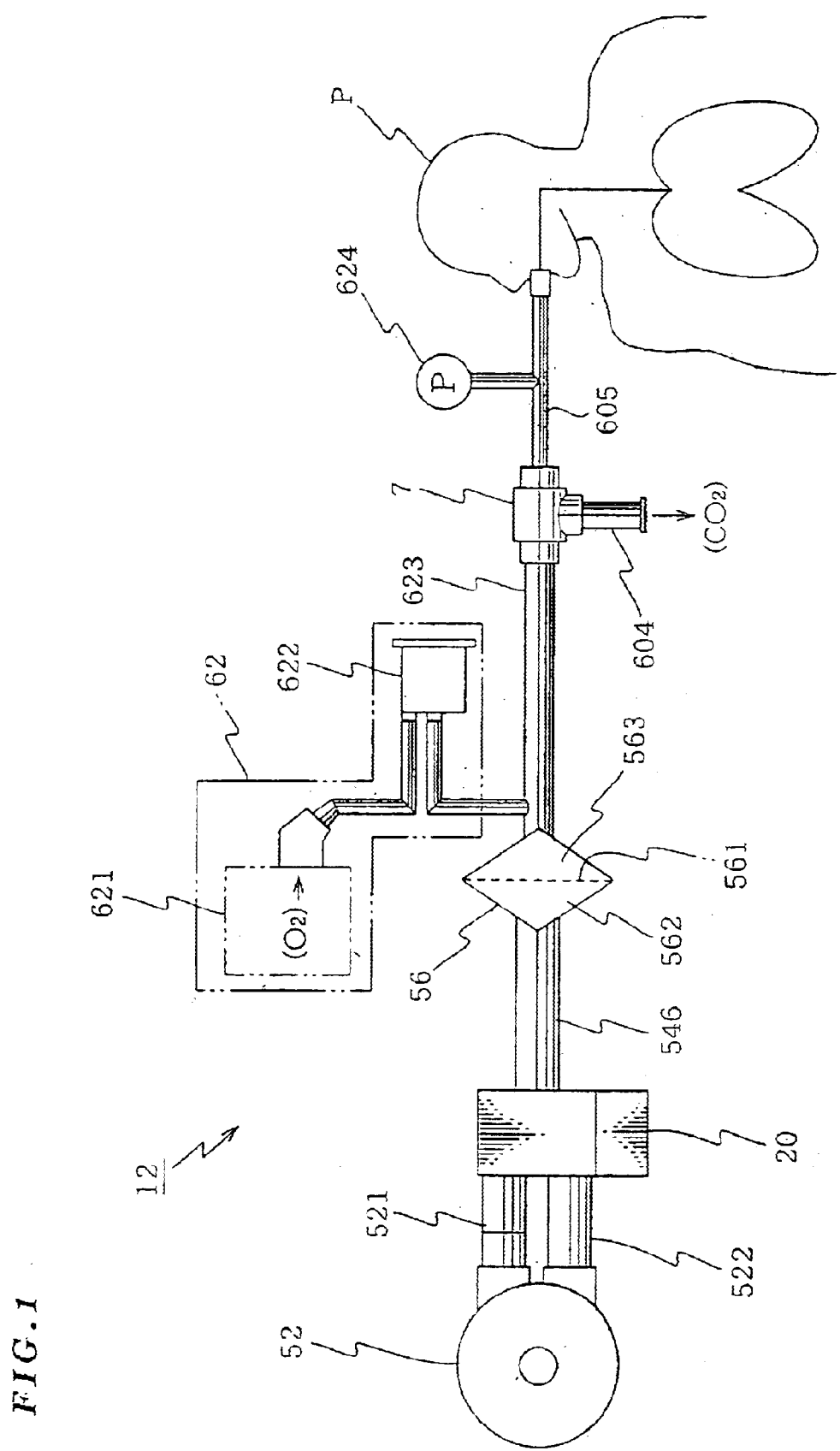
FIG. 1 shows a configuration of an artificial respiration apparatus according to a first embodiment of the present invention.

Description will now be directed to a first embodiment of the present invention with reference to FIG. 1 to FIG. 23. In this embodiment, an oscillating air pressure generator 20 mounted on a high-frequency oscillation (HFO) artificial respiration apparatus which performs oxygen supply and exhaled gas exhaust for a patient P. The artificial respiration apparatus 12 includes: inhale gas supply unit as an oxygen supply source; a blower (air pressure supplier) 52 which generates a positive pressure air and a negative pressure air simultaneously; oscillating air pressure generator 20 which alternately selects the positive pressure and negative pressure so as to be converted into an oscillating air pressure; a diaphragm unit 56 which is urged to operate by the oscillating air pressure from the oscillating air pressure generator 20, so as to urge oxygen (oxygen mixed with air) from the inhale has supply section 62; and pipe paths for supplying oxygen to the patient P and exhausting exhaled gas.

The aforementioned inhale gas supply unit 62 has a blender 621 for mixing oxygen with the atmosphere, and a humidifier 622 for humidifying the air to be sent out from the blender 621. The humidifier 622 is connected to an inhale pipe 623 for supplying the humidified gas to the patient P. The inhale pipe communicates with a pressurized chamber 563 of the diaphragm unit 56 and is connected to an inhale end pipe 605 via a three-way branched pipe 7. A pressure sensor 624 is mounted on the inhale end pipe 605 for detecting an inhale state of the patient P. Moreover, the three-way branched pipe 7 has an exhaust pipe 604 for exhausting the exhaled gas.

The diaphragm unit 56 includes a pressurizing chamber, a pressurized chamber, and a diaphragm 561 made from an expandable member to isolate the pressurizing chamber 561 from the pressurized chamber. The pressurizing chamber is connected via the oscillating air pressure pipe 545 to the oscillating air pressure generator 20.

Furthermore, this oscillating air pressure generator 20 is connected to the blower 52 via a positive pressure pipe 521 and a negative pressure pipe 522. The blower 522 takes in air from the negative pressure pipe 522 and discharges the air through the positive pressure pipe 521.

Figure 2:
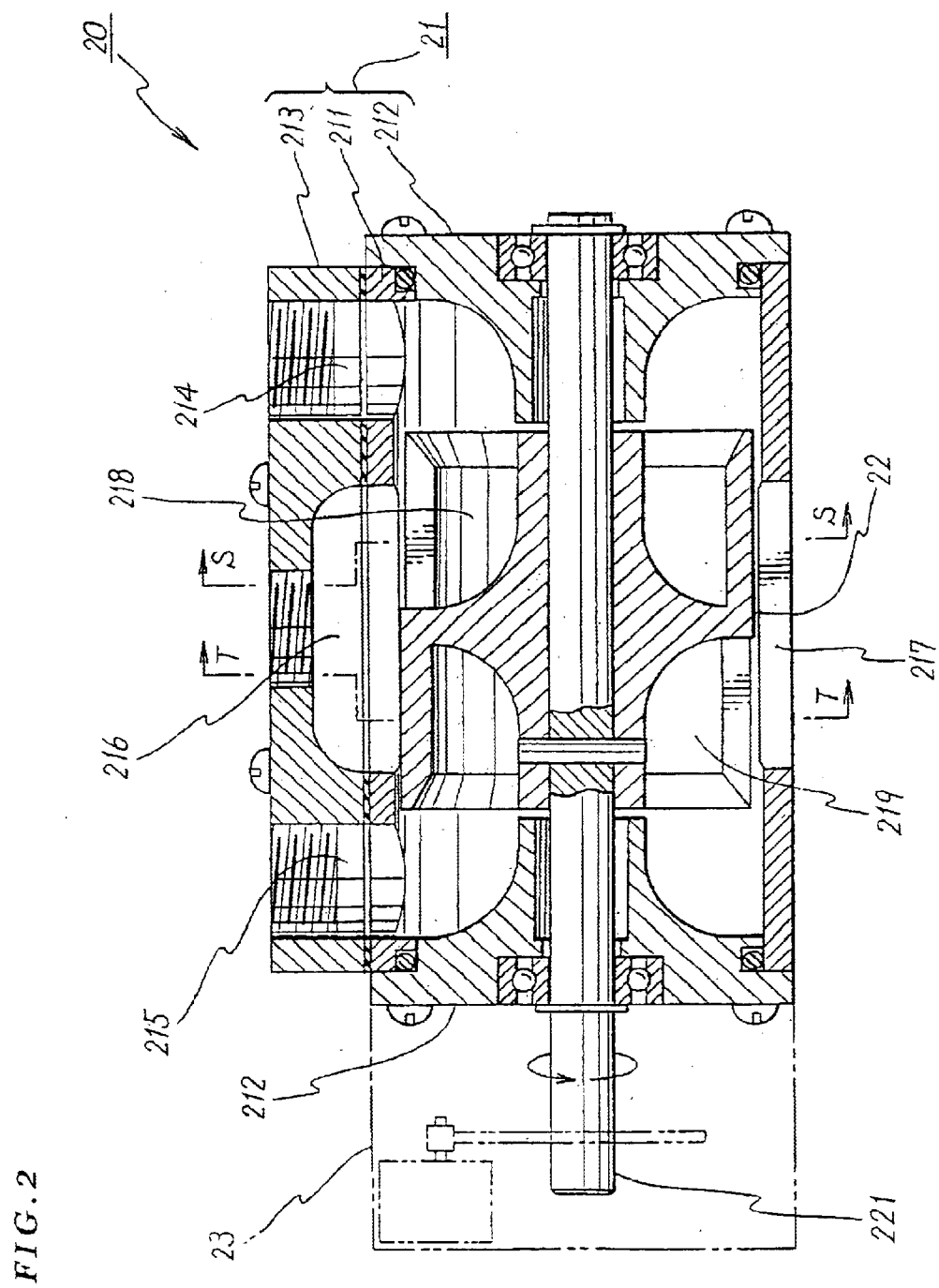
FIG. 2 is a cross sectional view of an oscillating air pressure generator shown in FIG. 1 about the rotation shaft.
Figure 3A:
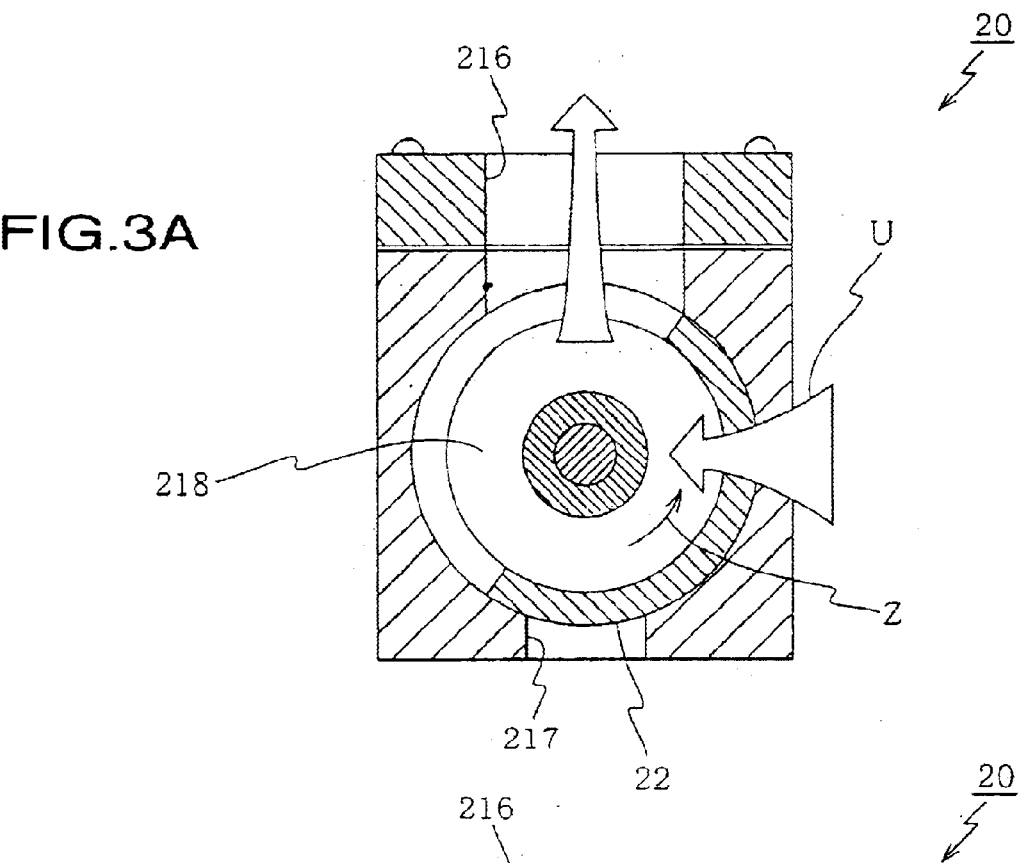
FIG. 3(A) is a cross sectional view about the line S—S in FIG. 2
Figure 3B:
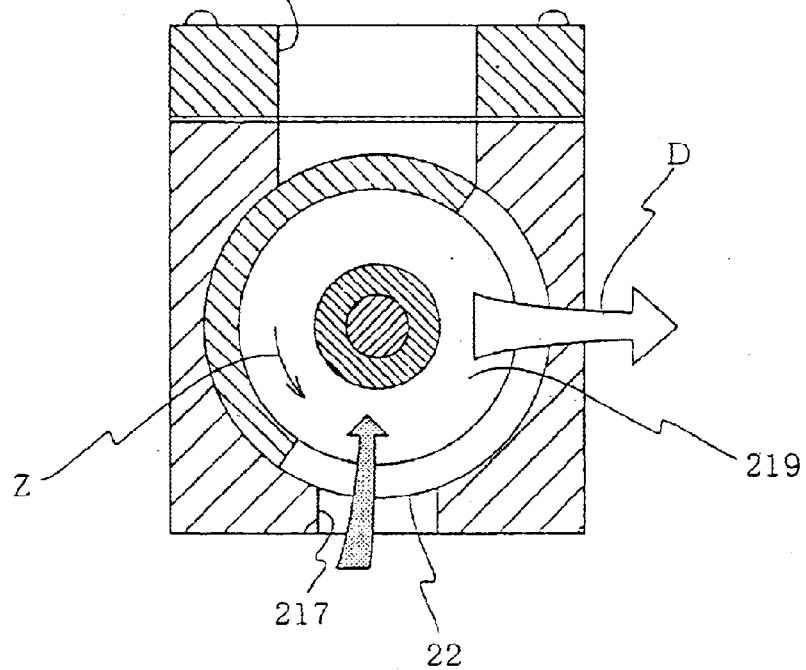
FIG. 3(B) is a cross sectional view about the line T—T in FIG. 2.

Here, explanation will be given on the oscillating air pressure generator 20 with reference to FIG. 2 through FIG. 12. FIG. 2 is a cross sectional view about a rotary shaft of the oscillating air pressure generator 20 which will be detailed later. FIG. 3(A) is a cross sectional view about the line S—S in FIG. 2, and FIG. 3(B) is a cross sectional view about the line T—T in FIG. 2. It should be noted that (A) and (B) show state realized simultaneously.

This oscillating air pressure generator 20 includes: a frame 21 having a predetermined internal void; a cylindrical switching valve member 22 mounted rotatably in the void of the frame 21; and a drive unit for rotating the switching valve member 22.

The frame 21 includes a cylindrical body 21 having an inner diameter slightly greater than the outer diameter of the switching valve member 22; lids 212 to cover the both ends of the cylindrical body 211; and a pipe connector 213 where various ports are formed as will be detailed later. The switching valve member 22 is arranged in the center of the cylindrical body 211 and supported on the rotary shaft 221 mounted via a bearing on the lids.

Furthermore, the frame 21 includes: a positive pressure input port 214 connected to the positive pressure pipe 521; a negative pressure input port 215 connected to the negative pressure pipe 522; an atmospheric port 216 open to the atmosphere; and an output port 217 for outputting an oscillating air pressure to the diaphragm unit 56 via the oscillating air pressure pipe 546.

The positive pressure input port 214 and the negative pressure input port 215 are formed through the wall of the frame 21 in the vicinity of the both ends of the frame 21, and respectively communicate with the both ends of the switching valve member 22. Moreover, the output port 217 and the atmospheric port 216 are formed through the center portion of the cylindrical body 11 and respectively in contact with the outer circumference of the switching valve member 22. Moreover, the output port 217 and the atmospheric port 216 are positioned symmetrically with respect to the rotary shaft 221.

A rotary shaft 221 is inserted into the center of the switching valve member 22 and fixed by a pin so that the switching valve member 22 rotates together with the rotary shaft. The switching valve member 22 has two cut-off portions at both ends and wall of its cylindrical body. Each of the cut-off portions is open by 180 degrees around the rotary shaft 221 and opposes to each other with respect to the rotary shaft 221.

With rotation of the switching valve member 22, each of the cut-off portions selectively faces the output port 217 and the atmospheric port 216. One of the cut-off portions (first cut-off portion) formed from the end surface communicating with the positive pressure input port 214 of the switching valve member 22 forms a first flow path 218 selectively communicating with the positive pressure input port 214 to the output port or to the atmospheric port 216. Similarly, the other cut-off portion (second cut-off portion) formed from the end surface communicating with the negative pressure input port 215 of the switching valve member 22 forms a second flow path 219 selectively communicating from the negative input port 215 to the output port 217 or to the atmospheric port 216.

The switching valve member 22 forming the flow paths 218 and 219 can switch between the first connection state in which the positive pressure input port 214 is connected to the output port 217, and the negative pressure input port 215 is connected to the atmospheric port 216; and the second connection state in which the positive pressure input port 214 is connected to the atmospheric port 216, and the negative pressure input port 215 is connected to the output port 217.

The drive unit 23 is provided at the end of the frame 21 and is engaged with the rotary shaft 221 exposed outside of the frame 21. The drive unit 23 has reduction gears for reducing the rpm to be transmitted to the rotary shaft 221. Since the artificial respiration apparatus 12 requires generation of oscillating air pressure having a frequency of 15 Hz, this drive unit 23 urges the rotation of the rotary shaft 221 at 900 rpm. Moreover, this drive unit 23 rotates the switching valve member 22 constantly in the direction Z as shown in FIG. 3.

Furthermore, in this oscillating air pressure generator 20, as shown in FIG. 3, is characterized in that the width of the atmospheric port 216 in the direction of rotation of the switching valve member is set greater than the width of the output port 17.

Accordingly, when the switching valve member 22 is rotating and the first flow path 218 is at a position to start connection with the output port 217, the second flow path 219 is slightly at upstream side to the position to be connected with the atmospheric port 216. In other words, when the rotation of the switching valve member 22 makes the first flow path 218 communicate with the positive pressure input port 214 and the output port 217 and the second flow path 219 makes the positive input port 214 communicate with the positive pressure input port 214 and the output port 217, the communication between the negative pressure input port 215 and the atmospheric port slightly precedes the communication between the positive pressure input port 214 and the output port.

Figure 4A:
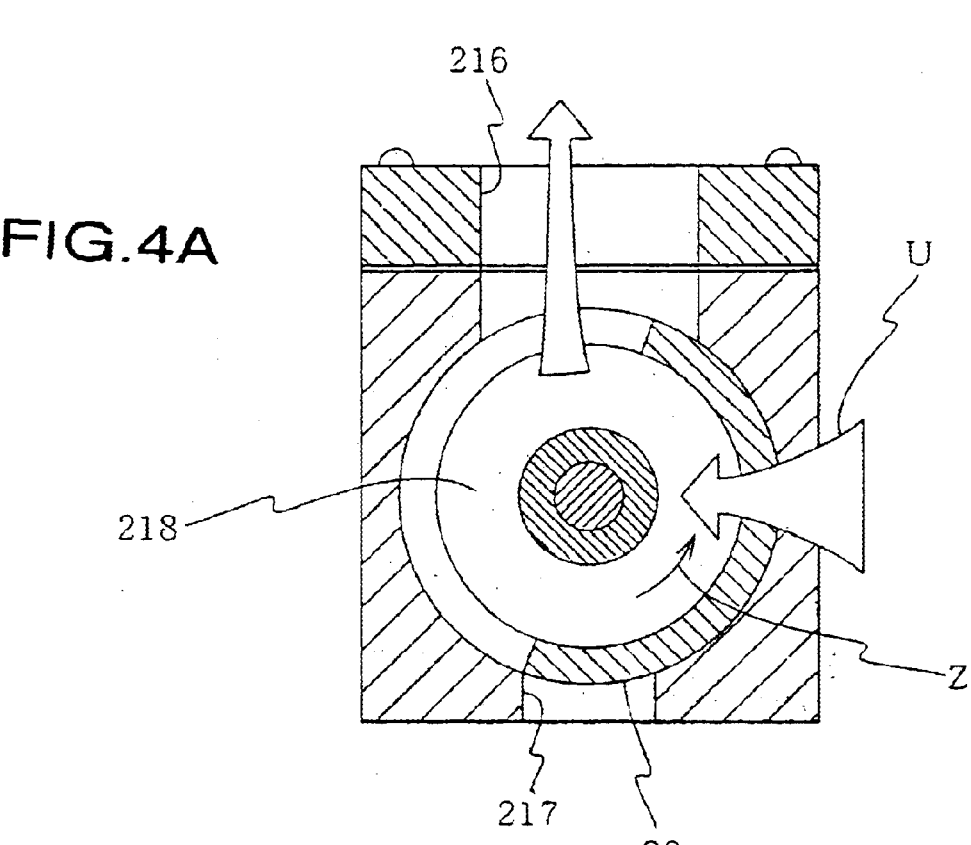
FIG. 4(A) shows a gas flow in a first flow path and FIG. 4(B) shows a gas flow in a second flow path.
Figure 4B:
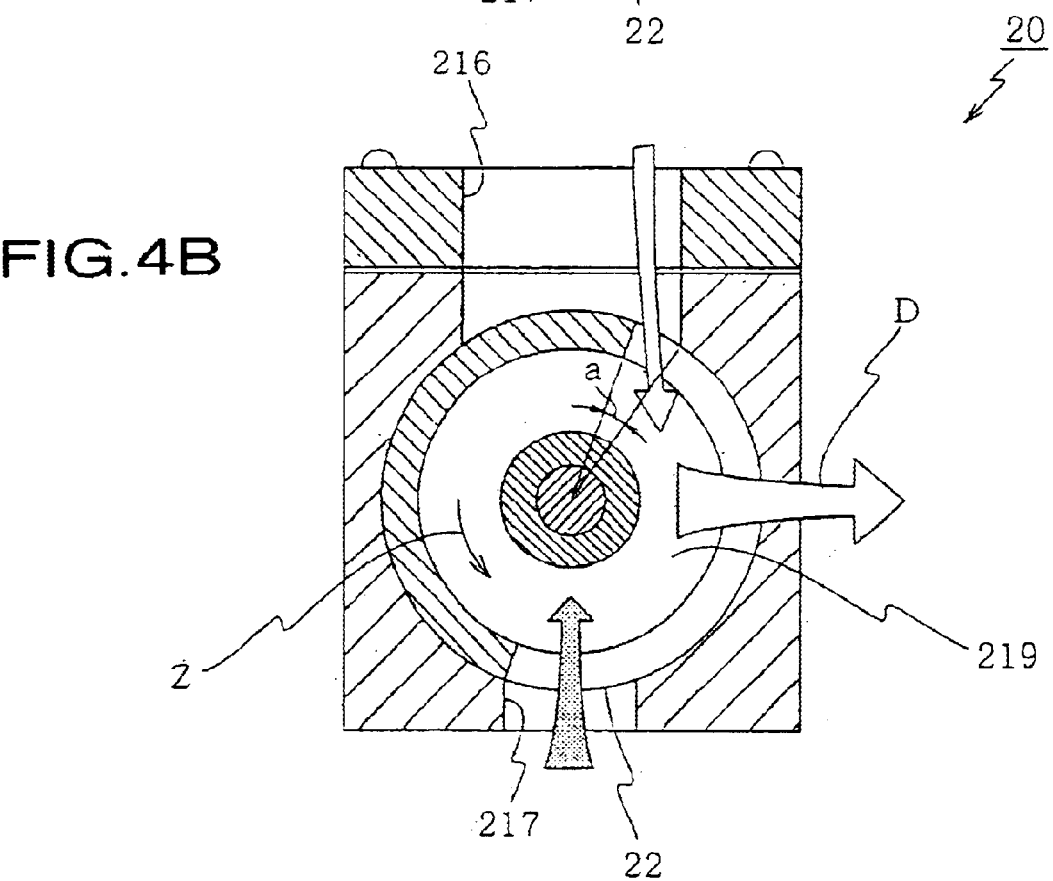
Figure 5A:
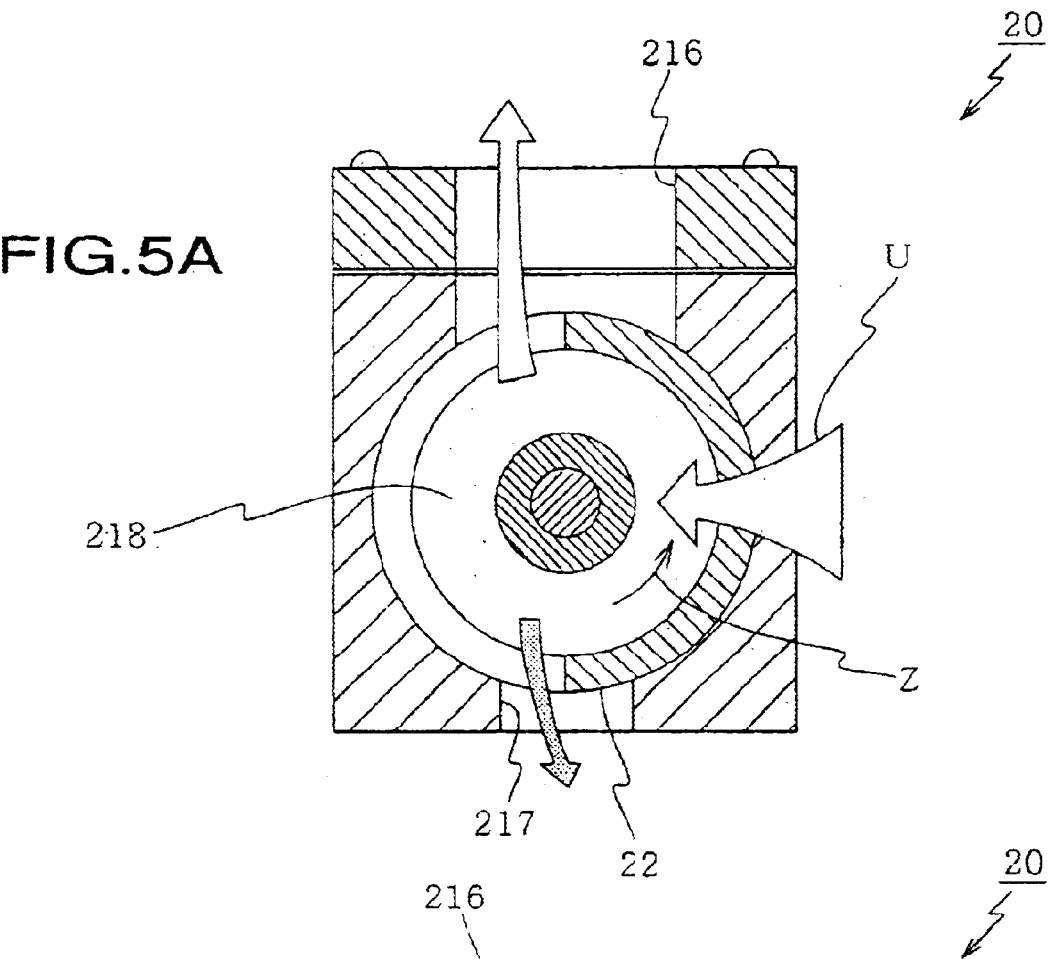
FIG. 5(A) shows a gas flow in the first flow path and FIG. 5(B) shows a gas flow in the second flow path.
Figure 5B:
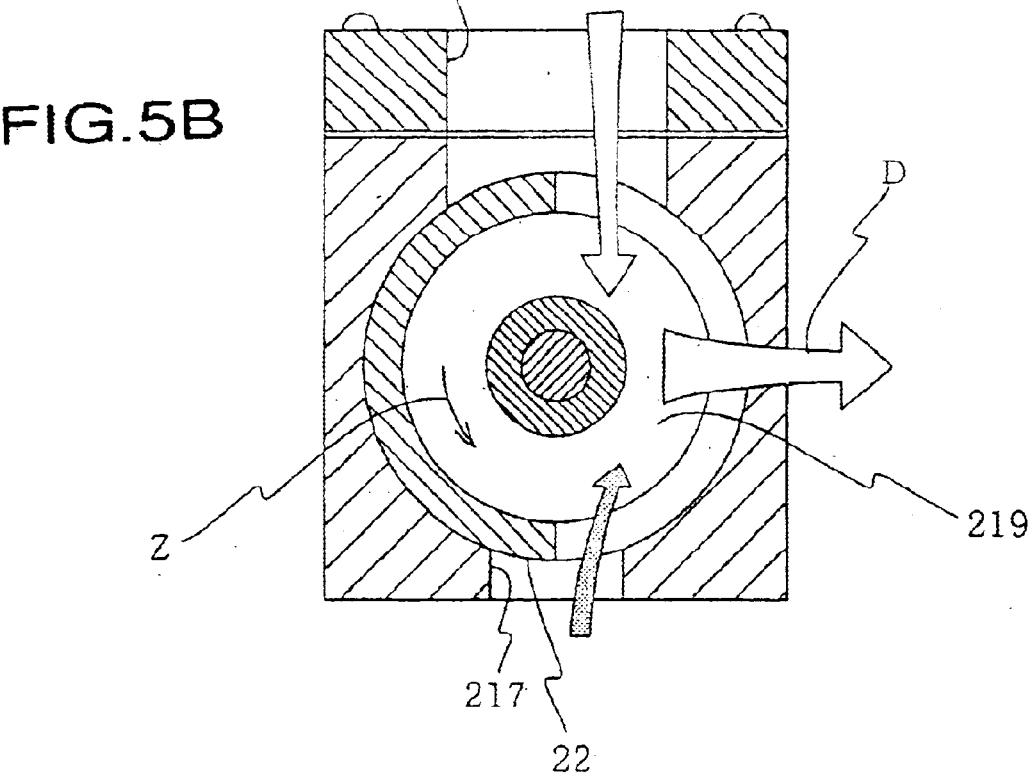
Figure 6A:
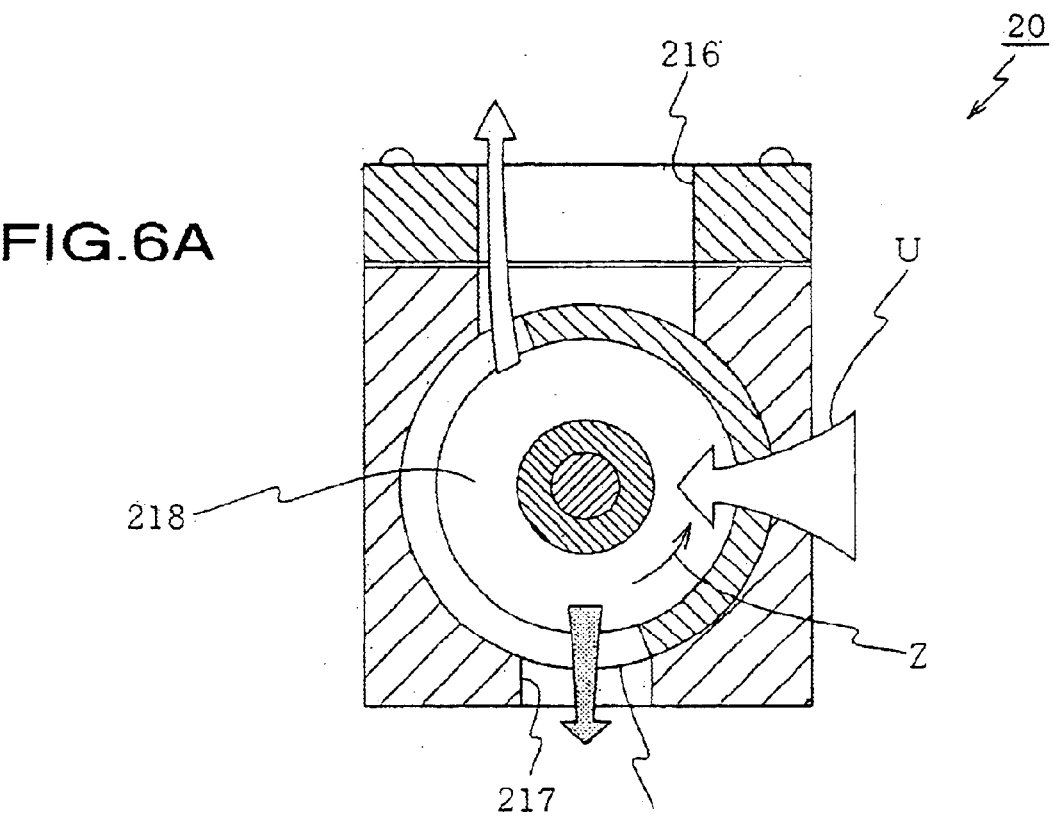
FIG. 6(A) shows a gas flow in the first flow path and FIG. 6(B) shows a gas flow in the second flow path.
Figure 6B:
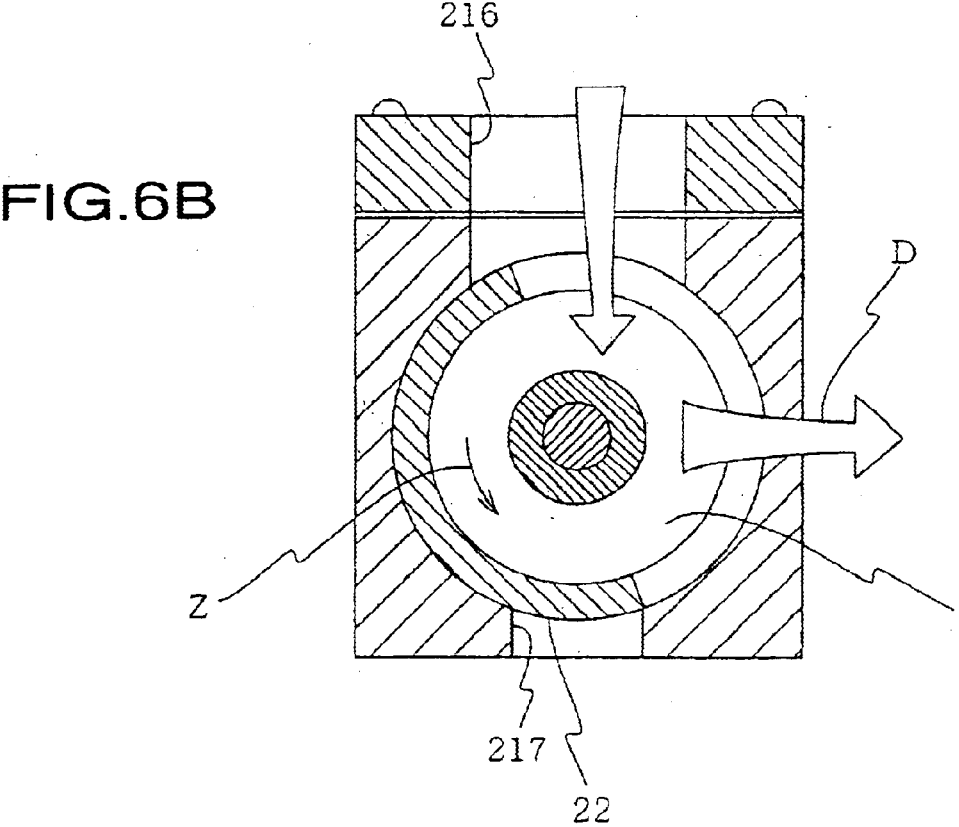
Figure 7A:
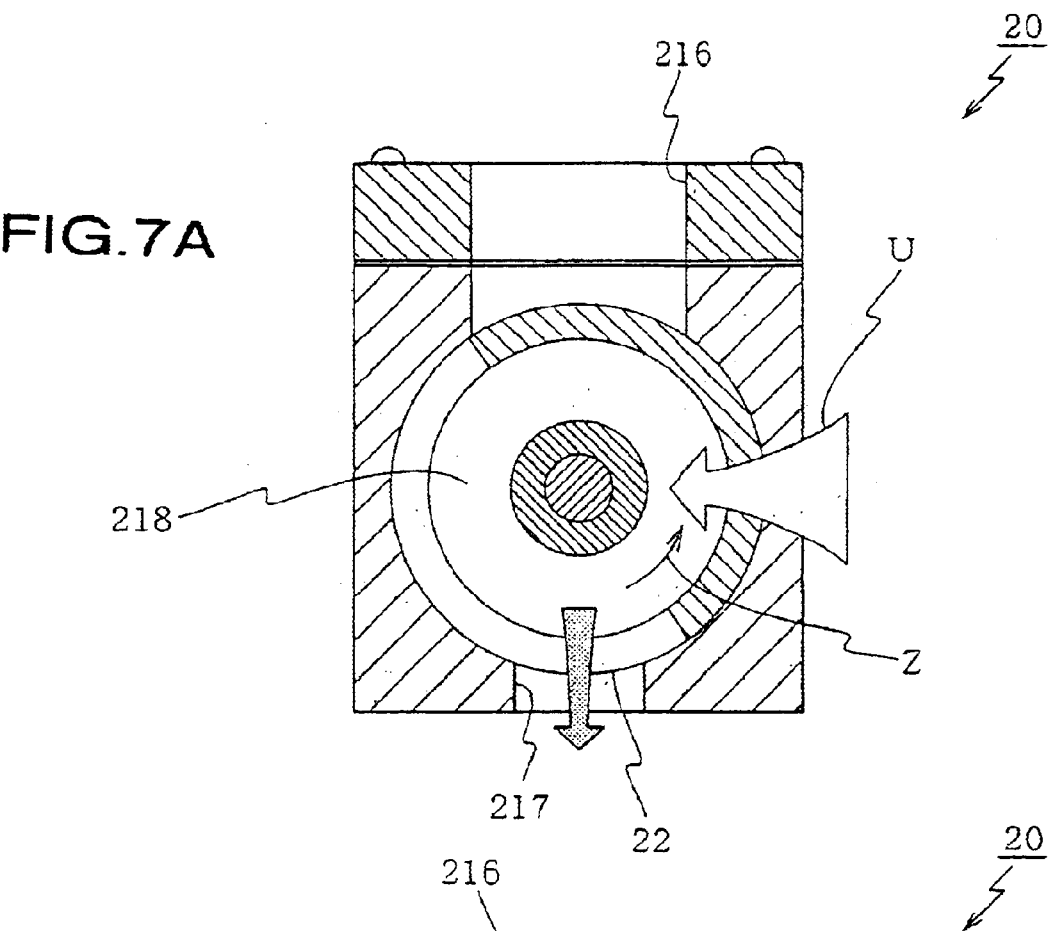
FIG. 7(A) shows a gas flow in the first flow path and FIG. 7(B) shows a gas flow in the second flow path.
Figure 7B:
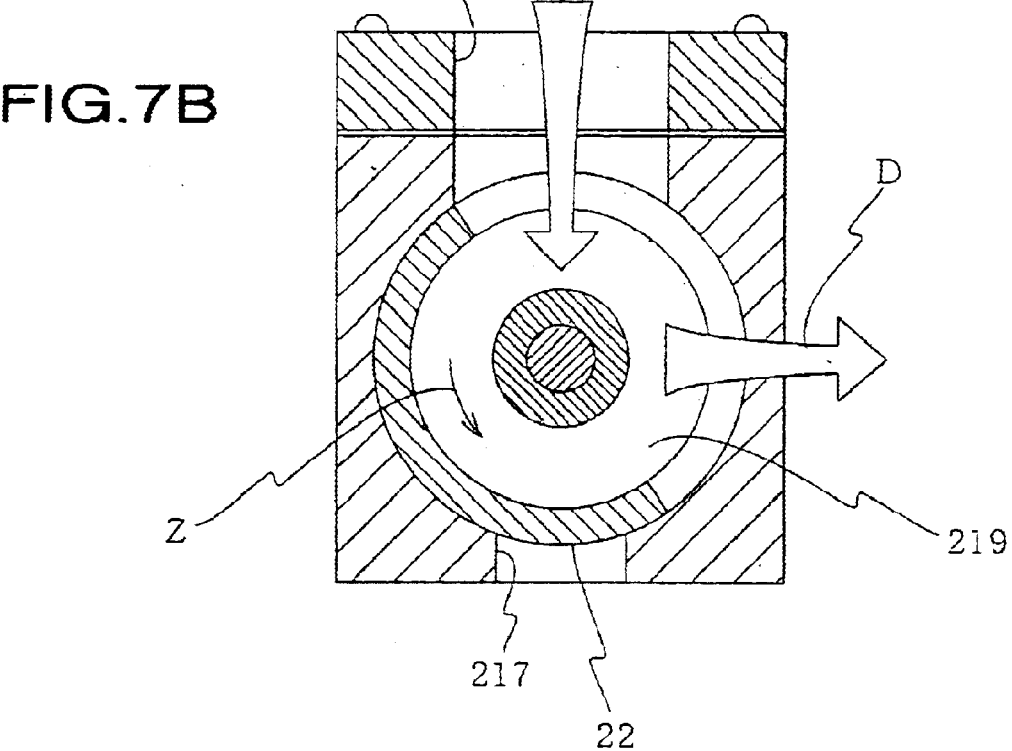
Figure 8A:
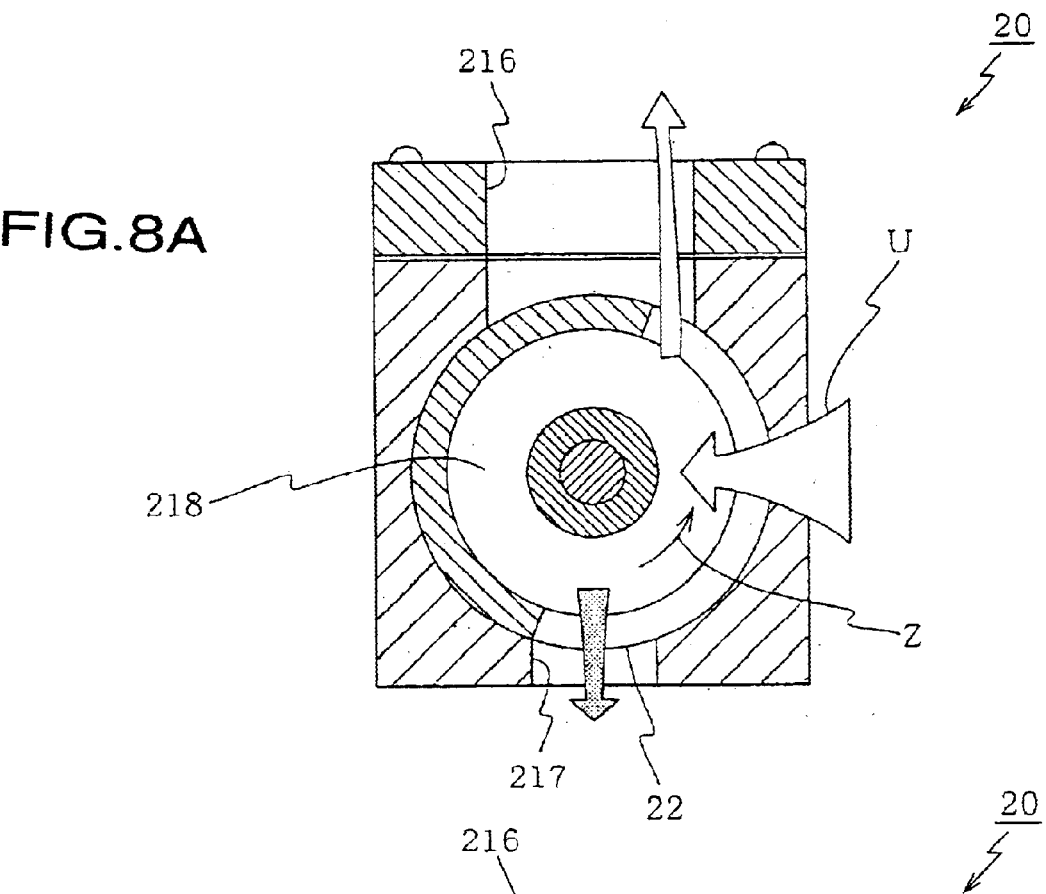
FIG. 8(A) shows a gas flow in the first flow path and FIG. 8(B) shows a gas flow in the second flow path.
Figure 8B:
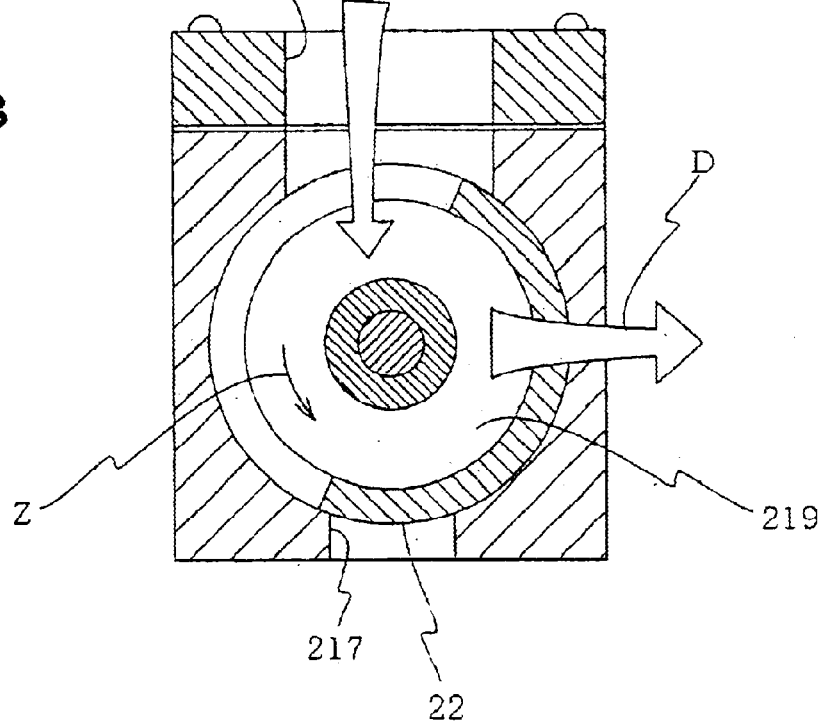
Figure 9A:
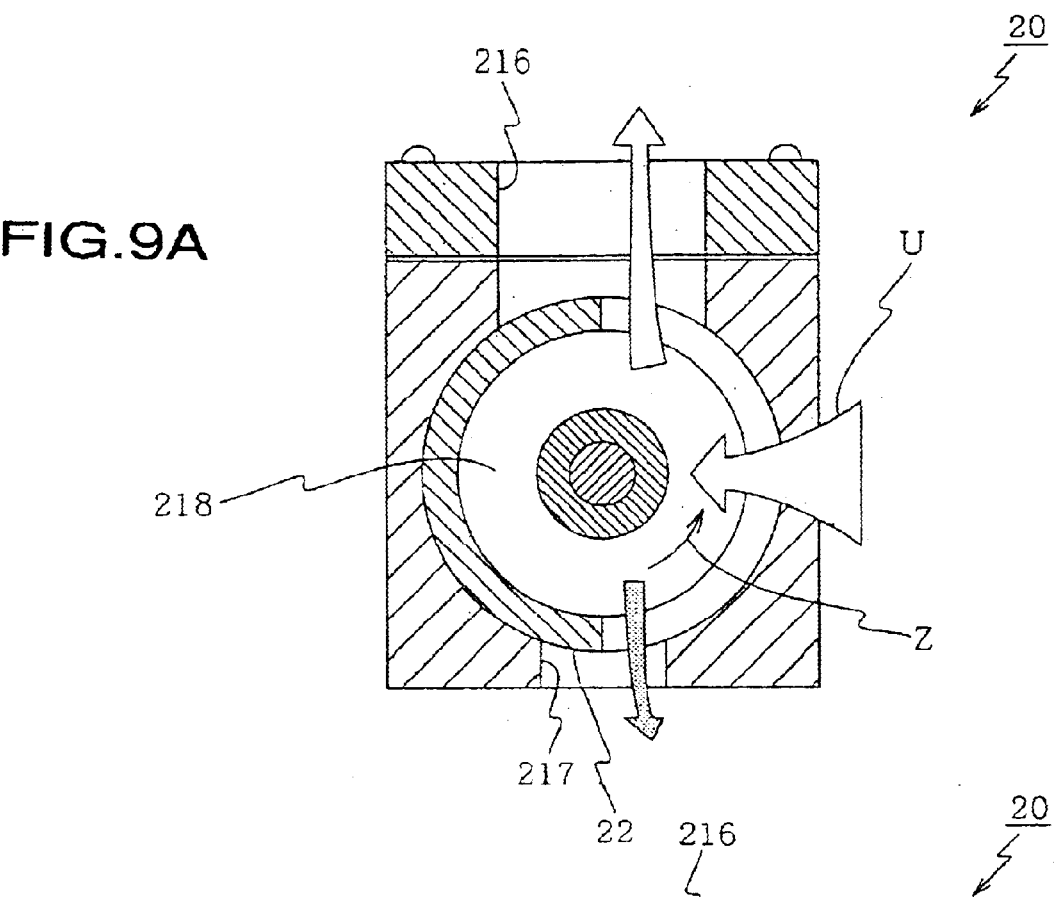
FIG. 9(A) shows a gas flow in the first flow path and FIG. 9(B) shows a gas flow in the second flow path.
Figure 9B:
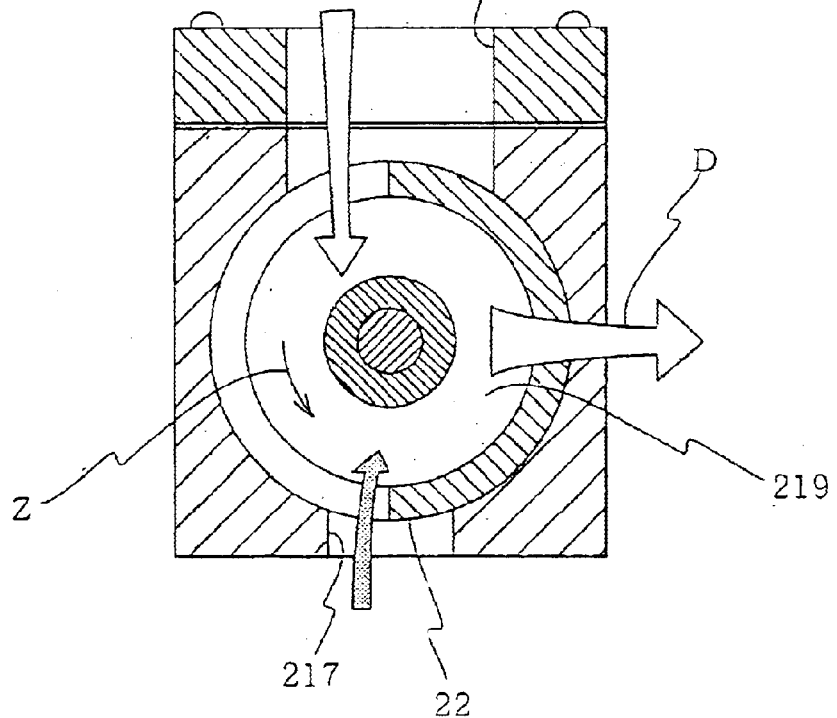
Figure 10A:
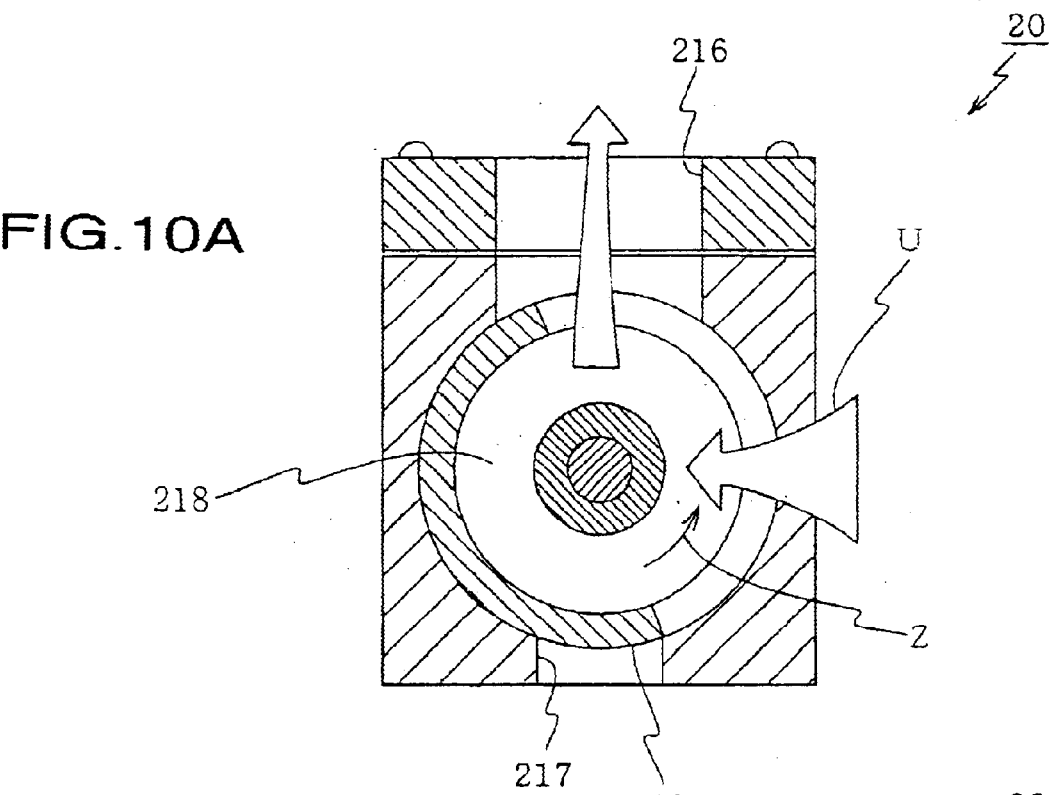
FIG. 10(A) shows a gas flow in the first flow path and FIG. 10(B) shows a gas flow in the second flow path.
Figure 10B:
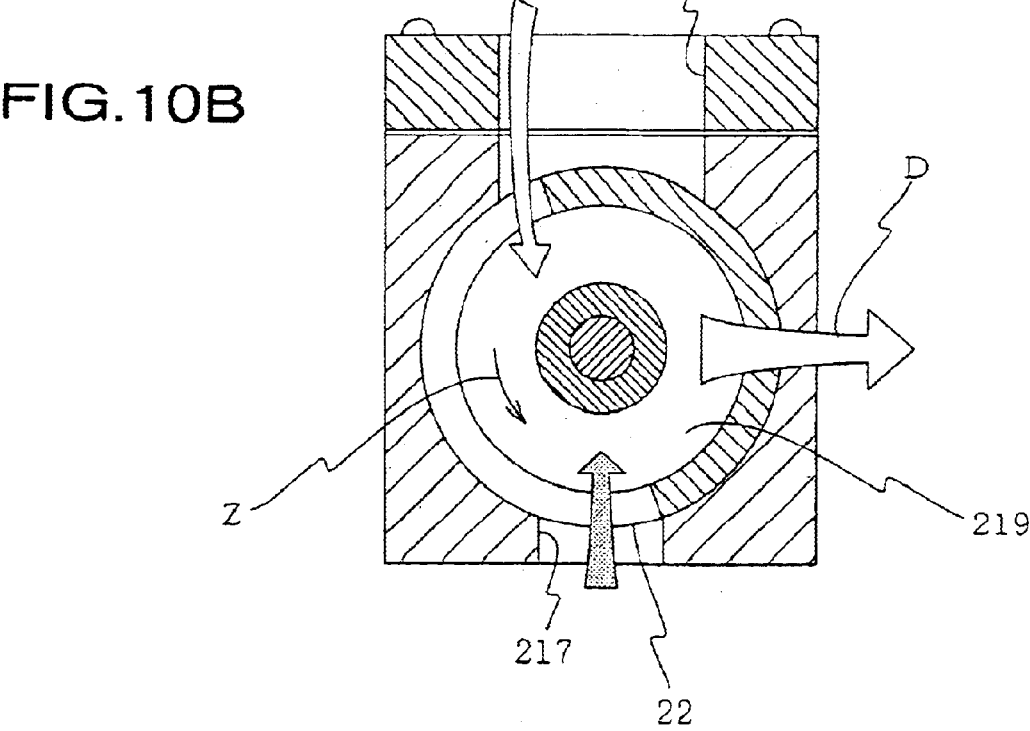

Referring to FIG. 4, when the upstream end of the first flow path 21 is immediately before the output port 217, the second flow path 219 is at a rotation angle "a", reaching the atmospheric port 217. This angle is preferably 10–50 degrees.

FIG. 3 through FIG. 10 show gas flows to the respective ports according to rotation of the switching valve member 22. In each of the figures, (A) represents a gas flow in the first flow path 218 and (B) represents a gas flow in the second flow path. In each of the figures, an arrow "U" shows a gas flow from the positive input port 214 to the oscillating air pressure generator 20, and an arrow "D" shows a gas flow sucked from the negative pressure input port 215 to the oscillating air pressure generator 20.

Referring to FIG. 3 through FIG. 10, explanation will be given on the operation of the oscillating air pressure generator 20. When the switching 22 is at a position that the first flow path 218 connects the positive pressure input 214 to the output port 217, and the second flow path 219 connects the negative port 215 to the atmospheric port 216 (FIG. 5 through FIG. 8), outer air is taken in through the atmospheric port 216 and supplied via the negative pressure input port 215 to the blower 52. Moreover, the outer air taken in is output from the output port 217 to the diaphragm unit 56 via the positive pressure input port 214.

The switching valve member 22 is further rotated and when the first flow path 218 connects the positive pressure input port 214 to the atmospheric port 216 and the second flow path 219 connects the negative pressure input port 215 to the output port 217 (FIG. 9, FIG. 10, and FIG. 3, FIG. 4), gas is sucked from the diaphragm unit 56 at the output port 217. Furthermore, the gas taken in is sucked by the blower 52 via the negative pressure input port 215 and exhausted into the atmosphere via the positive pressure input port 214 and the atmospheric port 216.

The switching valve member is driven by the drive nit 23 to repeat the aforementioned connection states, so that gas exhaust and take-in is continuously repeated at the output port 217, urging the oscillating air pressure to the diaphragm 56.

When generating the aforementioned oscillating air pressure, when the first flow path 218 of the switching valve member starts connection between the positive pressure input port 214 and the output port 217, the second flow path 219 has already connected the negative input port 215 to the atmospheric port 216. Accordingly, the outer air take-in precedes for supplying the outer air to the blower 52. The outer air taken in circulates in the blower 52 and at the moment when the positive pressure input port 214 is connected to the output port 217, the positive pressure urging to the diaphragm unit 56 is rapidly performed.

Accordingly, it is possible to suppress the time loss experienced in the conventional oscillating air pressure generator, i.e., the outer air taken requires a time for circulating in the blower and reaching the output port. Thus, without increasing the size of the blower, it is possible to maintain a high positive pressure of the oscillating air pressure, increasing the oscillation amplitude.

Figure 11:
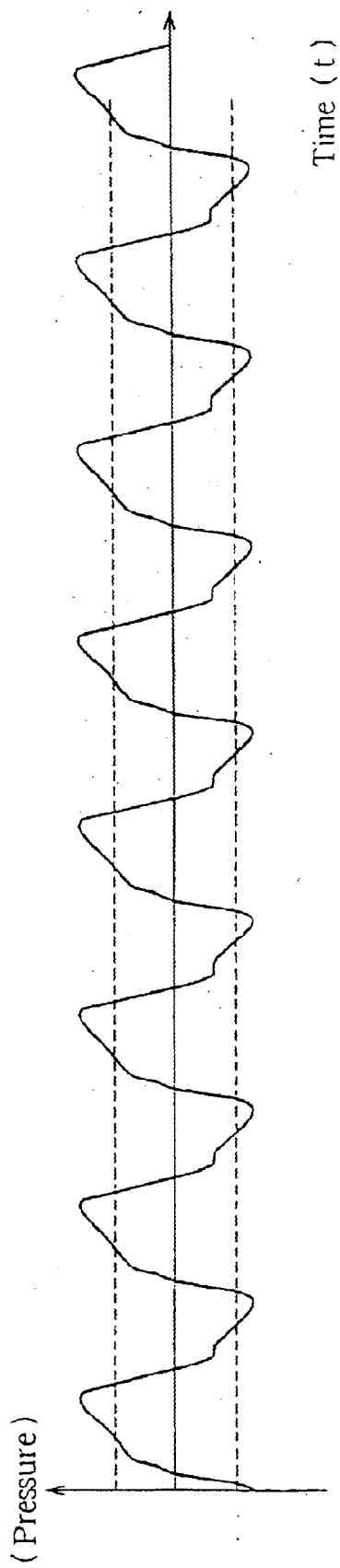
FIG. 11 shows a pressure amplitude of the oscillating air pressure obtained by the oscillating air pressure generator according to the first embodiment of the present invention.
Figure 12:
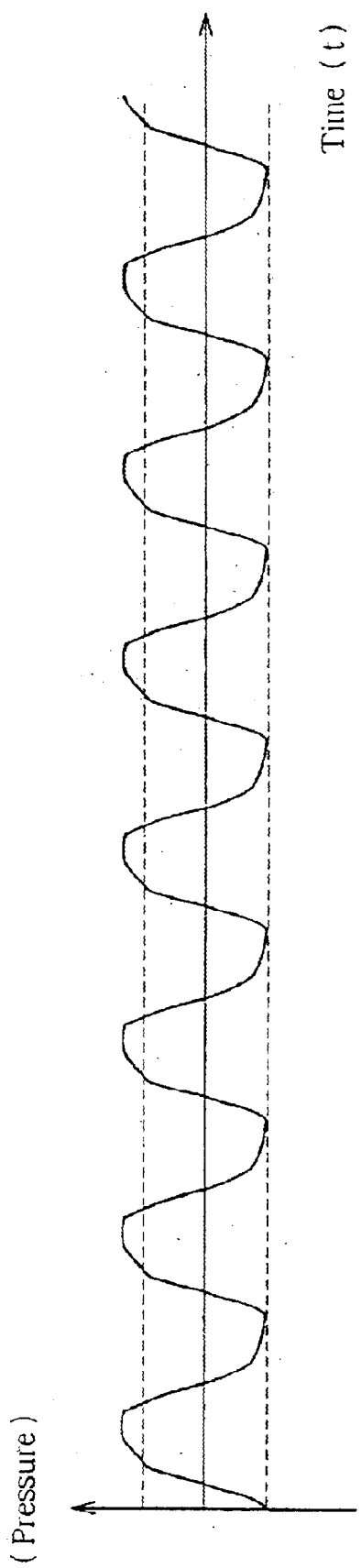
FIG. 12 shows a pressure amplitude of the oscillating air pressure obtained by a conventional oscillating air pressure generator.
Figure 13A:
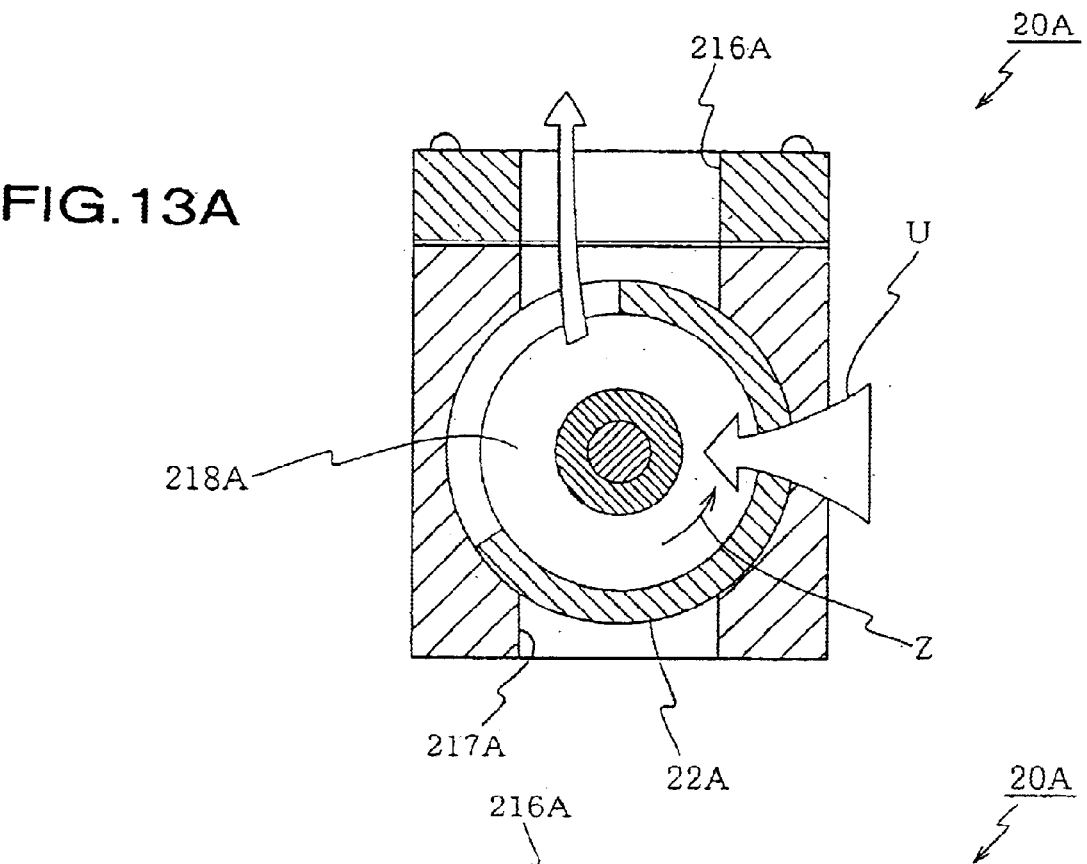
FIG. 13(A) shows a gas flow in the first flow path and FIG. 13(B) shows a gas flow in the second flow path.
Figure 13B:
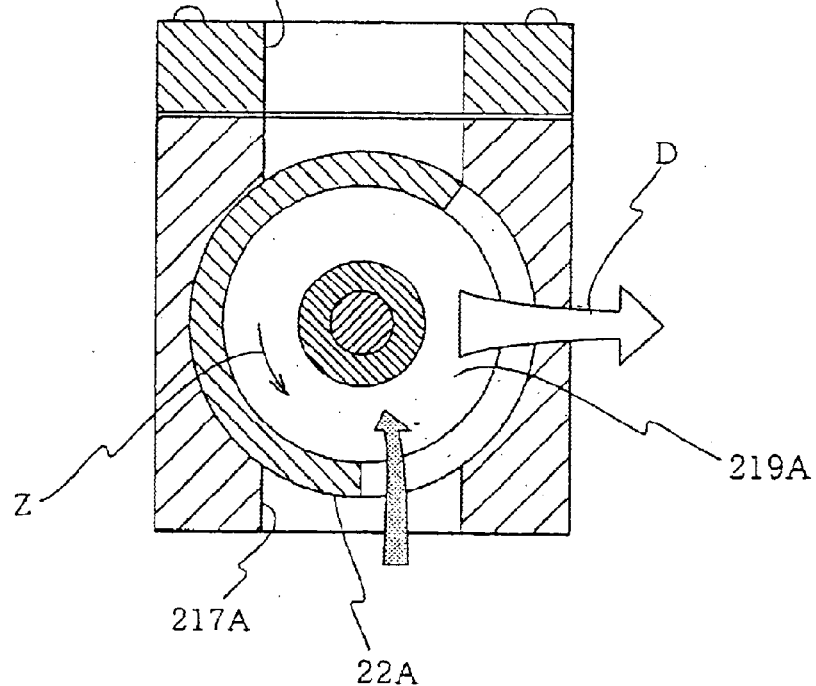
Figure 53:
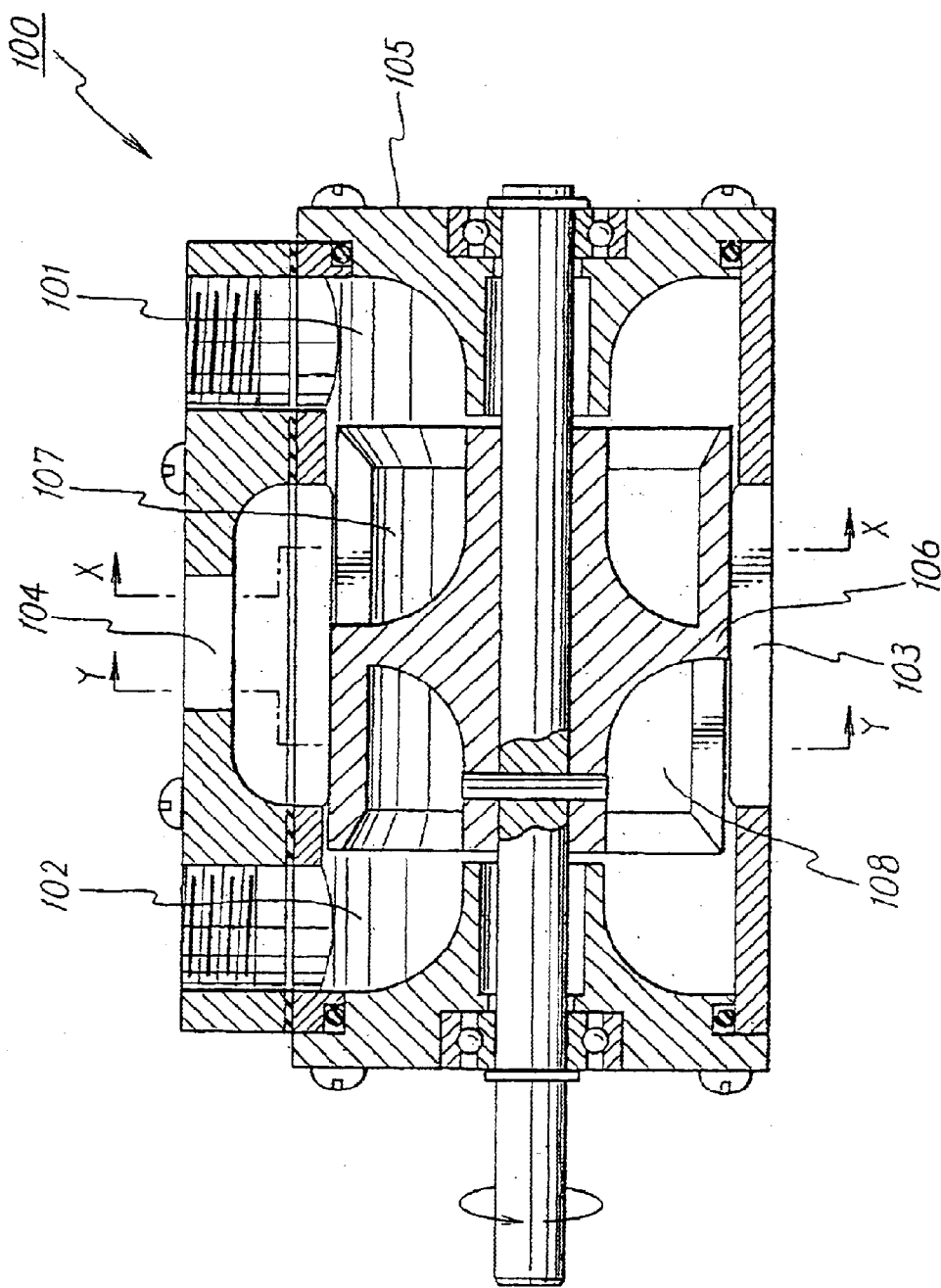
FIG. 53 is a cross sectional view of a conventional oscillating air pressure generator.
Figure 54A:
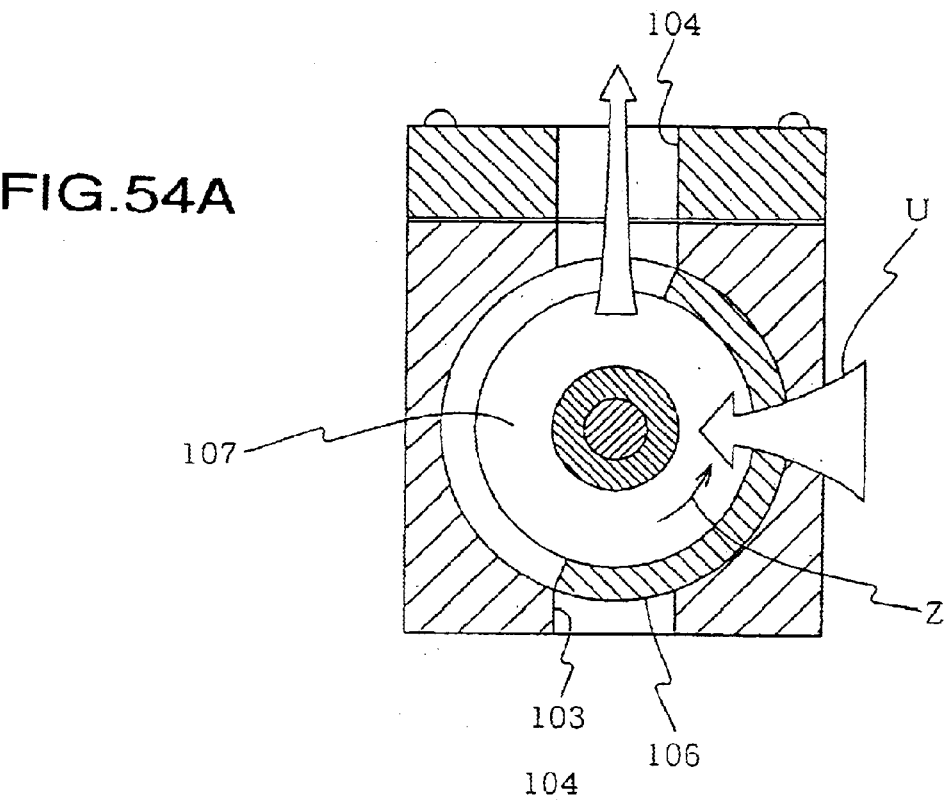
FIG. 54(A) is a cross sectional view about the line X—X in FIG. 53.
Figure 54B:
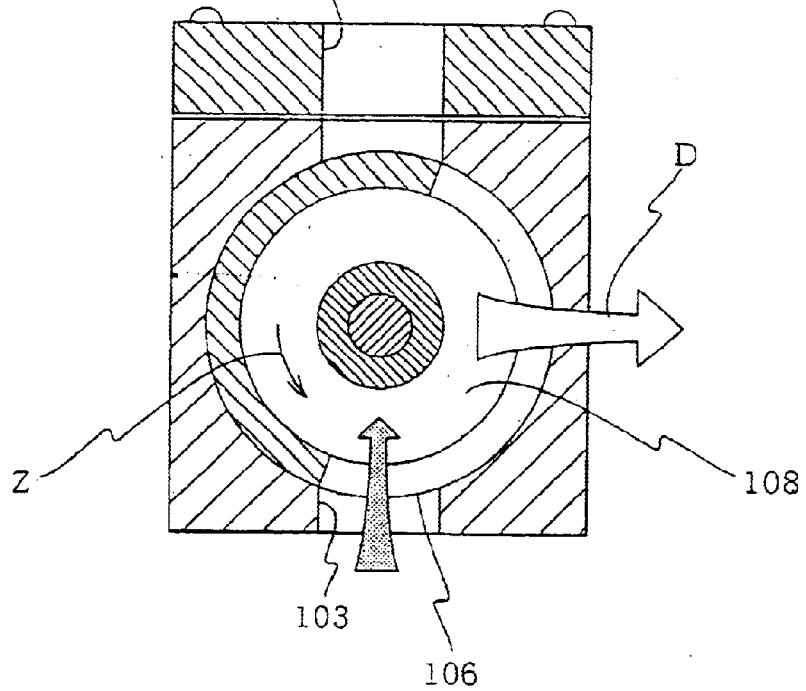
FIG. 54(B) is a cross sectional view about the line Y—Y in FIG. 53.
Figure 55A:
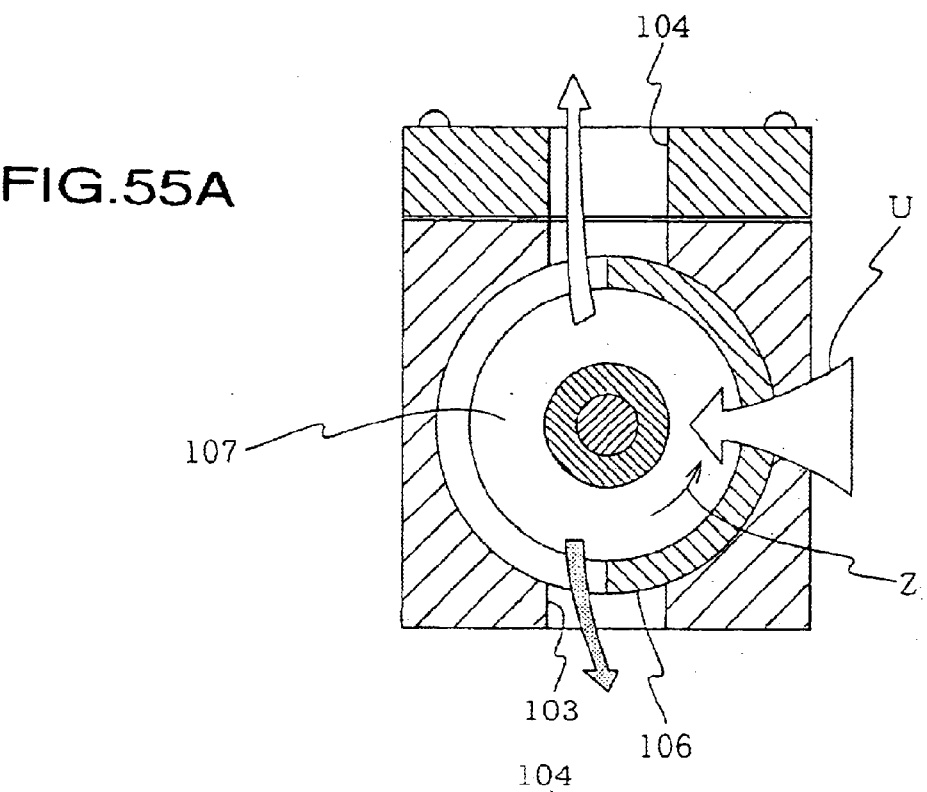
FIG. 55(A) is a cross sectional view showing a gas flow in a first flow path during operation.
Figure 55B:
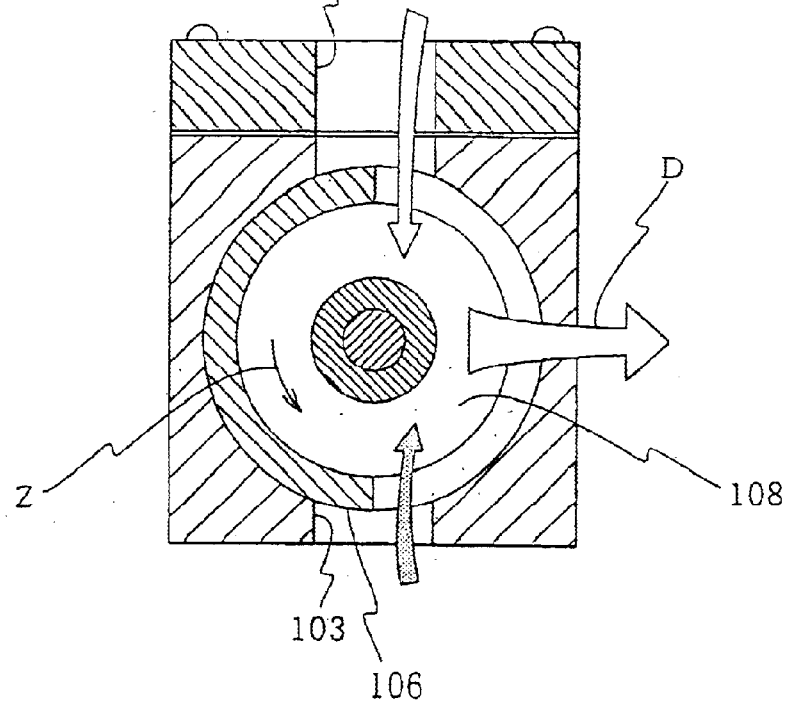
FIG. 55(B) is a cross sectional view showing a gas flow in a second flow path during operation.
Figure 56A:
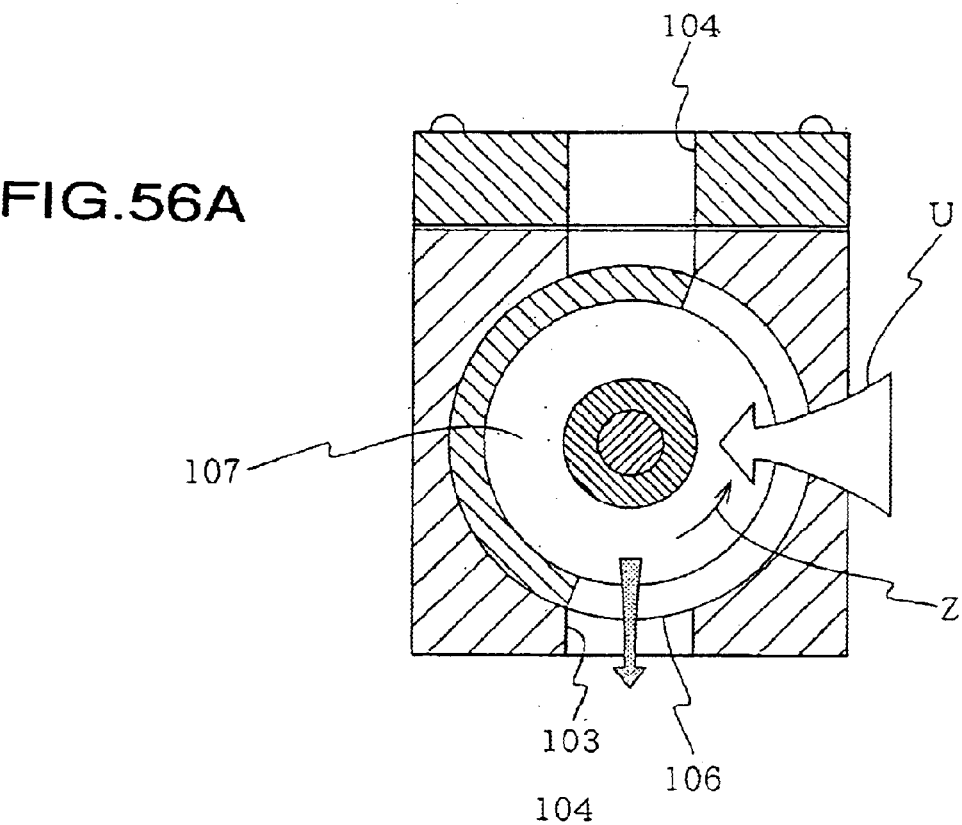
FIG. 56(A) is a cross sectional view showing a gas flow in the first flow path during operation.
Figure 56B:
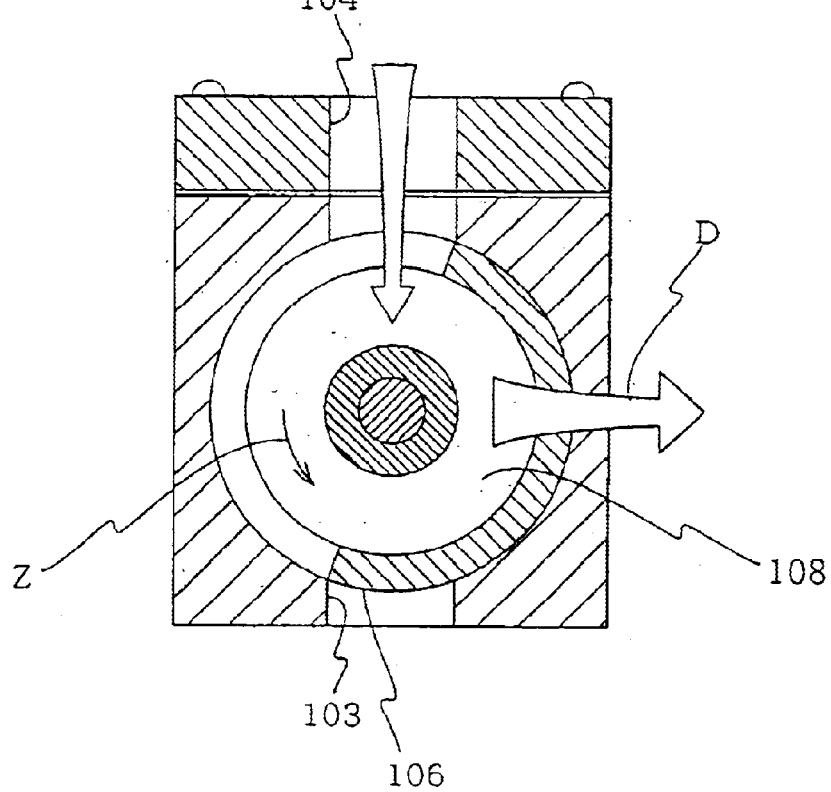
FIG. 56(B) is a cross sectional view showing a gas flow in the second flow path during operation.
Figure 57A:
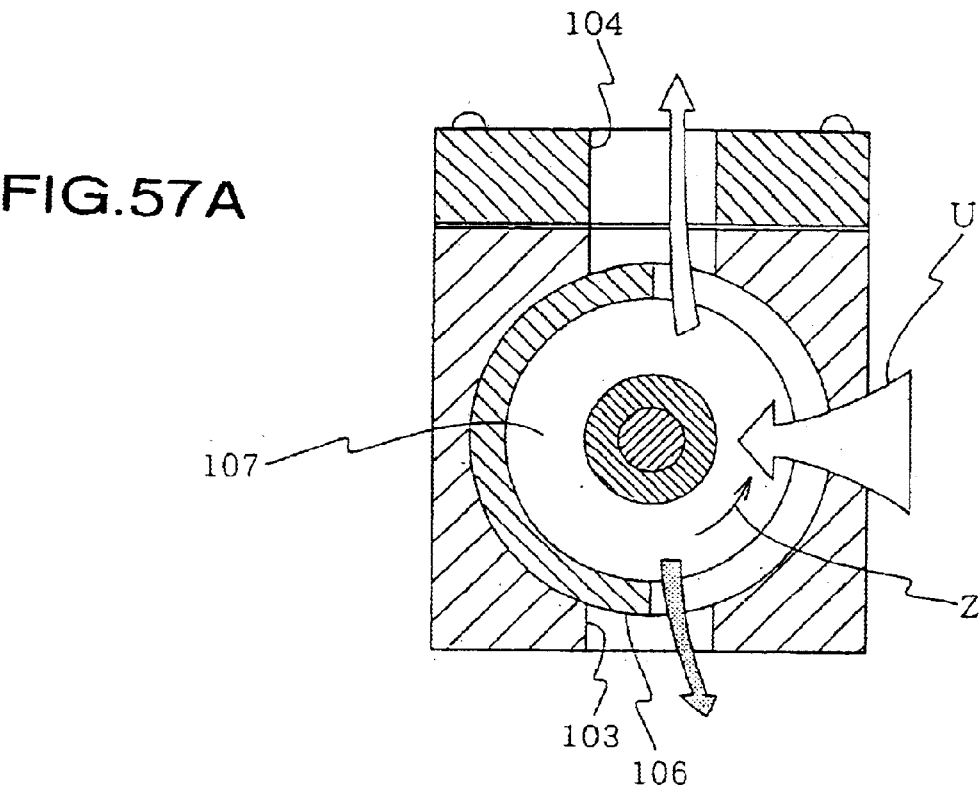
FIG. 57(A) is a cross sectional view showing a gas flow in the first flow path during operation.
Figure 57B:
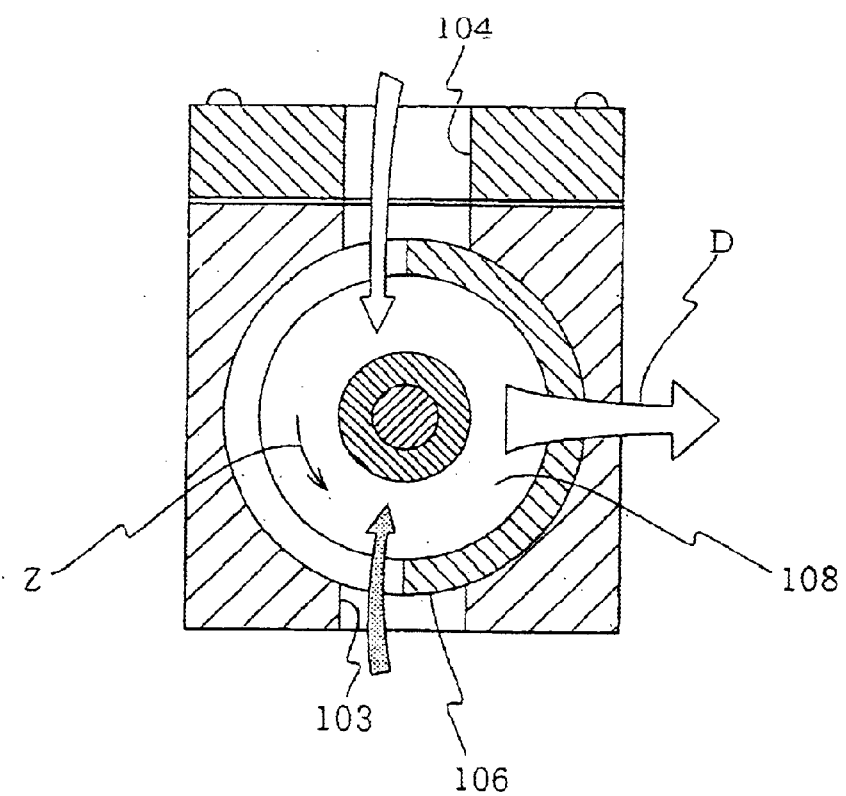
FIG. 57(B) is a cross sectional view showing a gas flow in the second flow path during operation.
Figure 58A:
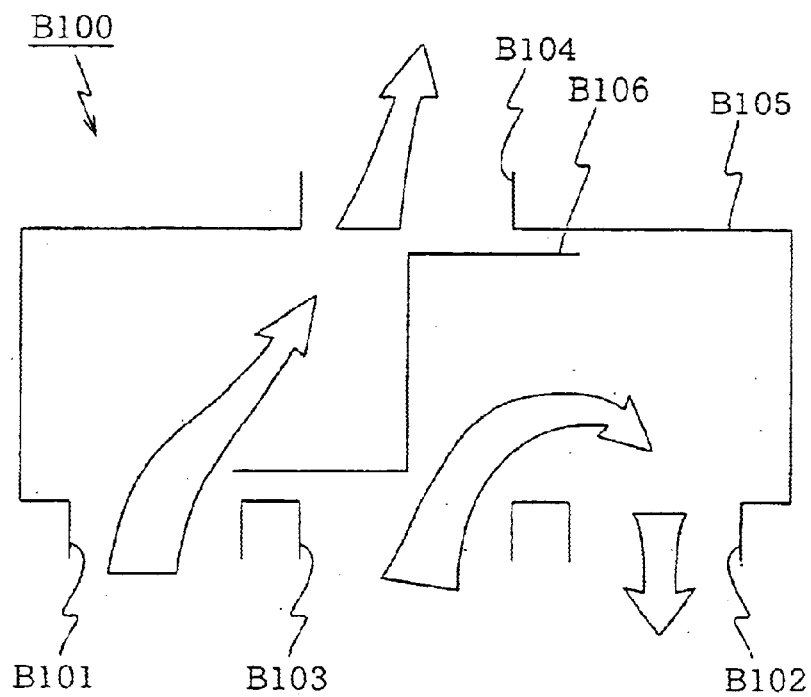
FIG. 58(A) schematically shows a first connection state of the oscillating air pressure generator of a conventional high-frequency artificial respiration apparatus, and FIG. 58(B) schematically shows a second connection state of the oscillating air pressure generator of a conventional high-frequency artificial respiration apparatus.
Figure 58B:
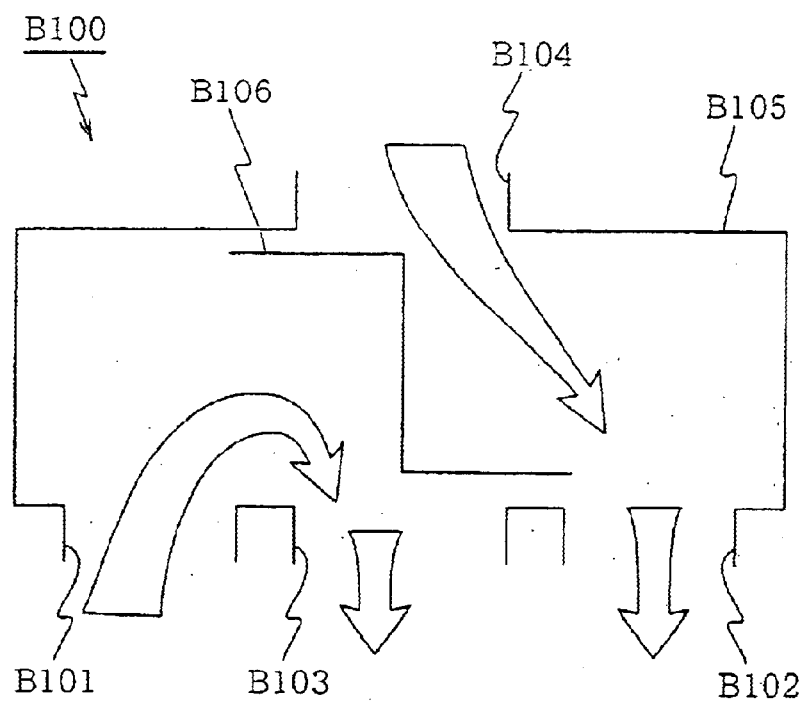
Figure 59:
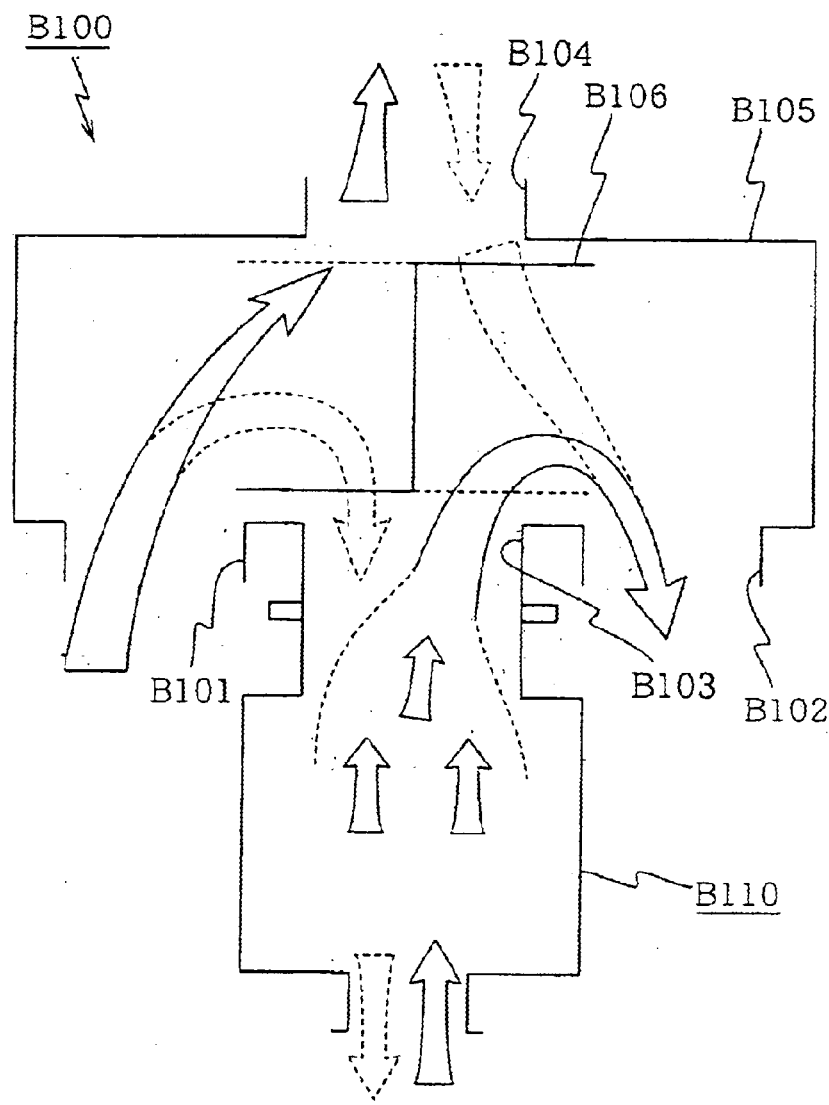
FIG. 59 is a block diagram showing a conventional configuration of a high-frequency artificial respiration apparatus including a silencer.

FIG. 11 and FIG. 12 show comparison test results between the aforementioned oscillating air pressure generator 20 according to the present embodiment and the conventional oscillating air pressure generator 100 shown in FIG. 53. FIG. 11 shows a pressure change of the oscillating air pressure in the oscillating air pressure generator 20 according to the present embodiment. FIG. 12 shows a pressure change of the oscillating air pressure in the conventional oscillating air pressure generator 100. As is clear from this test results, the oscillating air pressure generator 20 according to the present embodiment outputs a higher positive pressure and has a greater oscillation amplitude than in the conventional oscillating air pressure generator 100.

Here, in the aforementioned oscillating air pressure generator 20, the width of the atmospheric port 216 is set greater than the width of the output port 217, so that the timing of the connection of the negative pressure input port 215 and the atmospheric port 216 precedes the timing of the connection between the positive pressure input port 214 and the output port 217. This timing difference can also be obtained by adjusting the position or width of the first flow path and the second flow path 219. Hereinafter, such an example will be explained.

FIG. 13 through FIG. 18 are cross sectional views of an oscillating air pressure generator 20A in which an output port 217A and an atmospheric port 216A have identical width in the rotation direction of a switching valve member 22A and a cut-off portion of the frame is smaller than 180 degrees, so as to function in the same way as the aforementioned oscillating air pressure generator 20. In each of the figures, (A) is a cross sectional view of the first flow path 218A and (B) is a cross section of the second flow path 219A.

Figure 14A:
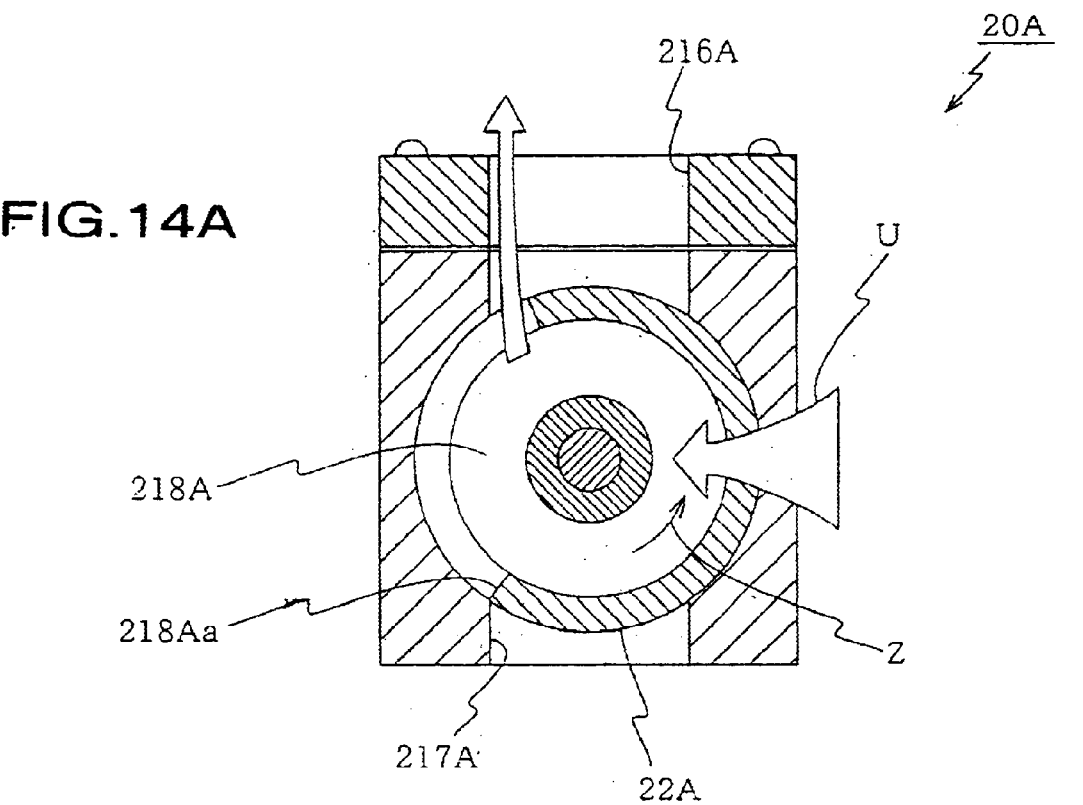
FIG. 14 is a continuation of FIG. 13 and shows a gas flow according to the rotation angle of the switching valve member of the oscillating air pressure generator. 14(A) shows a gas flow in the first flow path
FIG. 14(B) shows a gas flow in the second flow path.
Figure 14B:
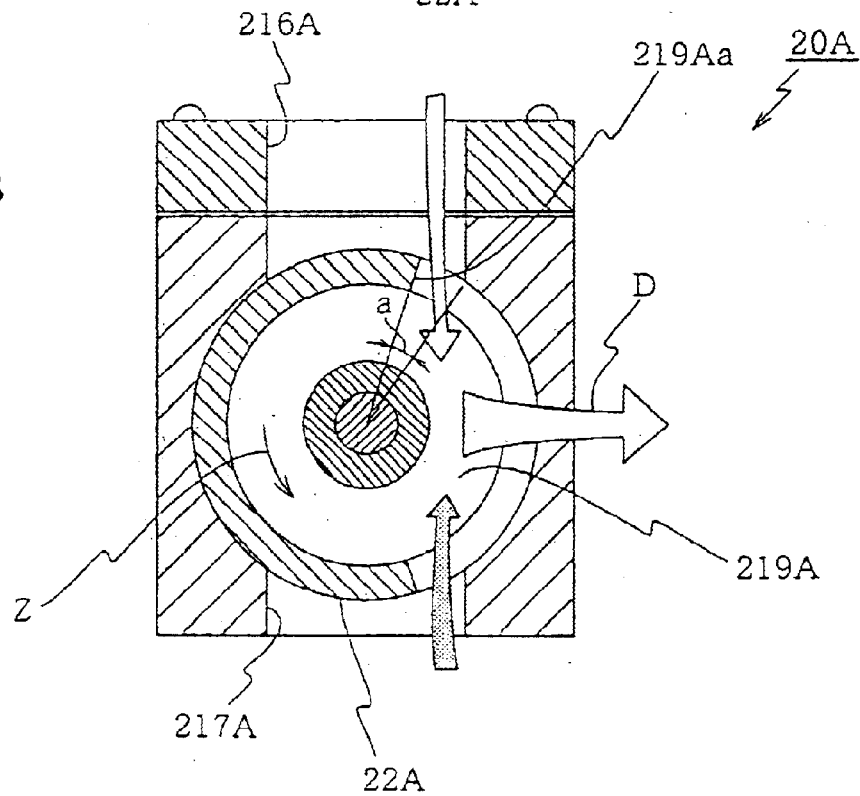
Figure 16A:
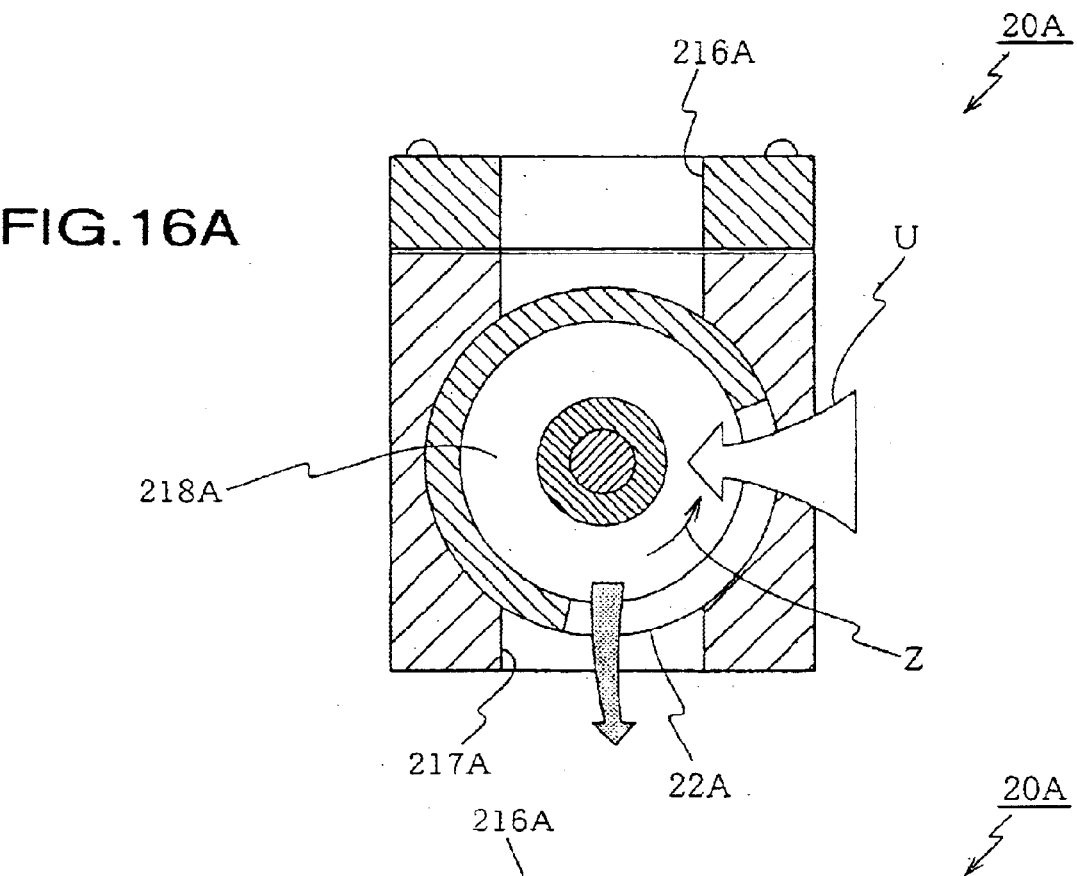
FIG. 16 is a continuation of FIG. 15 and shows a gas flow according to the rotation angle of the switching valve member of the oscillating air pressure generator. 16(A) shows a gas flow in the first flow path
FIG. 16(B) shows a gas flow in the second flow path.
Figure 16B:
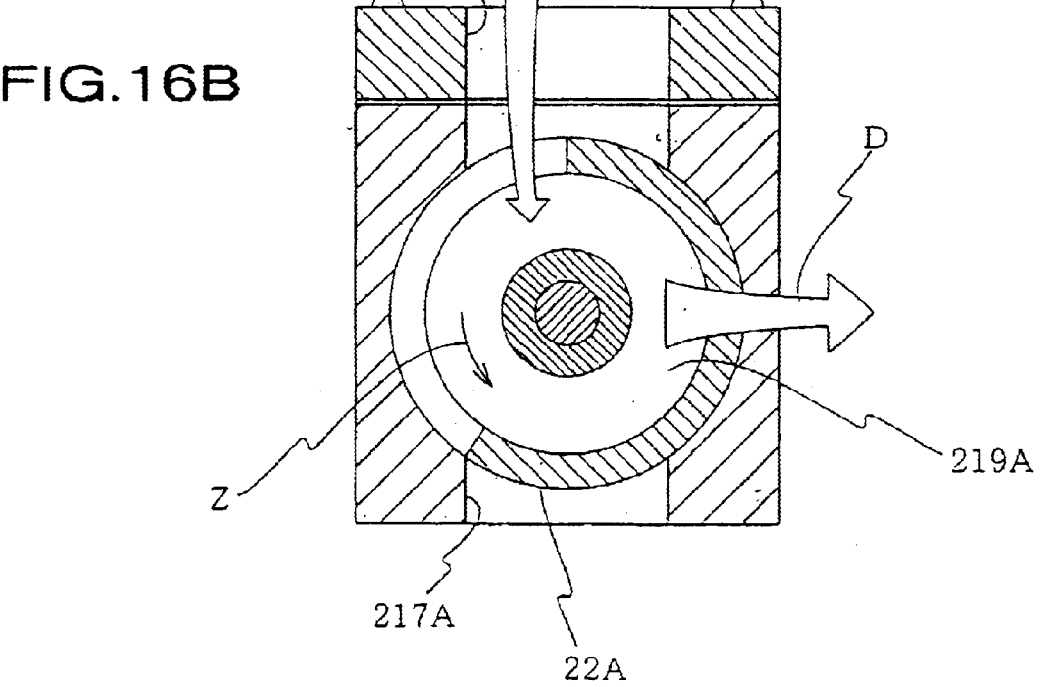
Figure 17A:
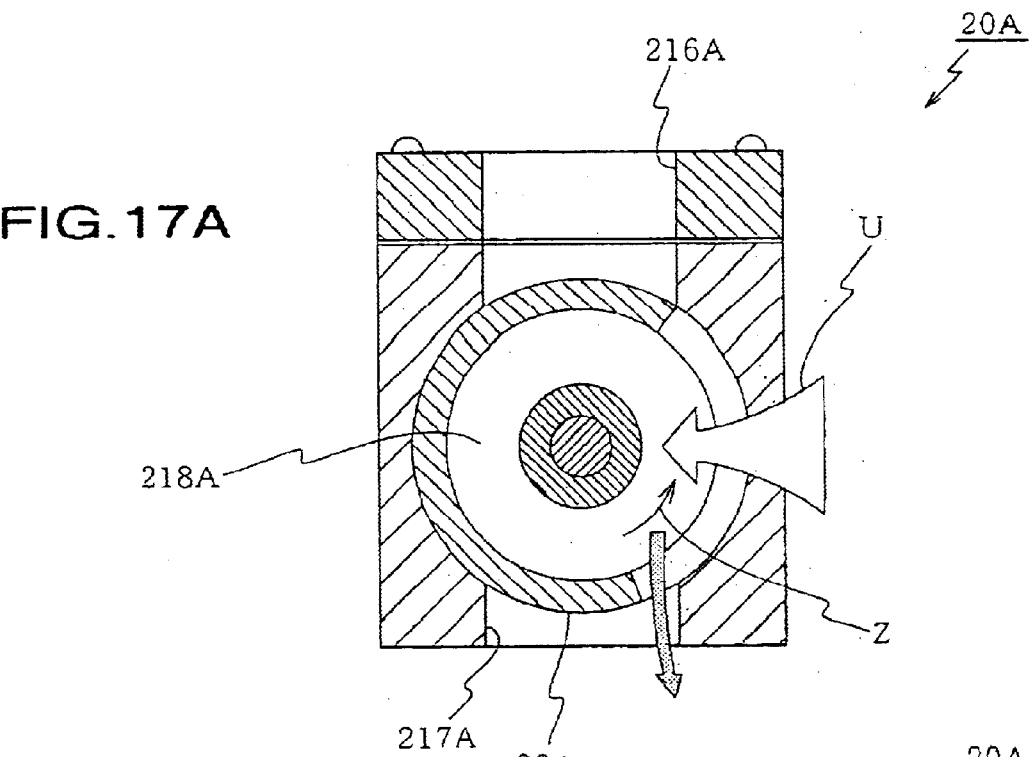
FIG. 17 is a continuation of FIG. 16 and shows a gas flow according to the rotation angle of the switching valve member of the oscillating air pressure generator. 17(A) shows a gas flow in the first flow path
FIG. 17(B) shows a gas flow in the second flow path.
Figure 17B:
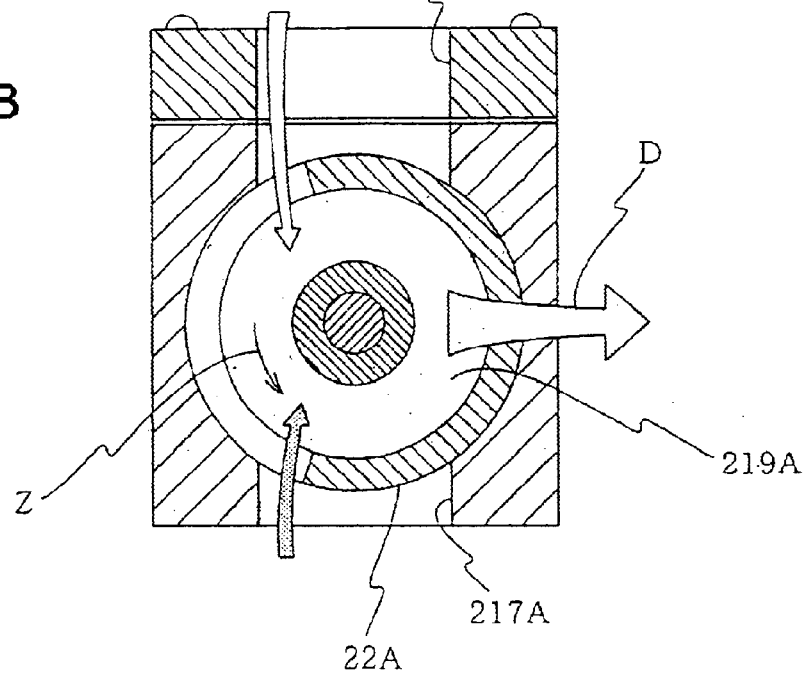
Figure 18A:
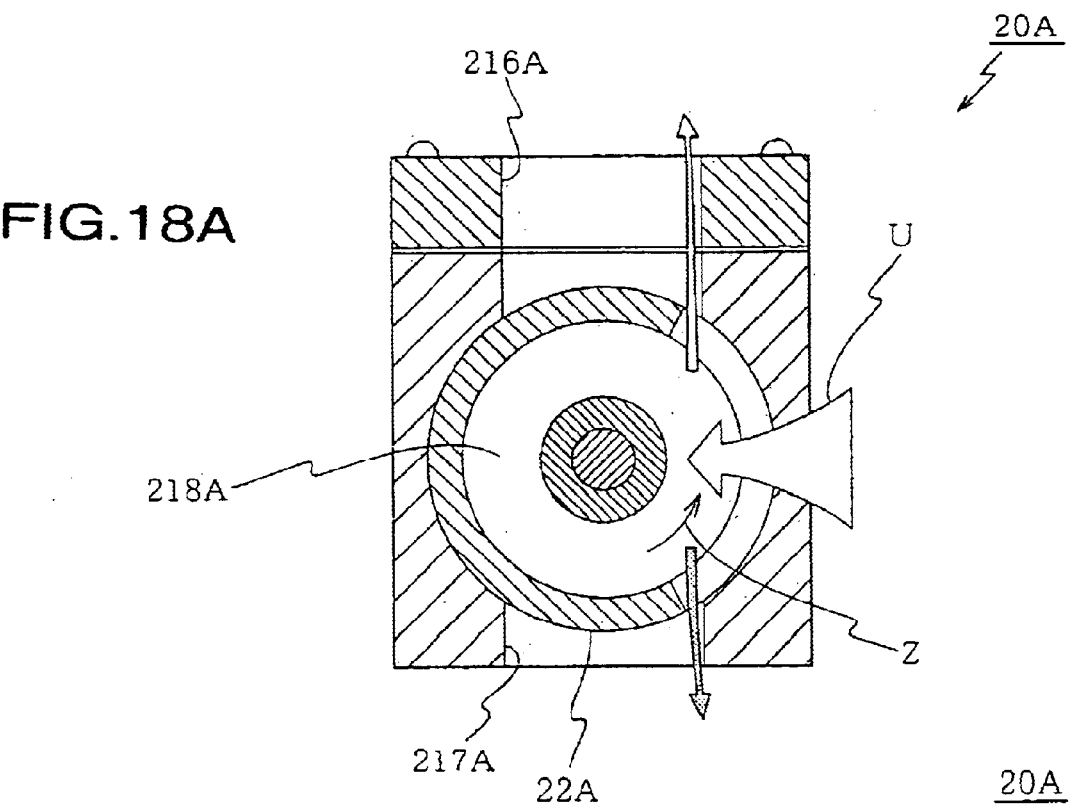
FIG. 18 is a continuation of FIG. 17 and shows a gas flow according to the rotation angle of the switching valve member of the oscillating air pressure generator. 18(A) shows a gas flow in the first flow path
FIG. 18(B) shows a gas flow in the second flow path.
Figure 18B:
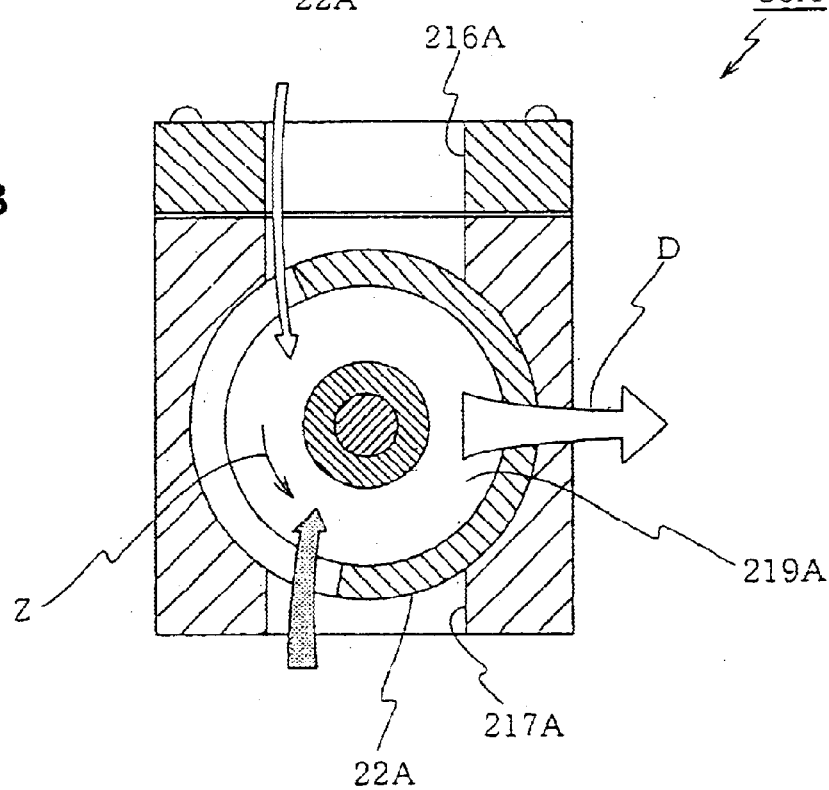

That is, the relative positional relationship between the first and the second flow paths or the width values in the rotation direction are set as follows. When an upstream end 218Aa of the cut-off portion is positioned at the same position as the downstream end of the output port 217A as shown in FIG. 14(A), the second flow path 219 has the upstream end 219Aa of the cut-off portion at an angle "a" with the downstream end of the atmospheric port 216 around the center shaft as shown in FIG. 14(B).

Referring to FIG. 13 through FIG. 18, explanation will be given on the operation of the oscillating air pressure generator 20. When the switching valve member 22A connects the positive pressure input port 214 with the output port 217A as the first flow path 218A and connects the negative pressure input port 215 with the atmospheric port 216A as the second flow path (FIG. 15 to FIG. 18), then atmosphere is taken in through the atmospheric port 216A and supplied via the negative pressure input port 215 to the blower 52. Moreover, the atmosphere taken in is output from the output port 217A via the positive pressure input port 214 to the diaphragm unit 56.

The switching valve member 22 is rotated and when the first flow path 218A connects the positive pressure input port 214 with the atmospheric port 216A and the second flow path 219A connects the negative pressure input port 215 with the output port 217A (FIG. 18, FIG. 13 to FIG. 15), in the output port 217A, air is sucked from the diaphragm unit 56. Furthermore, the air which has been taken in is sucked via the negative pressure input port 215 to the blower 52 and exhausted outside via the positive pressure input port 214 and the atmospheric port 216A.

As has been described above, when the first flow path 218A of the switching valve member 22 starts connection between the positive pressure input port 214 and the output port 217A, the second flow path 219A has connected between the negative pressure input port 215 and the atmospheric port 216A (FIG. 14). Accordingly, like in the oscillating air pressure generator 20, it is possible to maintain a high positive pressure increasing the oscillation amplitude.

Figure 19:
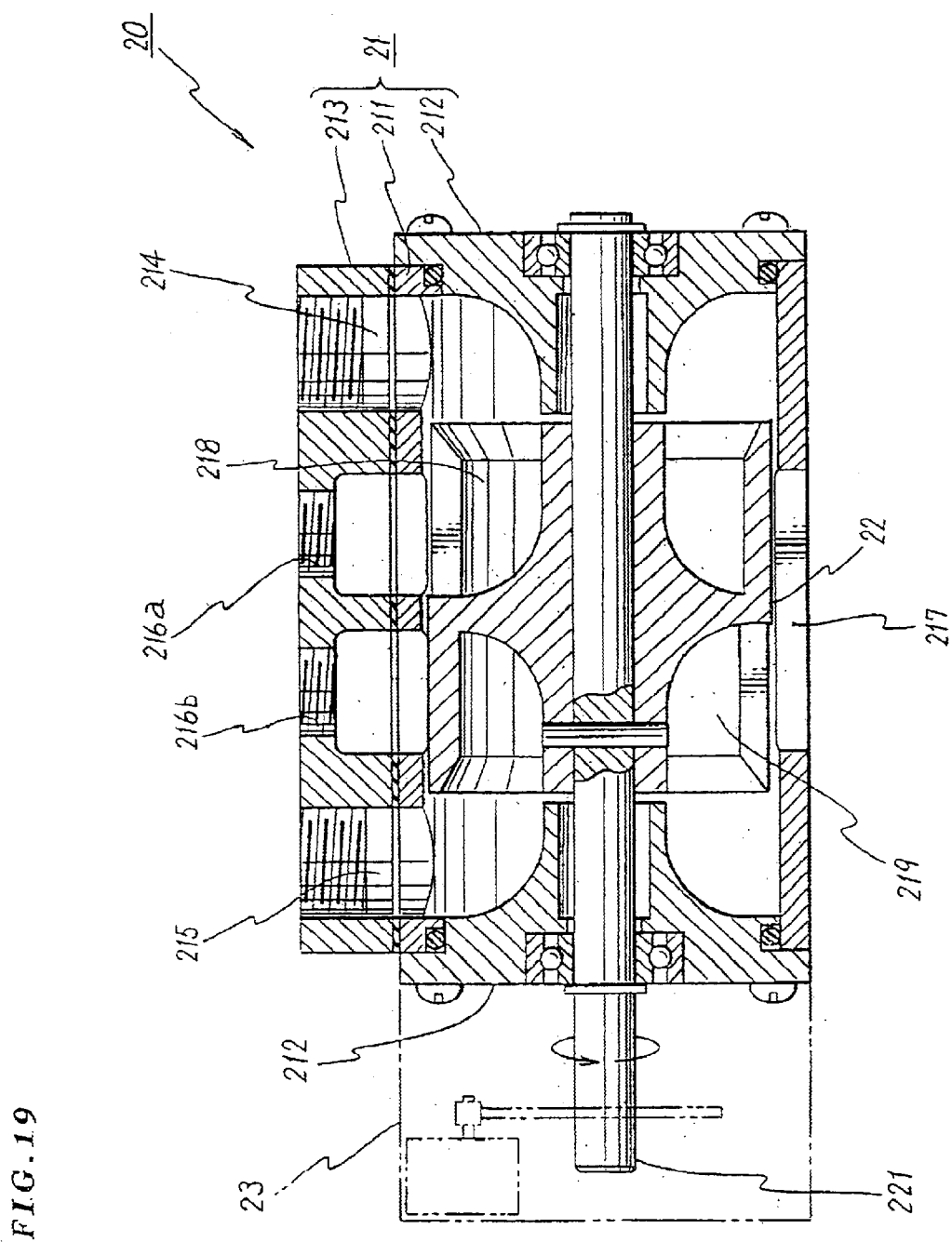
FIG. 19 is a cross sectional view about the rotary shaft of the oscillating air pressure generator as shown in FIG. 2 but having two atmospheric ports.

Moreover, as shown in FIG. 19, the frame 21 of the aforementioned oscillating air pressure generator 20 may include two atmospheric ports 216a and 216b for connecting to the positive pressure input port 214 and the negative pressure input port 215, respectively. The positive pressure air exhausted from the blower 52 is compressed and may have a high temperature. As shown in FIG. 2, when only one atmospheric port 216 is provided, a positive air of high temperature which has reached via the positive pressure input port 214 to the atmospheric port 216 may be again sucked by the negative input port 215 to be sent to the blower 52 according to the rotation angle of the switching valve member 22.

When air of high temperature is taken into the blower 52, inner parts such as a bearing is easily deteriorated, decreasing their service life. To cope with this, as shown in FIG. 19, two atmospheric ports 216a and 216b can be provided for the input ports 214 and 215, respectively. In this case, the positive pressure gas supplied from the positive pressure input port 214 will not be sucked via the atmospheric port into the negative pressure input port 215. Thus, by providing two atmospheric ports 216a and 216b, it is possible to effectively prevent introduction of a high temperature air into the blower, thus enabling to increase its service life.

Next, explanation will be given on the operation of the entire artificial respiration apparatus 12. A gas (oxygen) is supplied from the inhale gas supply unit 62 and the blower 52 starts drive. The positive and negative pressures generated by the blower 52 is converted into an oscillating air pressure by the oscillating air pressure generator 20 and sent to the diaphragm unit 56. In the diaphragm unit 56, the diaphragm 561 oscillates with the periodicity of the oscillating air pressure, so as to change the inner pressure in the inhale pipe 623. Accordingly, the inhale gas passing through the inhale pipe 623 is subjected to the oscillating air pressure and reaches lungs of a patient who cannot breath by himself or herself. Thus, oxygen in the inhale gas reaches the patient's lungs. Moreover, the inhale gas supplied reaches the patient's lungs in an oscillated state. Moreover, the exhale gas containing carbon dioxide advances in the opposite direction to the inhale gas through the inhale end pipe 605 and exhausted from the exhaust pipe 604. Here, the three-way branched pipe provides a region for passing the inhale gas and the region for passing the exhale gas.

The artificial respiration apparatus 12 according to the present embodiment includes the aforementioned oscillating air pressure generator 20, which enables to supply an inhale gas with a greater pressure oscillation amplitude than in the conventional apparatus. This in turn increases the ventilation amount. Moreover, there is no need of increasing size of the blower, which leads to reduction of power consumption and production costs as well as size of the entire apparatus.

Figure 21C:
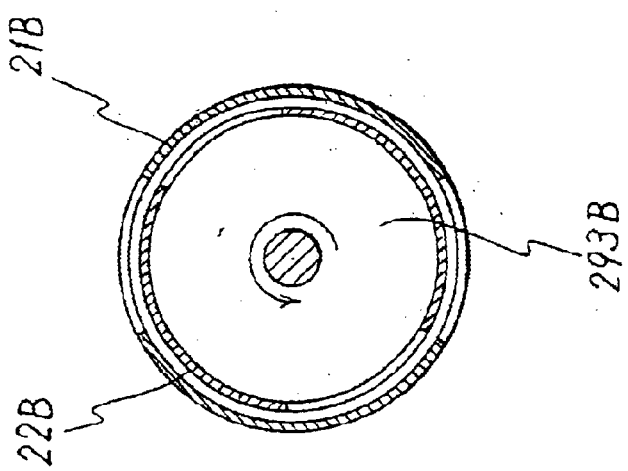
FIG. 21(C) is a cross section when the valve member is rotated "a" degrees from the position of FIG. 21(B).
Figure 21B:
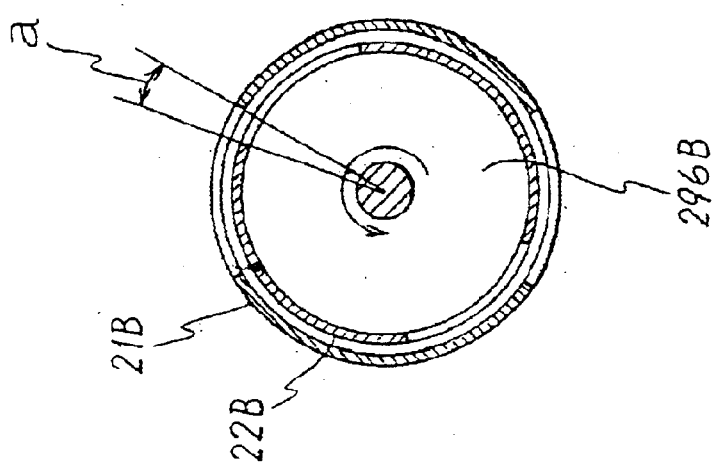
FIG. 21(B) is a cross section of the gas flow in a third flow path.
Figure 21A:
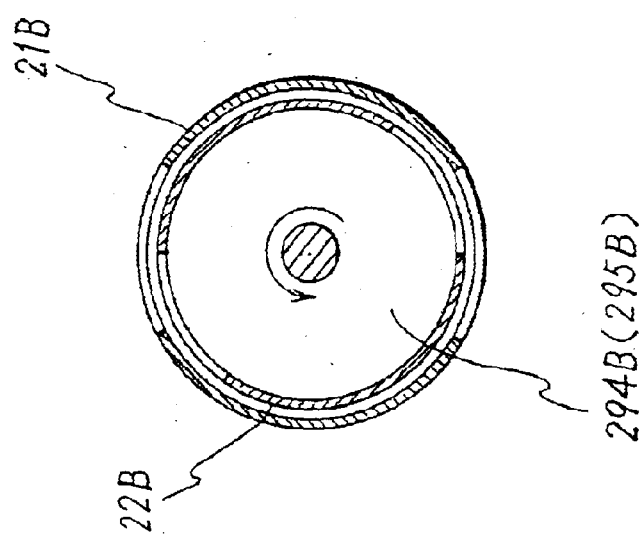
FIG. 21(A) is a cross section of the gas flow in a fourth and fifth flow path.

FIG. 20 and FIG. 21 show another example of the oscillating air pressure generator 20B.

This oscillating air pressure generator 20 includes: a frame 21B having a positive pressure input port 214B, a negative pressure input port 215B, an atmospheric port 216Ba and 216Bb, and an output port 217B; a switching valve member as a rotary body rotatably mounted on the frame 21B; and a drive unit (not depicted) for rotating the switching valve member 22B.

The respective ports function in the same way as the ports of the aforementioned oscillating air pressure generator 20. The difference is that there are provided two atmospheric ports: one (216Ba) for connection to the positive pressure input port 214B and the other (216Bb) for connection to the negative pressure input port 215B.

The frame 21B is a cylindrical body having two end covered. The frame 21 is supported by a rotary shaft 221 inserted through the center of the cylindrical body. The frame 21B has an inner diameter slightly greater than the outer diameter of the switching valve member 22B, so that the switching valve member 22B can smoothly rotate in side the frame 21B.

In the external circumference of the frame 21, at the upper portion in FIG. 20, there are provided four through holes. Of these, the leftmost hole serves as an atmospheric port 216 corresponding to the negative pressure input port 215B, and the rightmost hole is an atmospheric port 216Ba corresponding to the positive pressure input port 214B. And the central two ports constitute 217Ba and 217Bb constitute output port 217B.

Moreover, similarly, at the lower portion of the frame 21B, there are provided four through holes at an almost identical interval. Of these, two through holes 215Ba and 215Bb at the left constitute a negative pressure input port 215B, and two through holes 214Ba and 214Bb at the right constitute a positive pressure input port 215B.

On the other hand, the switching valve member 22B has four flow paths: a third flow path 293B for communicating the through hole 214Bb of the positive pressure input port 214B; a fourth flow path 294B for communicating the through hole 214Ba of the positive pressure input port 214 with the atmospheric port 216Ba; a fifth flow path 295B for communicating the through hole 215Ba constituting the negative input port 215B with the through hole 217Bb constituting the output port 217B; and a sixth flow path 296B for communicating the through hole 215 constituting the negative input port 215B with the atmospheric port 216Bb. It should be noted that each of the through holes provided in the switching valve member 22B and each of the through holes provided in the frame 21B have identical open angle around the rotary shaft 221B. The flow paths are arranged in the order of the sixth flow path 296B, the fifth flow path 295B, the third flow path 293B, and the fourth flow path 294B from the left.

That is, the switching valve member 22B is a hollow body whose interior is divided into four chambers. Each of the chambers has two through holes sandwiching the rotary shaft 221B. These through holes serve as the aforementioned flow paths 293B, 294B, 295B, and 296B.

When assuming a horizontal plane of the paper surface is a reference angle, FIG. 20 shows the fifth flow path 295B and the fourth flow path 294B arranged with their cut-off portions in the horizontal direction, and the third flow path 293B arranged with its cut-off portion arranged in the vertical direction with respect to the reference angle. Here, the sixth flow path 296B is arranged not exactly vertical to the paper surface but has some angle (10 to 50 degrees) with respect to the third flow path 293B.

Here, the third flow path 293B is at a right angle with respect to the reference angle. Difference between the reference angle and the angle of the sixth flow path is less than 90 degrees. The difference between the angle of the sixth flow path 296B and the angle of the third flow path is indicated by "a" in FIG. 21B.

When the switching valve member 22B is rotated in the Z direction by 90 degrees from the state of FIG. 20, the fourth flow path 294B connects the positive pressure input port 214B to the atmospheric port 216Ba. Simultaneously with this, the fifth flow path 295B connects the negative pressure input port 215B to the output port 217B.

When the switching valve member 22B is rotated in the Z direction further by (90–a) degrees, the sixth flow path 296B connects the negative pressure input port 215B to the atmospheric port 216Bb. Moreover, when the switching valve member is rotated further by "a" degrees, the third flow path 293 connects the positive pressure input port 214B to the output port 217B.

Thus, when the third flow path 293B starts connection between the positive pressure input port 214B and the output port 217B, the sixth flow path 296B has already connected the negative pressure input port 2215B to the atmospheric port 216Bb. Accordingly, like the oscillating air pressure generator 20, it is possible to maintain a high oscillating air pressure, increasing the oscillation amplitude.

Figure 22:
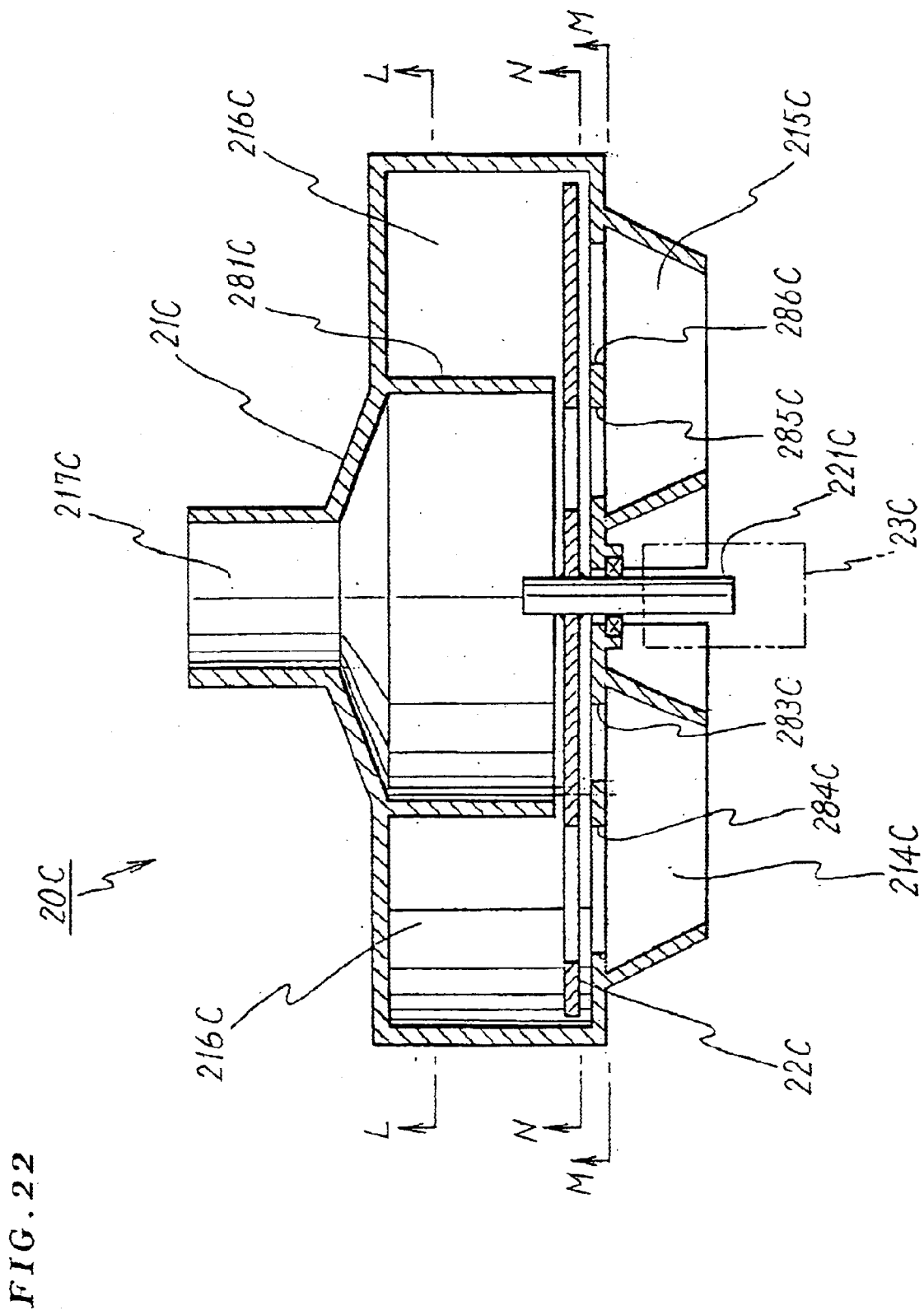
FIG. 22 is a cross sectional view about a rotary shaft of still another (third) example of the oscillating air pressure generator.

FIG. 22 and FIG. 23 show still another example of oscillating air pressure generator 20C.

This oscillating air pressure generator 20C includes: a frame 21C having a positive pressure input port 214C, a negative pressure input port 215C, an atmospheric port 216C, and an output port 217C; a switching valve member 22C constituted by a rotary disc rotatably mounted on the frame 21; a drive unit 23C having an identical configuration a the aforementioned drive unit 23.

The respective ports function in the same way as the ports of the oscillating air pressure generator 20.

The interior of the frame 21C is divided by the rotary disc 22C and an inner wall 282 C into the upper and lower portions. The atmospheric port 216C and the output port 217C are located in the upper portion. The positive pressure input port 214C and the negative input port 215C are located in the lower portion.

23(A) is a cross sectional view about the line L—L in FIG. 22. FIG. 23(B) is a cross sectional view about the line M—M in FIG. 22 (in which the rotary disc is not depicted). FIG. 23(C) shows the rotary disc 22C viewed from the line N—N in FIG. 22. As can be seen from 23(A), the upper portion of the frame 21C is divided by a cylindrical wall 281C around the rotary shaft 221C into two parts: the inner portion surrounded by the cylindrical wall serves as an output port 217C and the outer portion serves as an atmospheric port 216C.

Moreover, as can be seen from FIG. 23(B), the lower portion of the frame 21C is divided by a diameter into a right region and a left region. The left region serves as the positive pressure input port 214C, and the right region serves as the negative pressure input port 215C.

The Respective Ports

In the positive pressure input port 214C, a through hole 283C for communication with the output port 217C is provided inside the cylindrical wall 281 above the inner wall 282; and a through hole 284 for communication with the atmospheric port 216C is provided outside cylindrical wall 281C.

In the negative pressure input port 215C, a through hole for communication with the output port is provided within the cylindrical wall 281 above the inner wall 282; and a through hole for communication with the atmospheric port 216C is provided outside the cylindrical wall 281C.

Furthermore, as is clear from FIG. 23(C), the rotary disc has through holes, a first through hole 287C and a second through hole 288C at positions to sandwich the rotary shaft 221C. The first through hole 287C is arranged inside the cylindrical wall 281C so as to be able to communicate with the through hole 283C of the positive pressure input port 214C or the through hole 285C of the negative pressure input port 215C. The second through hole 288C is arranged outside the cylindrical wall 281C so as to be able to communicate with the through hole 284C of the positive pressure input port 214C or the through hole 286C of the negative pressure input port 215C.

Accordingly, the through hole 287C of the rotary disc 22C is always facing the output port 217C and the through hole 288C of the rotary disc 22C is always facing the atmospheric port 216C. Moreover, with rotation of the rotary disc 22B, the through holes 287C and 288C alternately face the positive pressure input port 214C and the negative pressure input port 215C.

Accordingly, with rotation of the rotary disc 22C, the positive pressure input port 214C and the negative pressure input port 215C communicate alternately with the atmospheric port 216C and the output port 217C, thus generating an oscillating air pressure from the output port 217C.

Furthermore, as shown in FIG. 223(C), the upstream end of the second through hole 288C defines an angle "a" (a=10 to 50 degrees) with a diameter defining the upstream end of the first through hole 287C. Accordingly, when the first through hole 287C starts connection between the positive pressure input port 214C and the output port 217C, the second through hole 288C has already connected the negative pressure input port 215C to the atmospheric port 216C. Consequently, like in the oscillating air pressure generator 20, it is possible to maintain a high positive pressure, increasing the oscillation amplitude.

Here, it is also possible to function the atmospheric port 216C as the positive pressure input port 214C and function the positive pressure input port 214C as the atmospheric port 216C.

Moreover, it is possible assign the inner portion of the cylindrical wall 218C as the atmospheric port 216C and the outer portion as the output port 217C. Furthermore, it is possible to interchange the positions of the positive pressure input port 214C and the negative pressure input port 215C.

Embodiment 2

Figure 24:
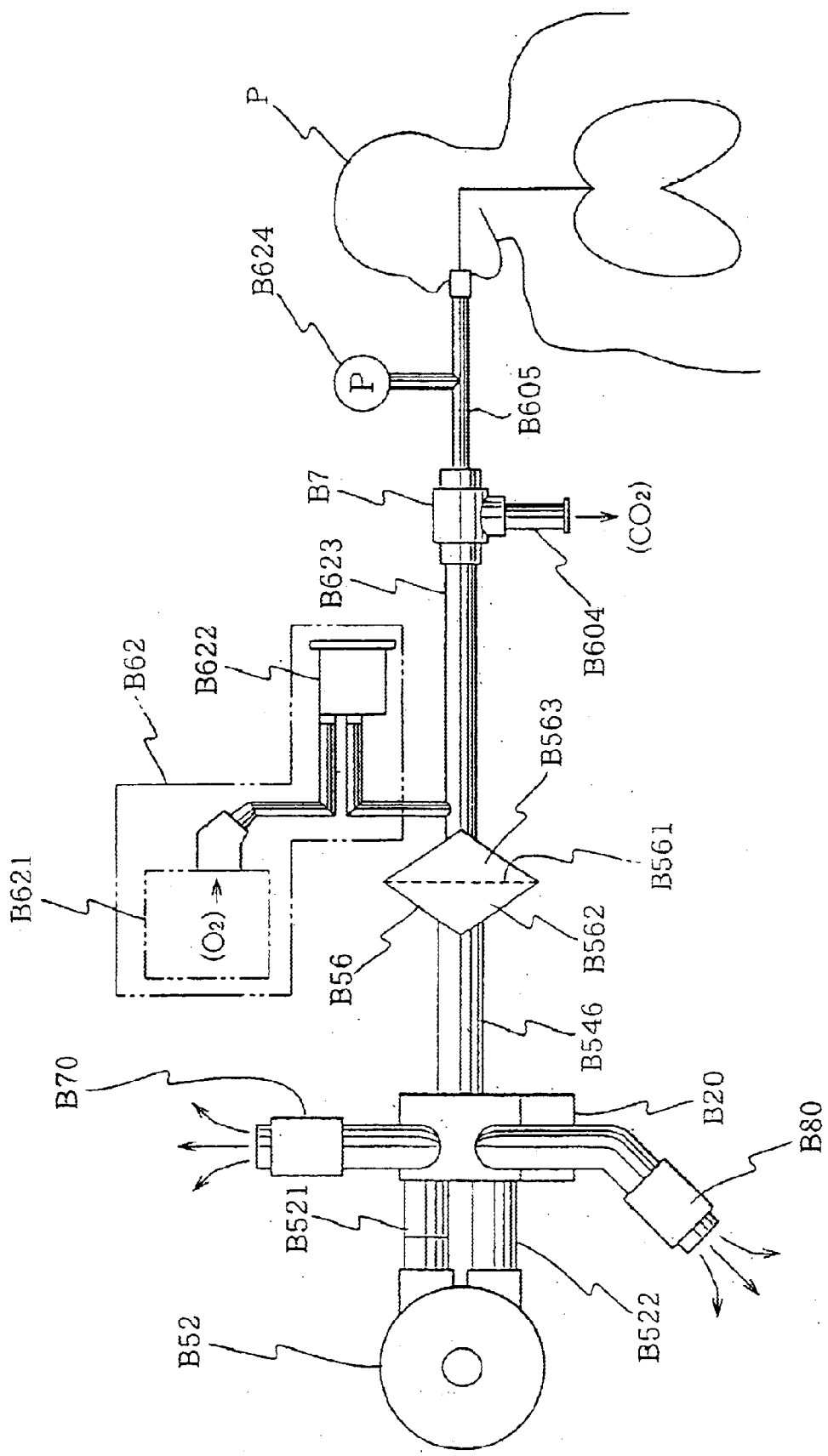
FIG. 24 shows a configuration of an artificial respiration apparatus according to a second embodiment of the present invention.

Description will now be directed to a second embodiment of the present invention with reference to FIG. 24 through FIG. 34. In this embodiment, an example is given for an oscillating air pressure generator B20 mounted on an artificial respiration apparatus B12 of a high-frequency oscillation (HFO) for performing oxygen inhale and exhale exhaust to a patient P. As shown in FIG. 24, the artificial respiration apparatus B12 includes: an inhale gas supply unit B62, a blower B52 (air generation source) for simultaneously generating a positive pressure and a negative pressure; an oscillating air pressure generator B20 for alternately selecting the positive pressure and the negative pressure so as to be converted into a predetermined oscillation air pressure; a diaphragm unit B56 operated by the oscillating air pressure from the oscillating air pressure generator B20, so as to apply an oscillation air pressure to the oxygen (mixture of oxygen and air) supplied to the patient P; and a pipe for supplying oxygen to the patient P and exhausting exhaled gas from the patient P.

The aforementioned inhale gas supply unit 62 has a blender 621 for mixing oxygen with the atmosphere, and a humidifier 622 for humidifying the air to be sent out from the blender 621. The humidifier 622 is connected to an inhale pipe 623 for supplying the humidified gas to the patient P. The inhale pipe communicates with a pressurized chamber 563 of the diaphragm unit 56 and is connected to an inhale end pipe 605 via a three-way branched pipe 7. A pressure sensor 624 is mounted on the inhale end pipe 605 for detecting an inhale state of the patient P. Moreover, the three-way branched pipe 7 has an exhaust pipe 604 for exhausting the exhaled gas.

The diaphragm unit 56 includes a pressurizing chamber, a pressurized chamber, and a diaphragm 561 made from an expandable member to isolate the pressurizing chamber 561 from the pressurized chamber. The pressurizing chamber is connected via the oscillating air pressure pipe 545 to the oscillating air pressure generator 20.

Furthermore, this oscillating air pressure generator 20 is connected to the blower 52 via a positive pressure pipe 521 and a negative pressure pipe 522. The blower 522 takes in air from the negative pressure pipe 522 and discharges the air through the positive pressure pipe 521.

Figure 25:
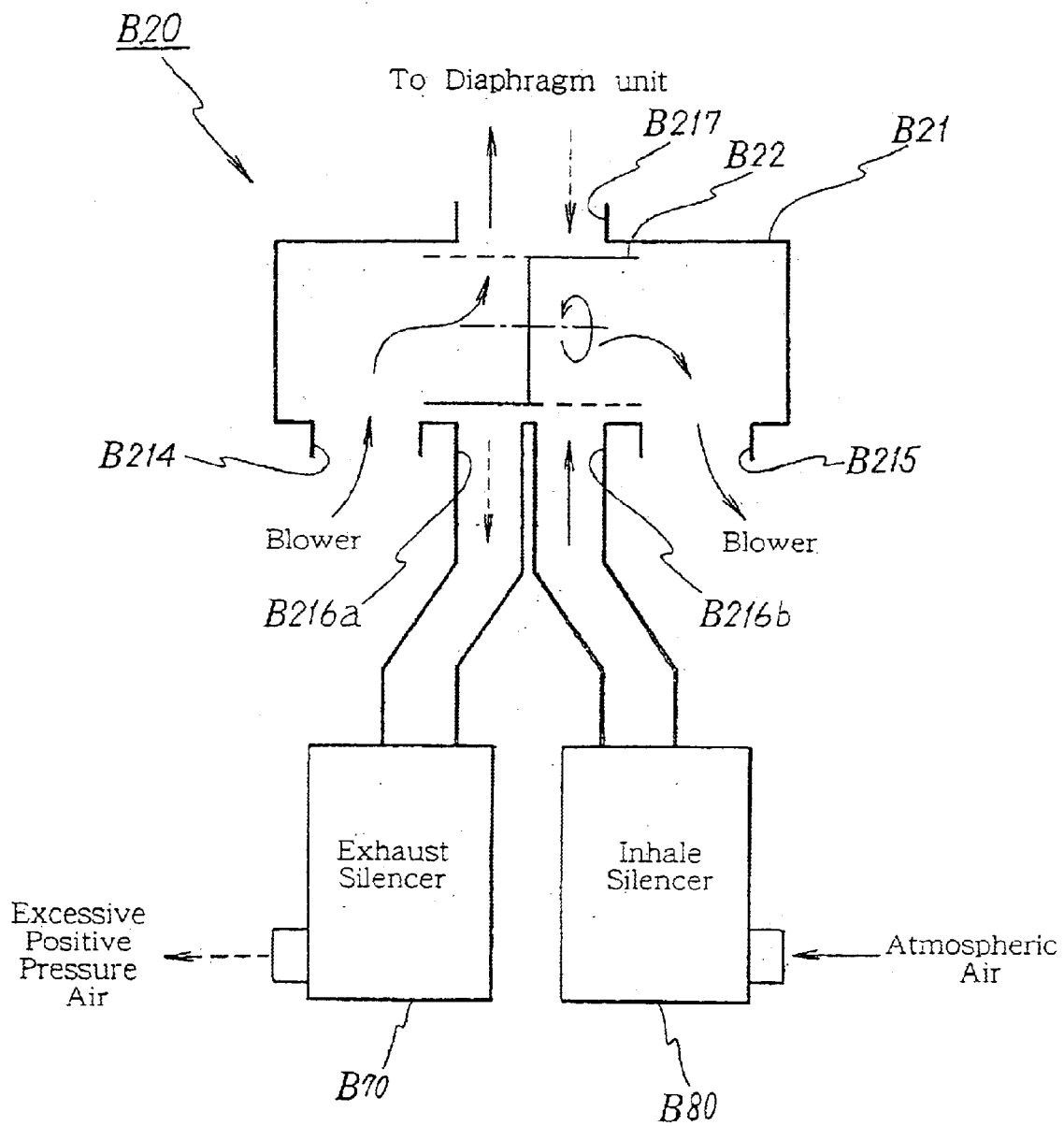
FIG. 25 is a block diagram of the oscillating air pressure generator having two silencers: an exhaust silencer for exhausting gas and an inhale silencer for inhaling gas.

FIG. 25 schematically shows the oscillating air pressure generator B20 mounted on the high-frequency artificial respiration apparatus 12. The oscillating air pressure mechanism 20 includes: a frame 21 having a positive pressure input port B214 which is supplied with positive pressure from the blower B52, a negative pressure input port B215 supplied with a negative pressure from the blower B52, atmospheric ports B216a and B216b open to the atmosphere, and an output port for outputting an oscillating air pressure; a switching valve member 22; and a drive unit for continuously urging the switching operation of the switching valve member 22. The switching valve member 22 selective switches between a first connection state and a second connection state. In the first connection state, the positive pressure input port B14 is connected to the output port B21, and the negative pressure input port B215 is connected to the atmospheric port B216b. In the second connection state, the positive input port B214 is connected to the atmospheric port B216a, and the negative pressure input port B215 is connected to the output port B217.

The switching valve member is a valve switch rotatably mounted on the frame B21 for switching between the aforementioned first connection state (indicated by an a solid line arrow) and the second connection state (indicated by a dotted line arrow). These connections are alternately established, so that an oscillating air pressure is generated from the output port B217b at a periodicity identical to the rpm of the drive unit and at the atmospheric port, atmosphere is taken in and out at the same periodicity.

The atmospheric port B216a, when connected to the positive pressure input port B214, functions as an exit for exhausting excess positive pressure air. The atmospheric port B216b, when connected to the negative pressure input port B215, functions as an entrance for taking the atmosphere.

Moreover, the atmospheric port B216a has an exhaust silencer B70 arranged according to the frequency characteristic of noise generated here and the atmospheric port B216b has an inhale silencer B80 arranged according to the frequency characteristic of noise generated here.

Figure 26:
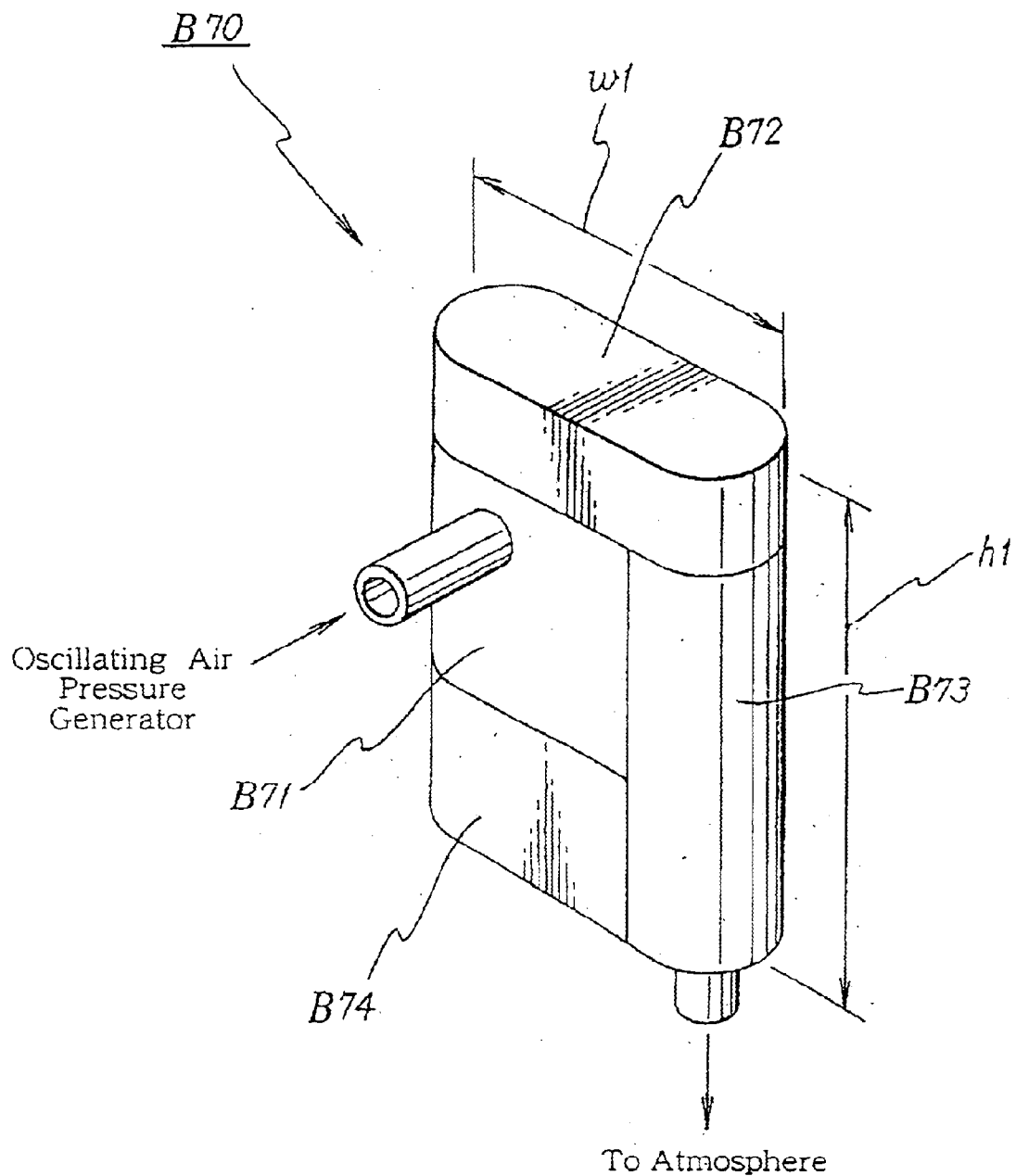
FIG. 26 is a perspective view of the exhaust silencer shown in FIG. 25.
Figure 27:
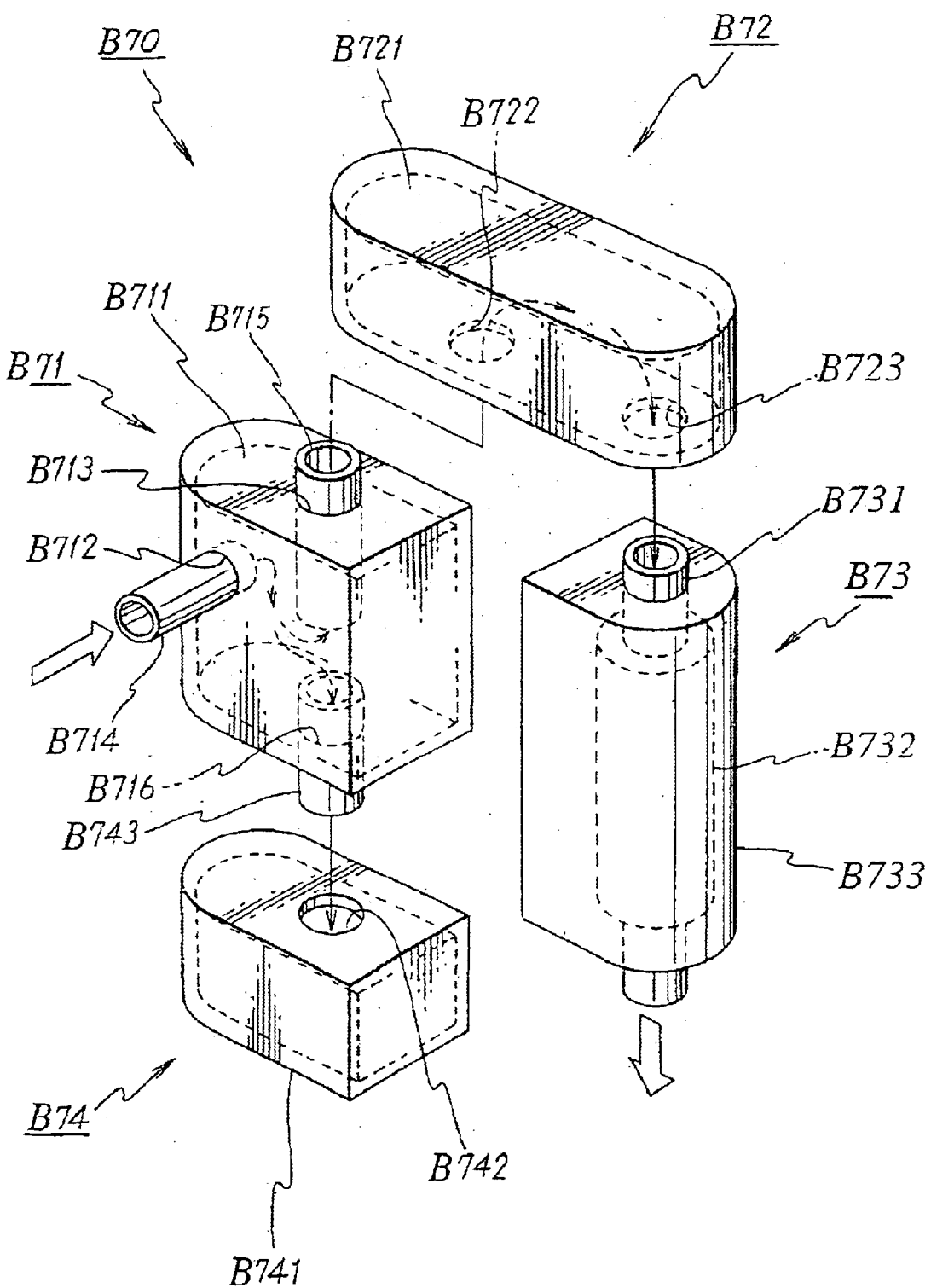
FIG. 27 is an exploded perspective view of the exhaust silencer.

FIG. 26 is a perspective view of an exhaust silencer B70. FIG. 27 is an exploded perspective view of the exhaust silencer B70. This exhaust silencer includes a first expansion chamber 71, a second expansion chamber 72, a sound absorbing path B73, and a resonance chamber B74. As an example, FIG. 26 shows the size of the exhaust silencer as an example: height h1=510 mm and width w1=175 mm.

The first expansion chamber is a closed container B711 having an entrance through hole B712 for a positive air pressure and an exit through hole B713. Similarly, the second expansion chamber is a closed container B721 having an entrance through hole B722 for the positive air pressure and an exit through hole B723.

The first expansion chamber has a pipe B714 inserted into the entrance B712. This pipe communicates inside and outside of the container B711. Similarly, a pipe B715 is inserted at the exit B713.

The pipe B714 has the upstream end connected to the atmospheric port B216a. A portion of the pipe B715 protruding outside is inserted into the entrance through hole B722 provided in the wall of the container B721.

Thus, the positive pressure air is introduced from the entrance B712 into the container B711 and discharged from the exit B713 into the second expansion chamber B72.

Moreover, the first expansion chamber B71 is arranged adjacent to the resonance chamber B74. This resonance chamber is constituted by a container B741 having a communication hole B742 for communication with inside of the container B711 of the first expansion chamber B71.

The container B711 of the first expansion chamber B71 has a through hole 716 corresponding to the communication hole 742. A pipe B743 is inserted into the communication hole B742 and the through hole B716. Accordingly, with this pipe B743, the first expansion chamber B71 communicates with the resonance chamber B74. The positive pressure air introduced into the resonance chamber B74 stays there.

On the other hand, the exit of the second expansion chamber B72 is connected to the sound-absorbing path. Accordingly, the positive pressure air sent from the first expansion chamber passes through the container B721 and flows into the sound absorbing path B73. The sound absorbing path includes a pipe B731 through which the positive pressure air passes, a sound absorbing material B732 surrounding the pipe 731, and a frame B733 containing the sound absorbing material B732.

The sound absorbing material B732 may be a foam material made from a resin containing foaming agent (such as polyurethane sponge and foamed styrol) or a material which can easily contain air inside (such as cotton and layered cloths).

Moreover, the pipe B731 protrudes from the upper surface and the lower surface of the frame B733. The upper protrusion is inserted into the exit B723 of the second expansion chamber B72. The positive pressure air which has passed through the second expansion chamber B72 further passes through the pipe B731 and exhausted outside into the atmosphere.

Figure 28:
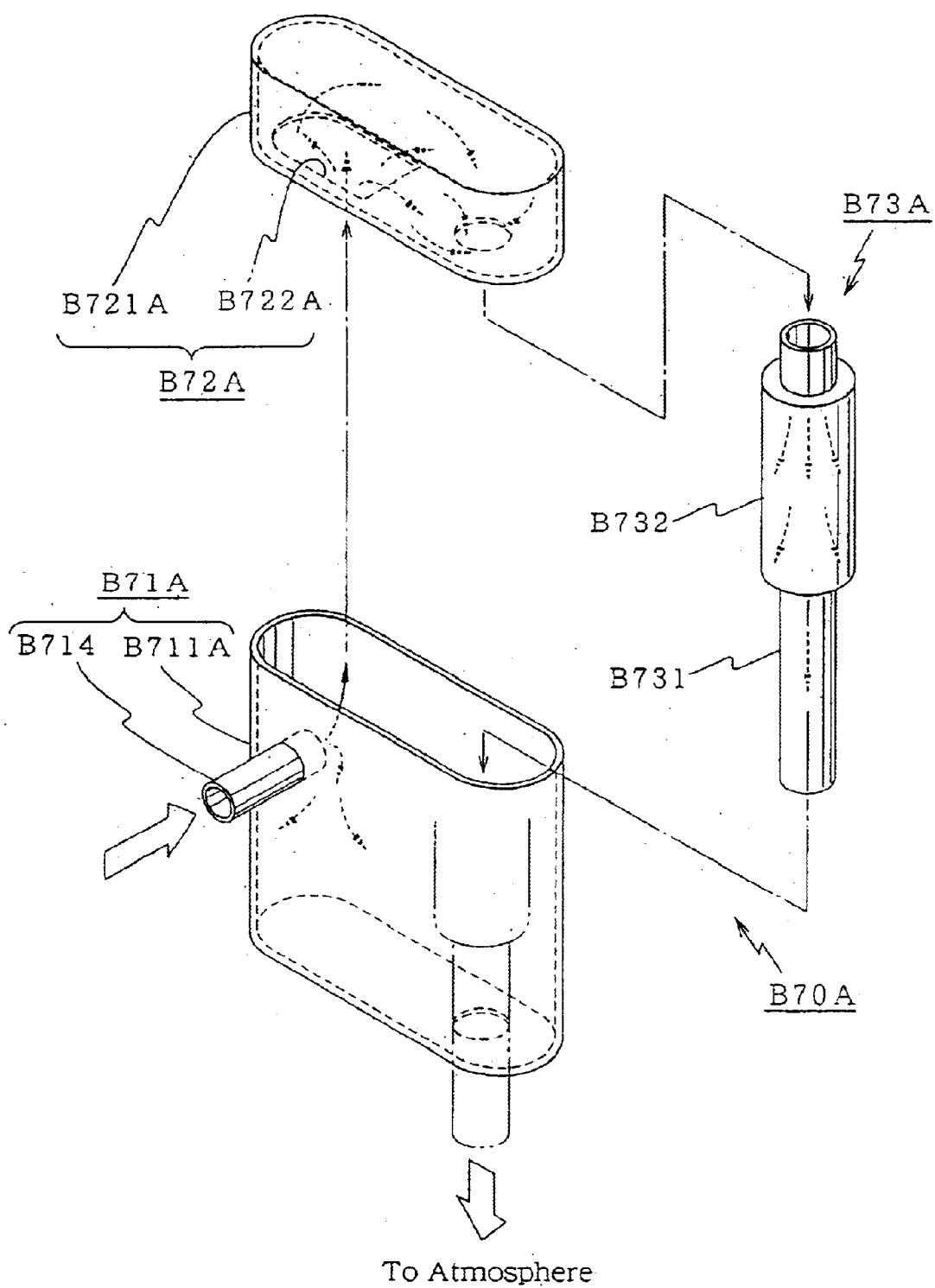
FIG. 28 is an exploded perspective view of another (second) example of the exhaust silencer.

FIG. 28 shows another example of the exhaust silencer. The exhaust silencer B70A shown in FIG. 28 includes a first expansion chamber B71A, a second expansion chamber B72A, and a sound absorbing path B73A. This silencer is different from the aforementioned silencer B70 in that no resonance chamber B74 is provided.

The first expansion chamber B71A is constituted by a container B711 having an open top which is closed by a bottom of the container B721A of the second expansion chamber B72A. Moreover, the container B711A of the first expansion chamber B71AS communicates with the container 721A of the second expansion chamber through a through hole provided in the bottom of the container B721A.

Furthermore, the sound absorbing path B73A has no frame B733 and has only a pipe B731 and a sound absorbing material B732 which are mounted directly inside the container B711A of the first expansion chamber B71A.

As will be detailed later, the resonance chamber B74 has an effect to reduce a low sound pressure level in the order of 80 to 200 Hz. Accordingly, the noise generated during exhaust is in the aforementioned noise level 80 to 200 Hz, this exhaust silencer B70A can sufficiently lower the noise.

Figure 29:
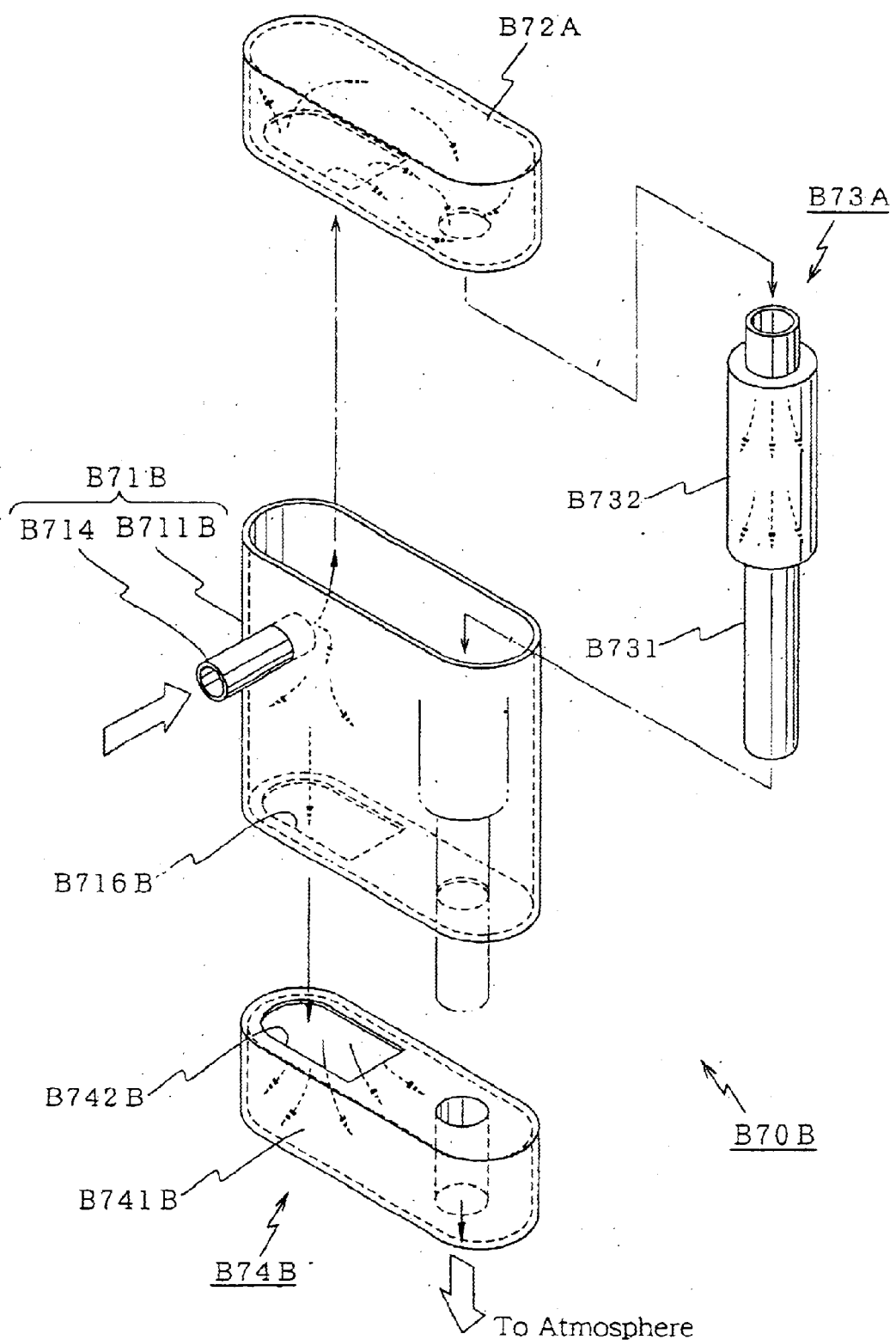
FIG. 29 is an exploded perspective view of still another (third)) example of the exhaust silencer.

The exhaust silencer B70B shown in FIG. 29 includes a first expansion chamber B71B, a second expansion chamber B72A, a sound absorbing path B73A, and a resonance chamber B74B. Like components as in the exhaust silencers B70 and B70B are denoted by the same reference symbols and their explanations will be omitted.

The first expansion chamber B71B includes a container 711B whose top is open and covered by the bottom of the container B721A of the second expansion chamber B72A. Moreover, the container B771A of the second expansion chamber B72A communicates with the container B721A of the second expansion chamber B72A through a through hole serving as an entrance B722A.

Moreover, the first expansion chamber B71B is adjacent to and communicate with the resonance chamber B74B through a through hole B716B provided in the container B711B and a communication hole provided in the container B741B.

Furthermore, the sound absorbing path B73A includes a pipe B731 and a sound absorbing material B732 having no frame and extends to the interior of the container B711A of the first expansion chamber B71A and the container B741B of the resonance chamber B74B.

The exhaust silencer B70B has almost identical configuration as the exhaust silencer B70 and exhibits similar effects.

Figure 30:
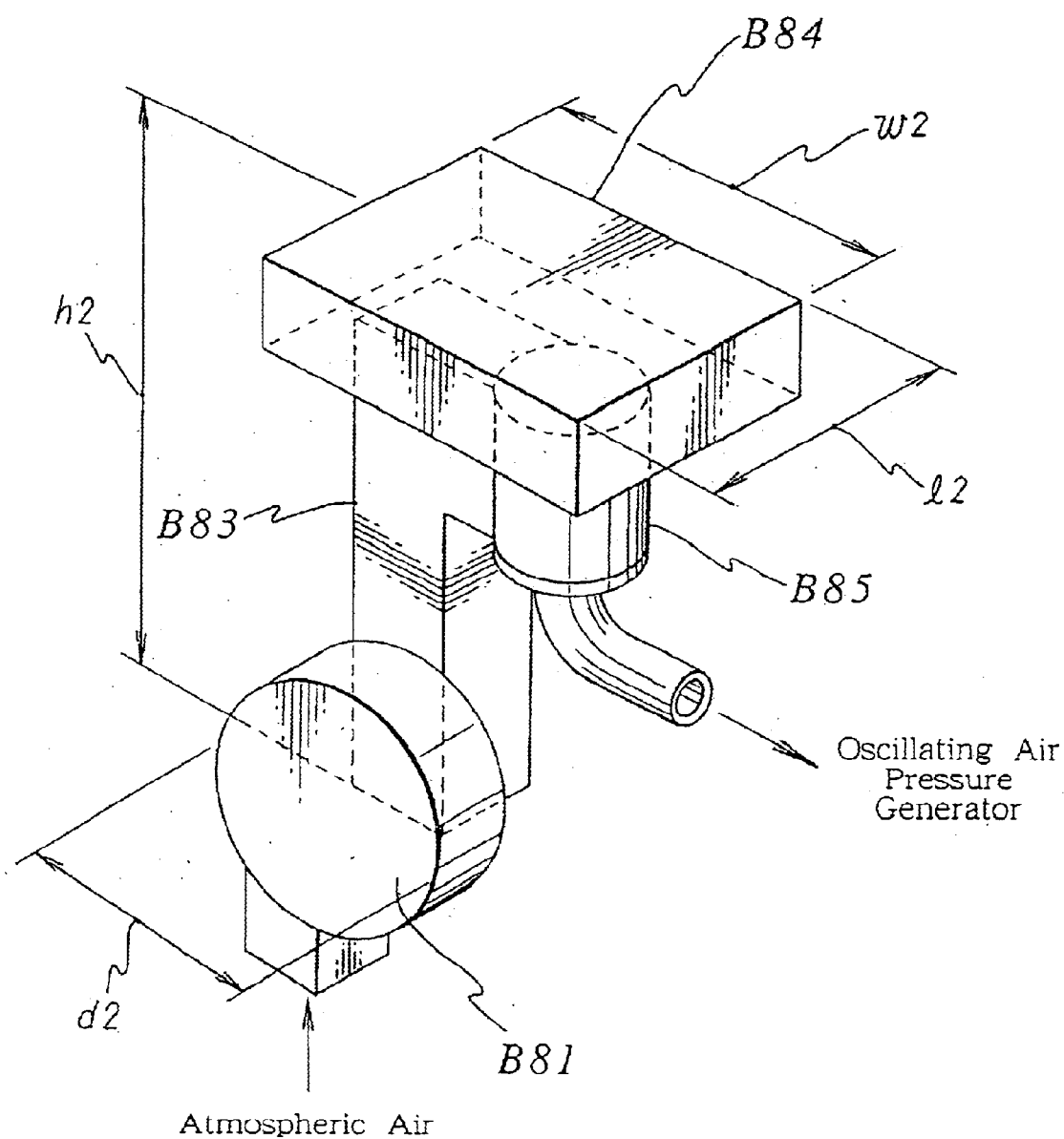
FIG. 30 is a perspective view of the inhale silencer shown in FIG. 25.
Figure 31:
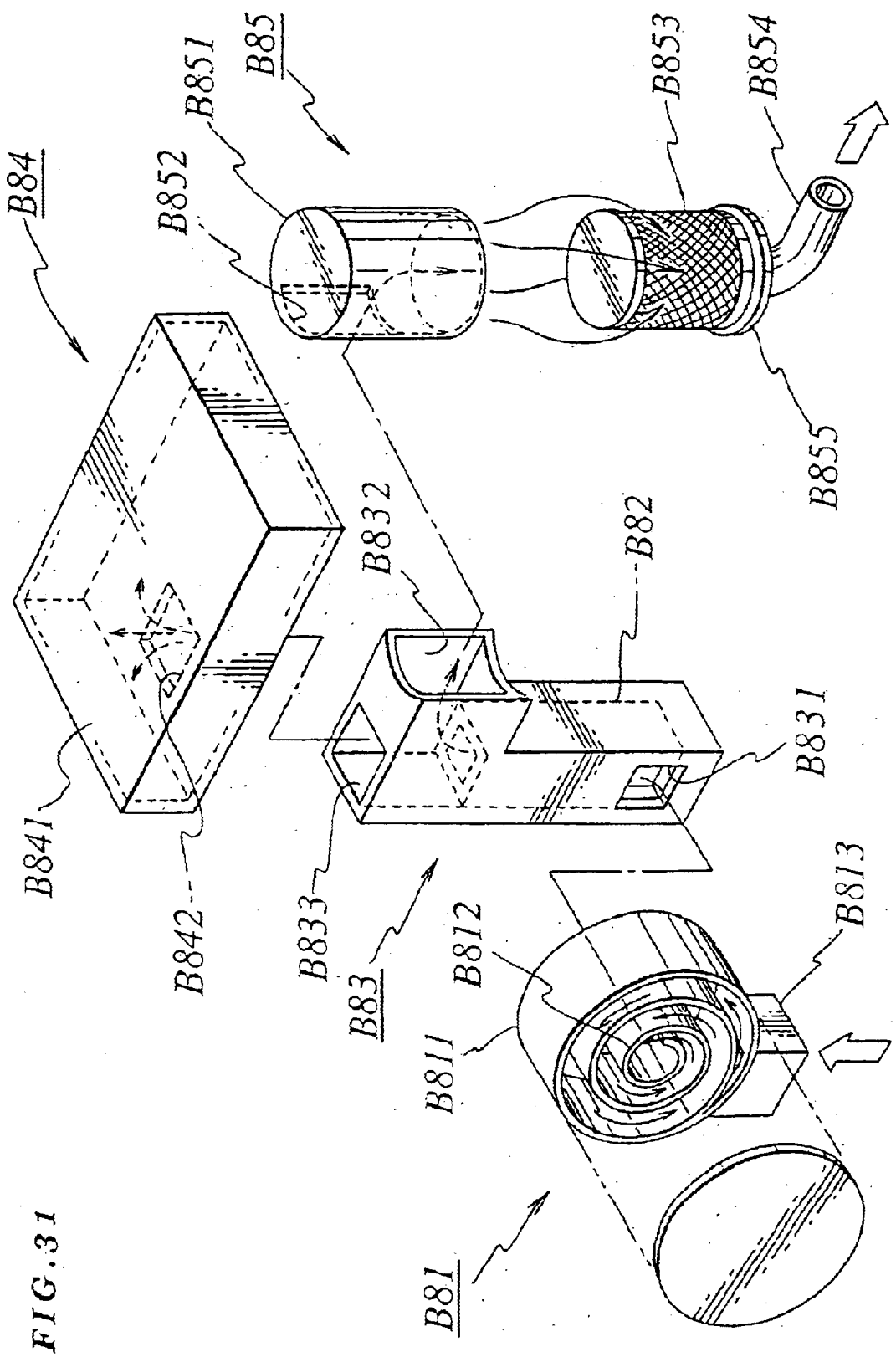
FIG. 31 is an exploded perspective view of the inhale silencer.
Figure 32A:
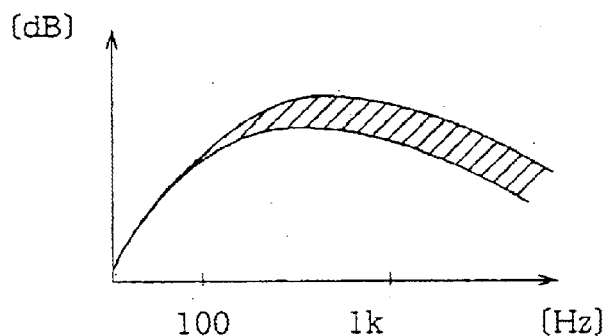
FIG. 32(A) shows a frequency characteristic of noise reduction in an expansion chamber.
Figure 32B:
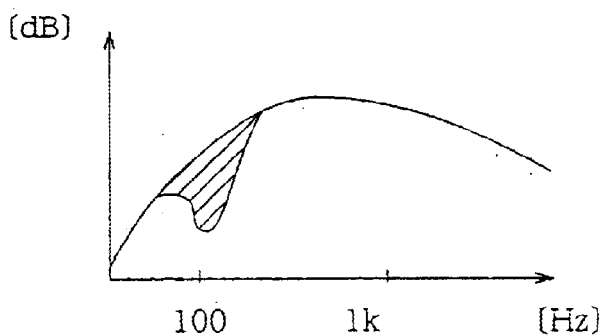
FIG. 32(B) shows a frequency characteristic of noise reduction in a resonance chamber.
Figure 32C:
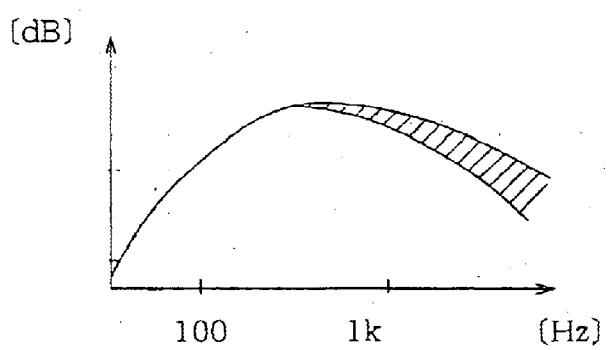
FIG. 32(C) shows a frequency characteristic of noise reduction in a sound suction flow path.

FIG. 30 is a perspective view of a suction silencer B80, and FIG. 31 is an exploded perspective view of the suction silencer B80. This suction silencer B80 includes a spiral flow path member B81, an inverted L-shaped pipe B83 having a sound absorbing path B82, a resonance chamber 84, and an air filter 85. FIG. 30 roughly shows dimensions of this suction silencer B80: h2=437 mm, w2=275 mm, l(length) 2=215 mm, and d2=200 mm.

As shown in FIG. 31, the spiral flow path member B81 includes a cylindrical frame B811 and a spiral wall B812 provided in the frame B811. The frame B811 has an atmosphere take-in hole B813. Moreover, the frame B811 has an external wall having an exit (not depicted). This exit communicates with the pipe B83. Thus, the atmosphere taken into the spiral flow path member B81 through the atmosphere take-in hole B813 advances along the spiral wall and, reaching the exit, flows into the pipe B83.

In the spiral flow path member B81, the spiral wall should have sufficient length in comparison to the width. As the length increases with respect to the width, it is possible to obtain a higher sound absorbing effect. However, considering the flow loss at the atmosphere take-in, it is preferable to set the length 20 to 40 times of the width of the spiral wall.

The pipe B83 has an entrance B831 at one end and an exit B832 at the other end. The entrance B831 is connected to the exit of the spiral flow path member B812. The exit B832 is connected to the air filter B85.

The pipe B83 has a sound absorbing flow path B82 at the side of entrance B831. This sound absorbing flow path B82 is made from a sound absorbing material where the atmosphere flows. This sound absorbing material may be the aforementioned material. Furthermore, the pipe B83 has a through hole B833 which is connected to a communication hole B842 of the resonance chamber B84.

The resonance chamber includes a container B841 as a closed space adjacent to the pipe B83, and a communication hole B842 for communicating with the pipe B83.

Through the communication hole B842 and the through hole B833, the pipe B83 communicates with the resonance chamber B84. Thus, the atmosphere stays inside the container B841.

The air filter includes a cylindrical cover B851 having no bottom, an entrance B852 provided on this cover B851, a lid member B855 to close the bottom of the cover B851, an exit B854 provided in this lid member B855, and a cylindrical mesh filter member B854 provided on the lid member B855. The mesh filter member B853 maybe made from a cloth which is arranged on the lid member B855 so as to cover the exit B854.

The atmosphere which has entered from the entrance B852 passes through the mesh filter member B853 and flows out from the exit B854. A certain clearance is present between the inner surface of the cover B851 and the mesh filter member B853. The atmosphere taken in passes through the clearance and the mesh filter member B853, so that dusts contained is removed and the noise level is lowered.

Moreover, the exit B854 is connected to the atmospheric port B216$b$ of the oscillating air pressure generator B20. Thus, a clean atmosphere is sucked by the oscillating air pressure generator.

In the aforementioned exhaust silencer B70, the expansion chambers B71 and B72 have an effect to lower the sound pressure level of the noise of the almost entire range (100 to 4000 Hz). This has been assured by the test (see FIG. 32A).

In the aforementioned exhaust silencer B70 or the suction silencer B80, the resonance chambers B74 and B84 have an effect to lower the sound pressure level of the noise of a low frequency (80 to 200 Hz). This has been assured by the test (see FIG. 32B).

The exhaust silencer B70 and the suction silencer B80 having the sound absorbing paths B732 and B82, respectively, have an effect to reduce a high frequency sound (500 to 5000 Hz). This has been assured by a test (see FIG. 32 (C)).

The spiral flow path member B811 mounted on the suction silencer B80 can reduce the sound pressure level over the entire range (100 to 4000 Hz).

Figure 33:
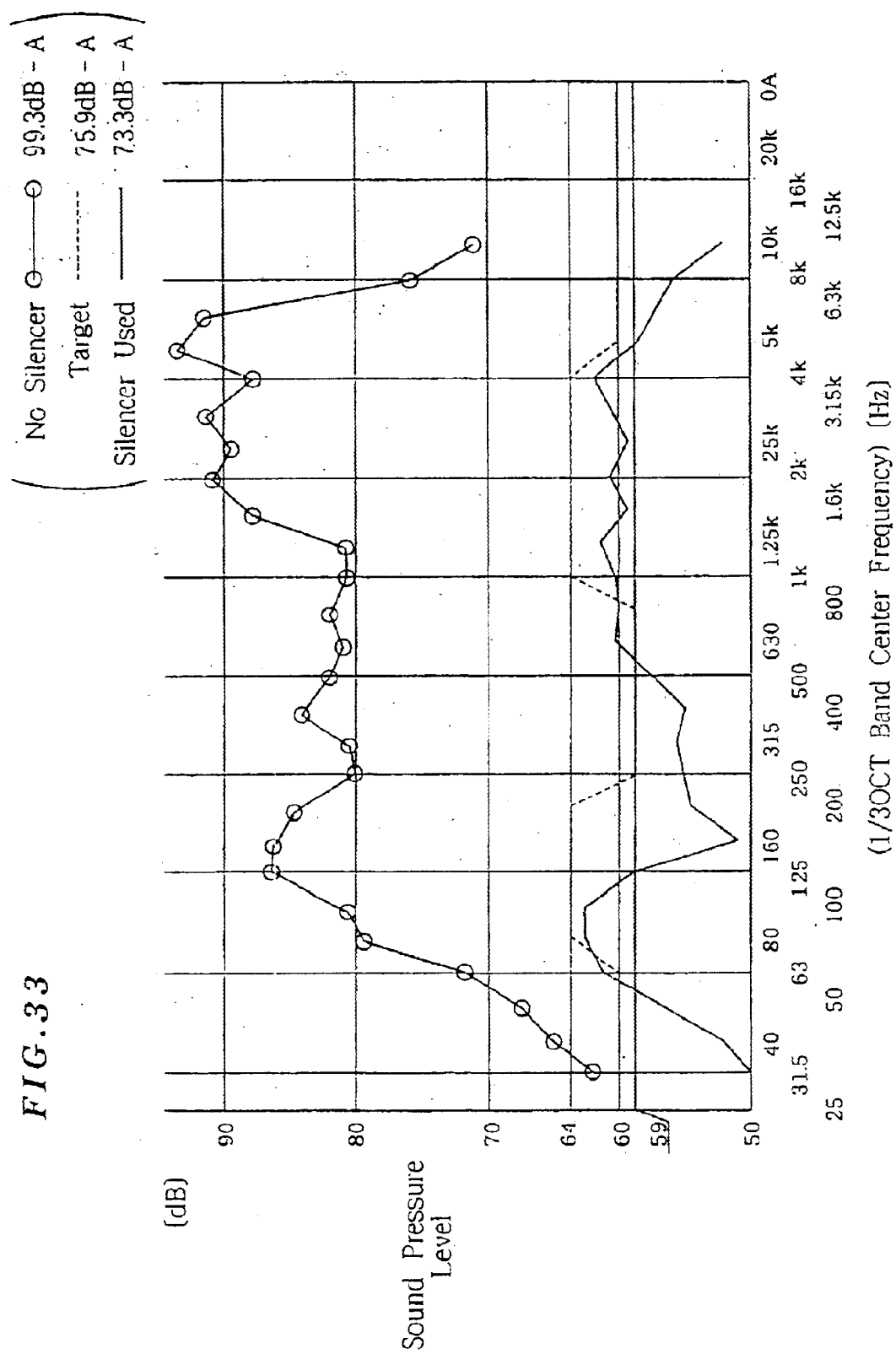
FIG. 33 shows frequency characteristics of the noise generated at the exhaust hole and the noise reduced by the exhaust silencer.

FIG. 33 shows sound pressure level characteristic for the respective frequencies when using and not using the aforementioned exhaust silencer B70. As shown here, when the exhaust silencer B70 is not used, the sound pressure levels increases especially around 125 Hz and 5000 Hz. In contrast to this, when the exhaust silencer B70 is used, the sound pressure level is sufficiently reduced over the entire range.

Figure 34:
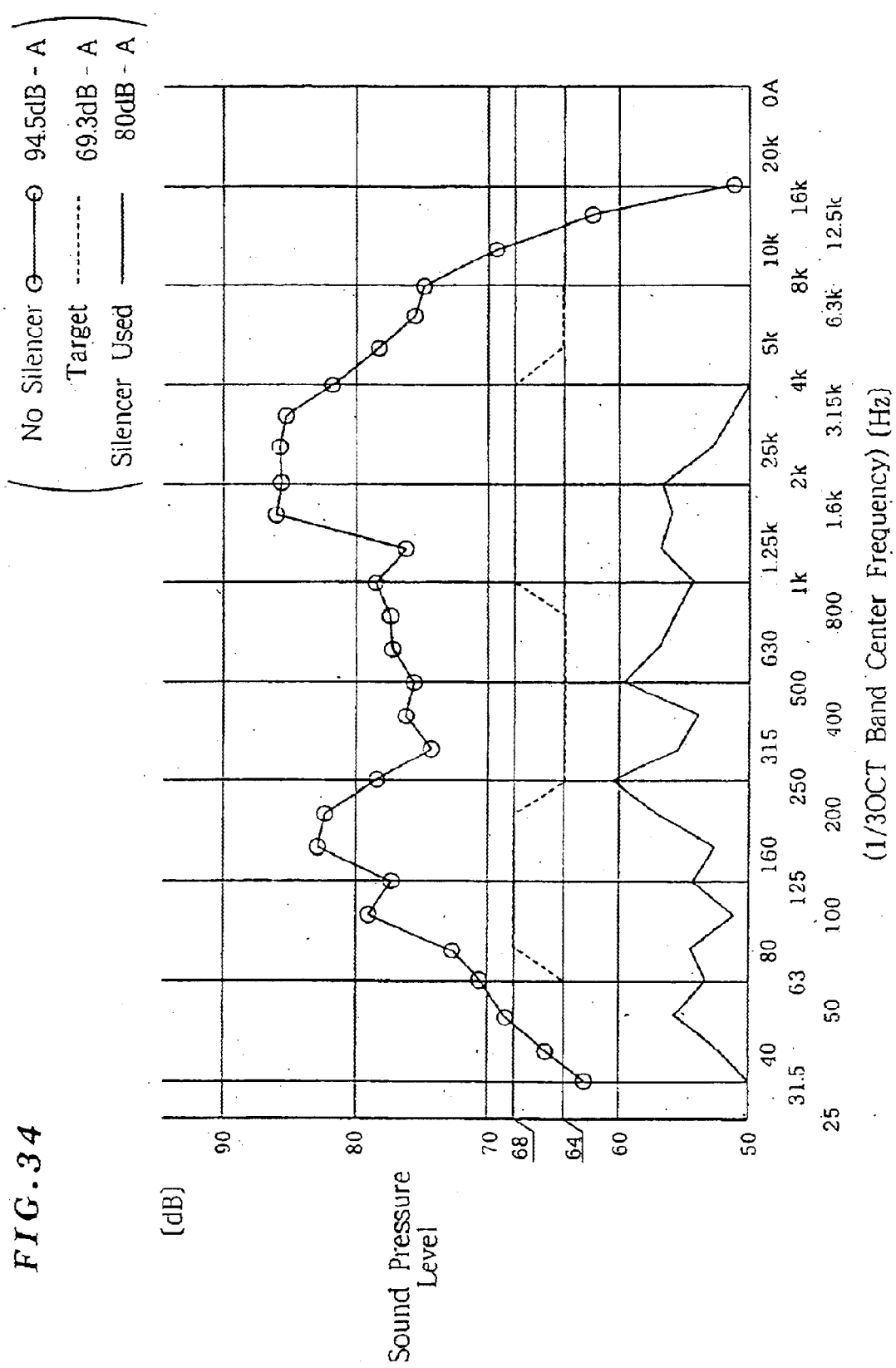
FIG. 34 shows frequency characteristics of the noise generated at the inhale hole and the noise reduced by the inhale silencer.

FIG. 34 shows sound pressure level characteristic for the respective frequencies when using and not using the aforementioned suction silencer B80. As shown here, when the suction silencer B80 is not used, the sound pressure level increases especially around 160 Hz and 2500 Hz. In contrast to this, when the suction silencer B80 is used, the sound pressure level is sufficiently reduced over the entire range.

Thus, when the atmospheric port of the oscillating air pressure generator 20 is divided into two ports one for the positive pressure exhaust and the other for air take-in, and each of the atmospheric ports B216$a$ and B216$b$ is provided with the exhaust silencer B70 and the suction silencer B80, respectively, it is possible to reduce the noise of two frequency characteristics, thus enabling to effectively reduce the noise of the oscillating air pressure generator B20.

Moreover, the exhaust silencer B70 has a combination of the expansion chambers B71 and B72, the sound absorbing path B73, and the resonance chamber B74, and can reduce the sound pressure levels of the respective frequency bands, so as to effectively reduce the noise generated from the atmospheric port B216$a$.

Moreover, the suction silencer B80 has a combination of the spiral flow path member B81, the sound absorbing path B83, and the resonance chamber B84, and can reduce the sound pressure levels of the respective frequency bands, so as to effectively reduce the noise generated from the atmospheric port B216b.

Furthermore, oscillating air pressure generator B20 has two atmospheric ports, one for the positive pressure exhaust and the other for air take-in and each of the ports has a dedicated silencer. Thus, the position for exhausting an excess positive pressure and the position for taking air in are separated from each other. This prevent the positive pressure air of a high temperature from being sent to the blower B52. This significantly increases the service life of the blower B52.

Next, explanation will be given on the entire operation of the artificial respiration apparatus B12. The inhale gas supply unit starts supplying inhale gas (oxygen) and the blower B52 starts to be driven. The positive and negative pressures generated by the blower B52 are converted into an oscillating air pressure by the oscillating air pressure generator B20. The oscillating air pressure is sent to the diaphragm unit B56. In the diaphragm unit B56, the diaphragm B561 is oscillated at the periodicity of the oscillating air pressure. The oscillation of the diaphragm B561 changes the pressure inside the inhale pipe B623.

Accordingly, the inhale gas passing through the inhale pipe B6223 is subjected to the oscillating air pressure so as to reach lungs of a patient who cannot breath by himself/hersel. Thus, oxygen in the inhale gas reaches his/her lungs. Moreover, the inhale gas supplied reaches the patient's lungs while being oscillated. Moreover, the exhale gas containing carbon dioxide advances in the inhale end pipe B605 in the opposite direction to the inhale gas, so as to be exhausted from the exhaust pipe B604. Here, in the inhale end pipe, the inhale gas and the exhaled gas advance in the opposite directions in the same inhale end pipe. This is enabled by the three-way branched pipe B7 as a guide to divide the interior into an inhale region and exhale region.

Embodiment 3

Description will now be directed to an artificial respiration apparatus according to the third embodiment of the present invention. This artificial respiration apparatus C12 is based on a high-frequency oscillating (HDO) ventilation method.

Figure 35:
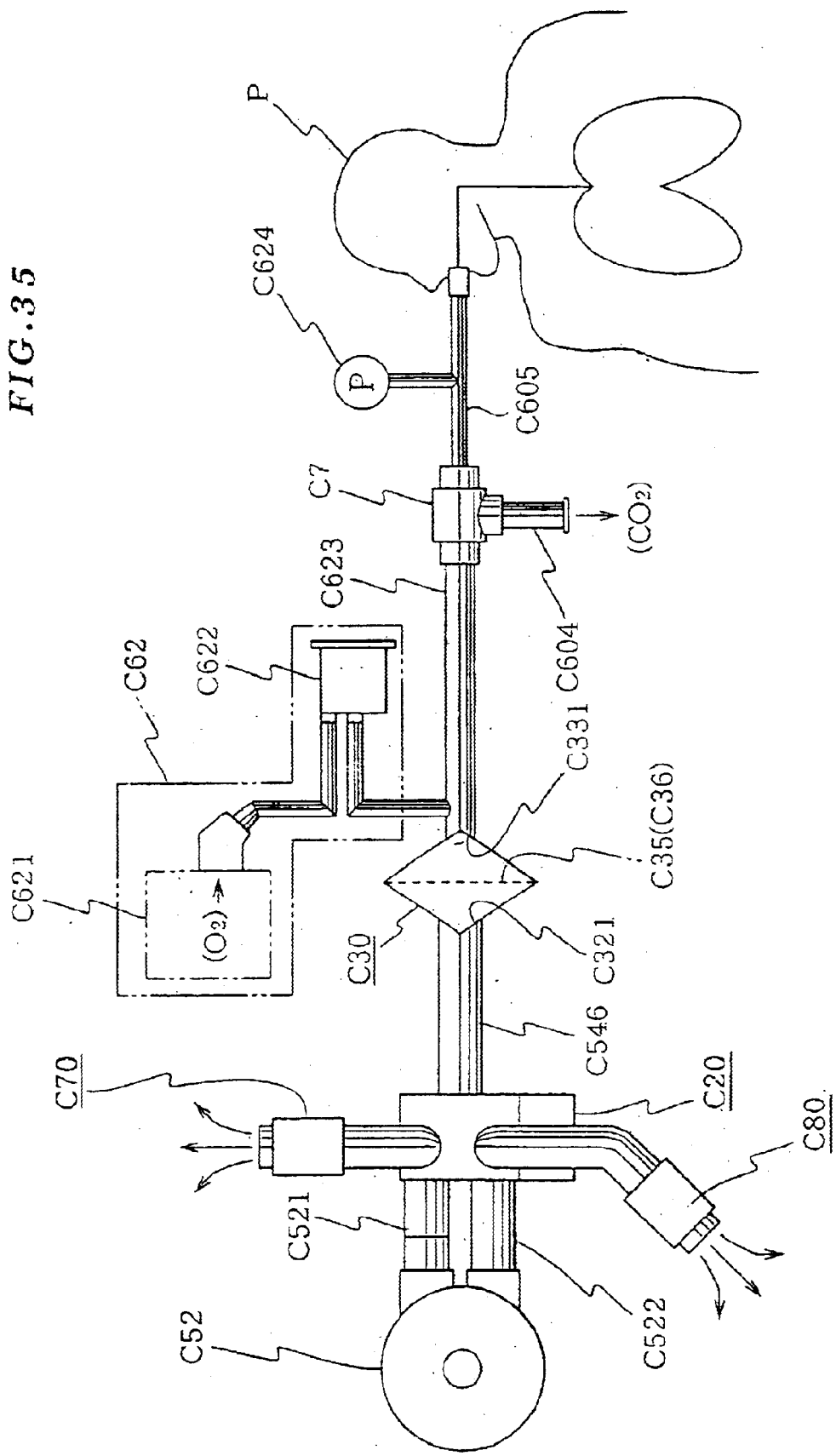
FIG. 35 shows an artificial respiration apparatus according to a third embodiment of the present invention.

As shown in FIG. 35, the artificial respiration apparatus C12 includes: an inhale gas supply unit C62 as an oxygen supply source; a blower (air pressure supplier) C52; an oscillating air pressure generator C20 for alternately selecting the positive pressure and negative pressure generated by the blower C52 so as to be converted into a predetermined oscillating air pressure; a diaphragm unit urged to operate by the oscillating air pressure from the oscillating air pressure generator C20, so as to apply the oscillating air pressure to the oxygen (oxygen mixed with air) to be supplied from the inhale gas supply unit C62 to a patient P; an exhaust silencer C70 mounted on the oscillating air pressure generator C20 and an inhale silencer C80; and a pipe for supplying oxygen and exhausting exhaled gas to/from the patient.

The aforementioned inhale gas supply unit C62 includes a blender for mixing the oxygen with the atmospheric air and a humidifier C622 for humidifying the gas sent from the blender C621. The humidifier C622 is connected to an inhale pipe C623 for supplying to a patient the inhale which has passed through the humidifier. The inhale pipe C623 communicates with an output hole C331 of the diaphragm unit C30 and is also connected via the three-way branched pipe C7 to the inhale end pipe C605, reaching the patient P. In the middle of the inhale end pipe, there is provided a pressure sensor mounted for detecting exhale state of the patient P. Moreover, the three way branched pipe C7 includes an exhaust pipe C604 for exhausting the exhaled gas.

The input hole C321 of the diaphragm unit C30 is connected via the oscillating air pressure pipe C546 to the oscillating air pressure generator C20. Furthermore, the oscillating air pressure generator C20 is connected via the positive pressure pipe C521 and the negative pressure pipe C522 to the blower C52. This blower C52 takes air from the negative pressure pipe C522 and discharges the air from the positive pressure pipe C521.

Figure 36:
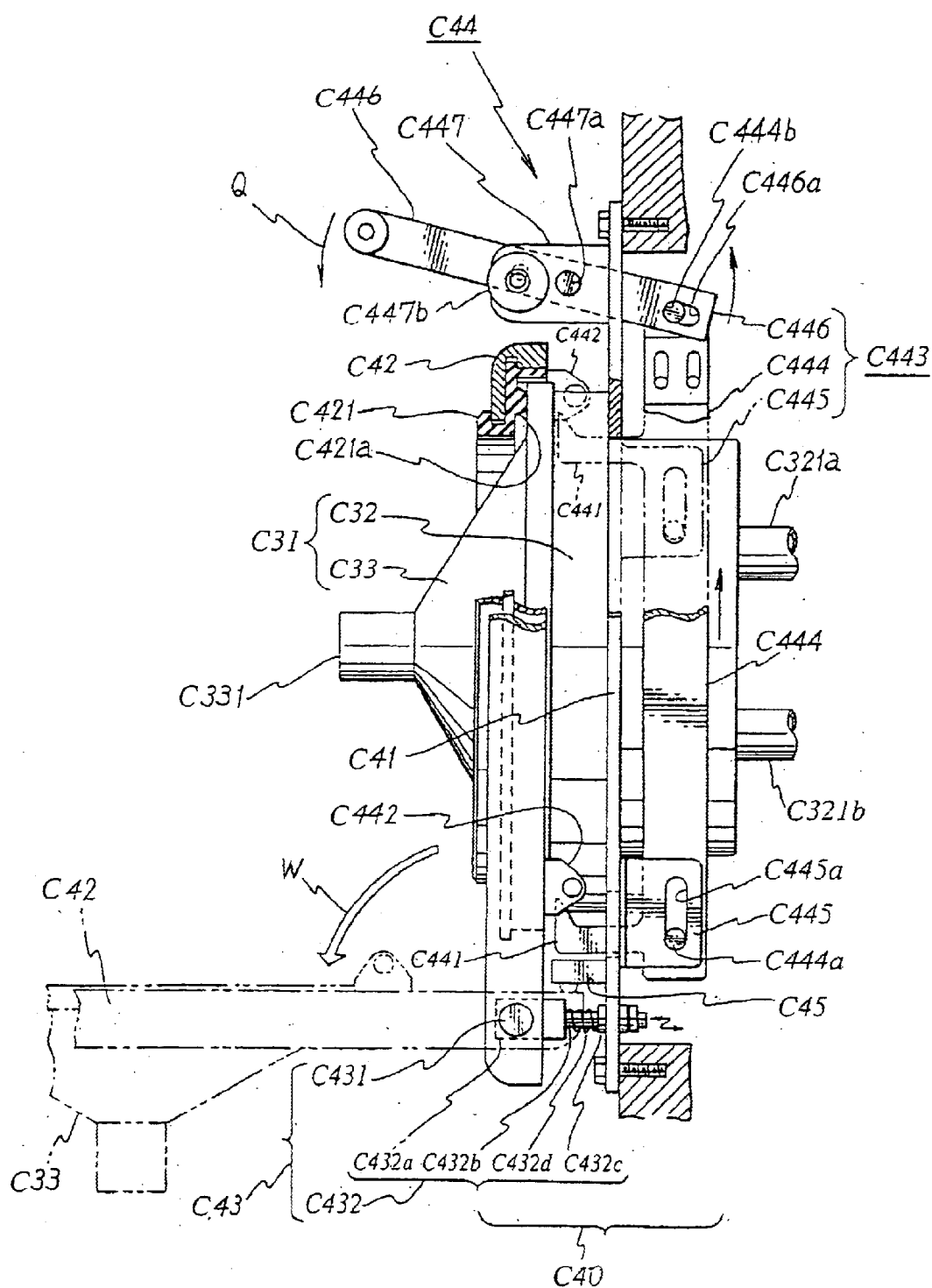
FIG. 36 a front view of a diaphragm in FIG. 35 partially cut away.

Here, explanation will be given on the diaphragm unit C30 with reference to FIG. 36 through FIG. 42. FIG. 36 is a front view showing the entire configuration of the diaphragm unit C30. The diaphragm unit C30 includes: a container body C31 constituted by a first diaphragm section having the input holes C321a and C321b and a second diaphragm section having the output hole C331; a support mechanism for supporting the connection state; and two diaphragm films C35 and C36 sandwiched by the first diaphragm section C32 and the second diaphragm section C33.

Hereinafter, a detailed explanation will be given on the respective components of the diaphragm unit.

Figure 37:
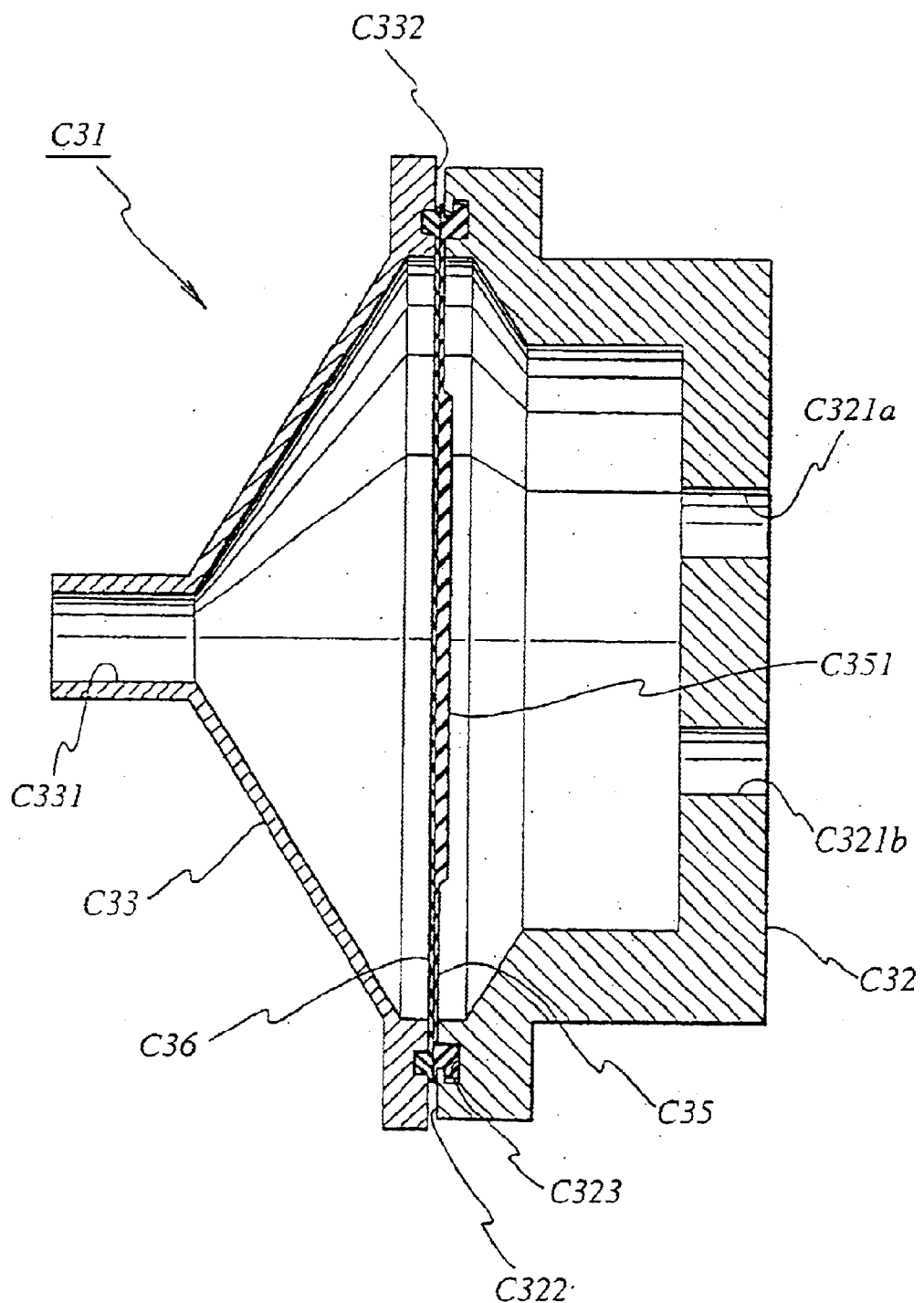
FIG. 37 is a cross sectional view along the center line of the diaphragm unit having two diaphragm films.
Figure 38:
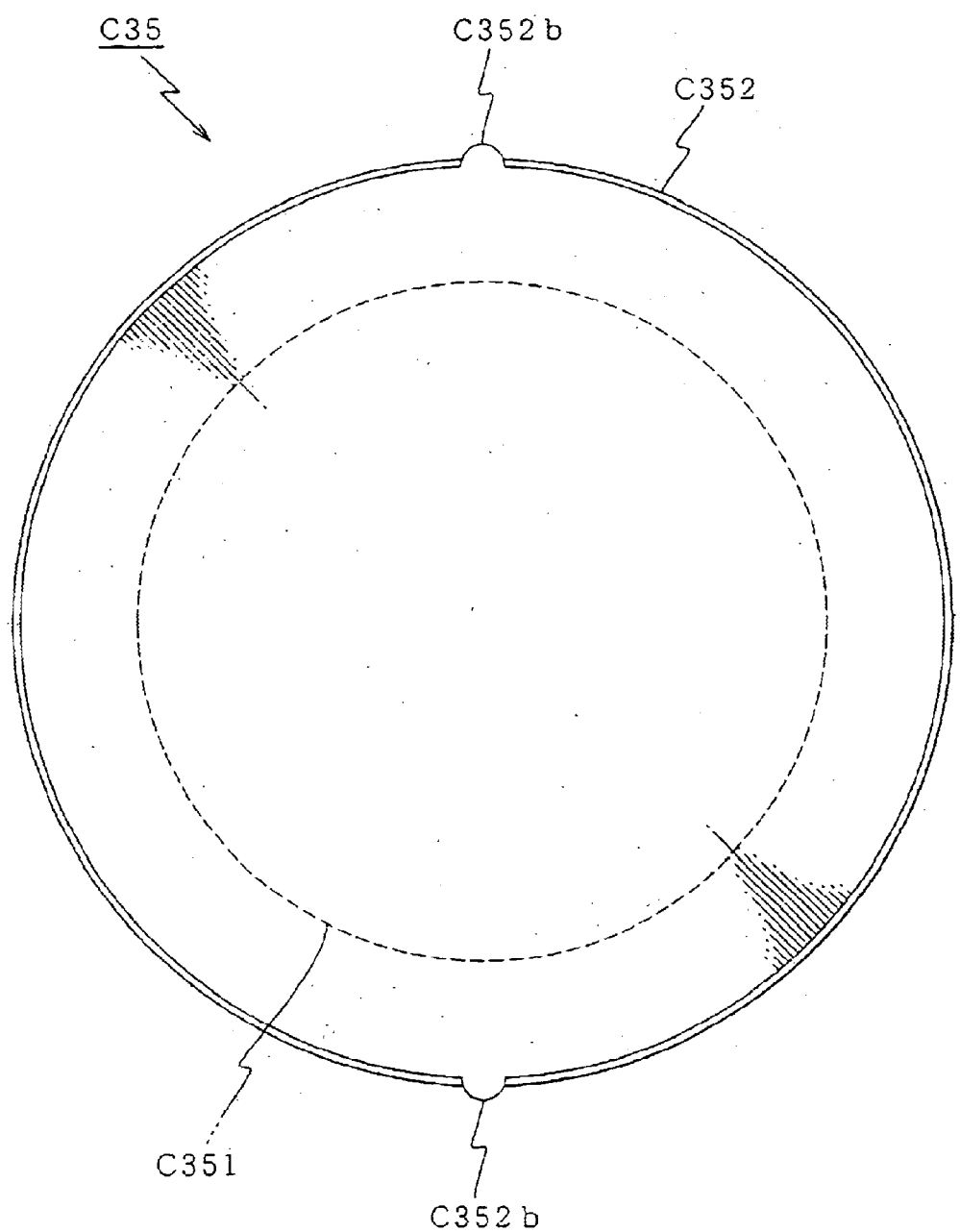
FIG. 38 shows a (first) diaphragm film viewed from the other (second) diaphragm film.
Figure 39:
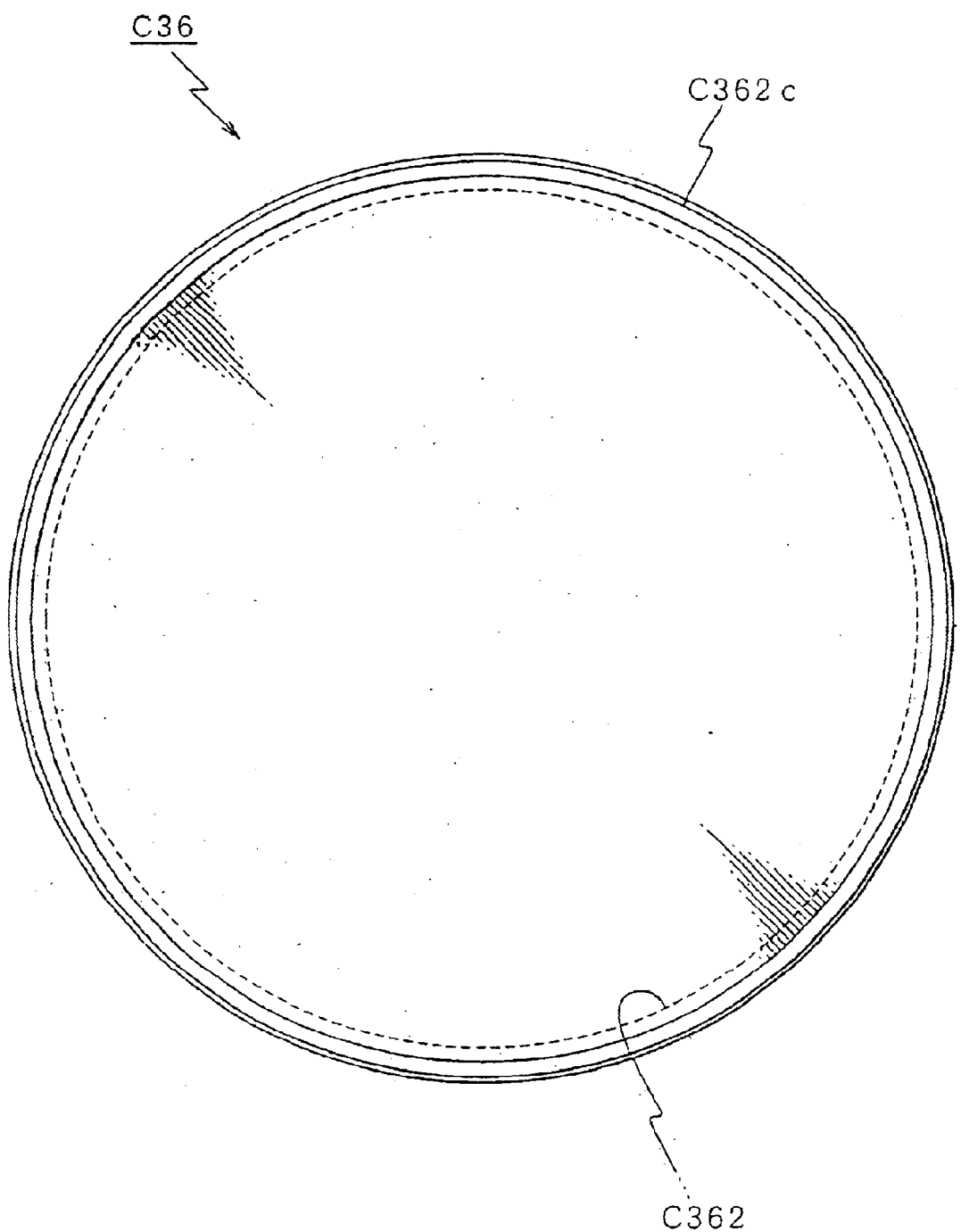
FIG. 39 shows the second diaphragm film viewed from the first diaphragm film.

FIG. 37 is a cross sectional view of the container body having the diaphragm films C35 and C36. Moreover, FIG. 38 shows the diaphragm C35 viewed from the diaphragm C36. FIG. 39 shows the diaphragm C36 viewed from the diaphragm C35.

As shown in FIG. 37, the first diaphragm section C32 is a body of revolution having one end wide open and the other end closed as a bottom. The bottom has a first input hole C321a through which a positive pressure gas is blown from the oscillating air pressure mechanism C20 and a second input hole C321b through which the inner gas is sucked by a negative pressure. Moreover, the open end circumference has a match plane C322.

On the other hand, the second diaphragm section C33 has a funnel shape having one end wide open and the other end has a small opening. This is the aforementioned output hole C331. The wide open end circumference has a match plane C332. This second match plane C332 is ring-shaped having a diameter almost identical to the first match plane C322. The first diaphragm section C32 and the second diaphragm section C33 are combined to form the container body C31 with their match planes C322 and C332 facing to each other.

Moreover, diaphragm films C35 and C36 are detachably mounted to close the wide openings of the first diaphragm section C32 and the second diaphragm section C33, respectively. The, the first and second diaphragm sections C32 and C33 are connected in such a manner that no clearance is present between the diaphragm films C35 and C36.

Each of the diaphragm films C35 and C36 is made from a thin rubber film (for example, 0.5 mm).

The diaphragm film C35 has a thicker (for example, 1.5 mm) portion C351 at the center. When the diaphragm film C35 is subjected to an oscillating air pressure, the thicker portion is entirely pushed forward, enabling to correctly transfer the oscillating air pressure. If there is no thicker portion, small irregular waves arise and cannot transfer the oscillating air pressure correctly. The thicker portion may be formed at the center of the other diaphragm film C36, or may be formed on both of the diaphragm films C35 and C36.

Furthermore, the outer circumference of the diaphragm film C35 has a ring-shaped flange portion C352 as an engagement member having a cross section identical to a mounting groove C323 formed at a position corresponding to the match plane C322. This flange portion C352 is formed unitarily with the diaphragm film at the side not facing the other diaphragm film. This flange portion includes a flange body C352a and removal tabs C352b. This diaphragm film C35 including the flange portion C352 having the flange body and the tabs are unitarily formed from rubber. The diaphragm film C35 is mounted by inserting the flange body C352a into the mounting groove C323.

Two removal tabs C352C are provided at the back of the flange portion C352 (in the opposite direction against the insert direction). The removal tabs C352 are arranged at two ends of a diameter of the diaphragm film C35. These two tabs are grasped when removing the diaphragm film C35 from the first diaphragm section C32.

Figure 40A:
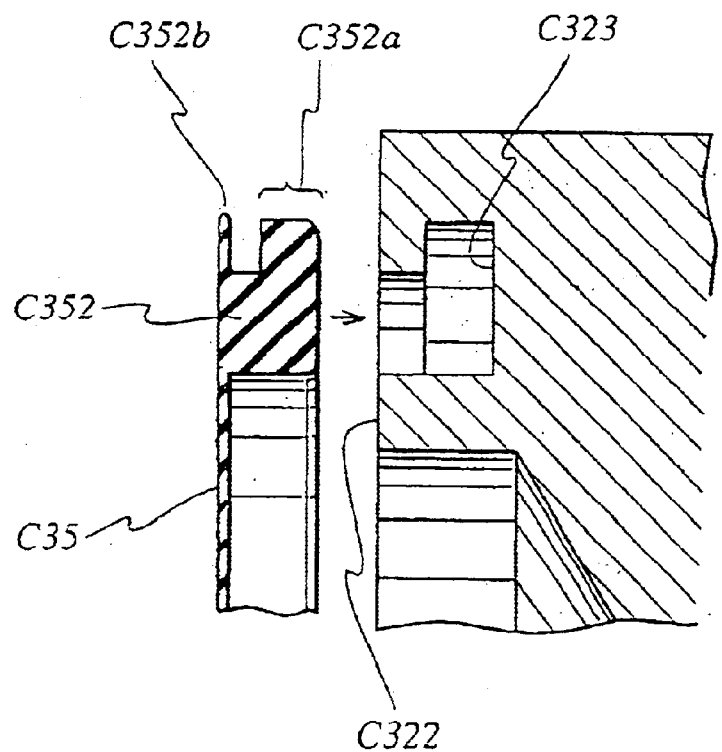
FIG. 40(A) shows a diaphragm mounting structure arranged in a first partition.
Figure 40B:
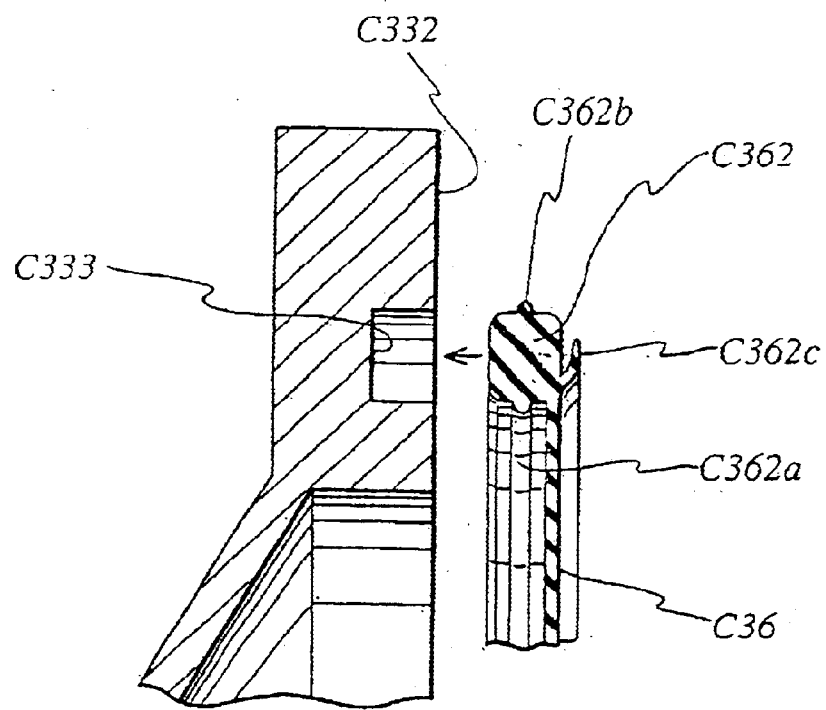
FIG. 40(B) shows a diaphragm mounting structure arranged in a second partition of the diaphragm unit.

Referring to FIG. 39 and FIG. 40(B), the diaphragm film C36 is a circular thin film (for example, thickness is 0.5 mm) covering the larger opening of the second diaphragm section C33. At the outer circumference of the diaphragm film C36, there is provided a flange portion C362 as an engagement portion having a cross section identical to the mounting groove C333 formed at a position corresponding to the match plane C332. This flange portion C362 is ring-shaped and unitarily formed with one side of the diaphragm film C36 (opposite surface not facing the diaphragm C35).

This flange portion C362 has protrusions C362a and C362b on the outer and inner circumference. The diaphragm film C36 and the flange portion C362 including the protrusions C362a and C362b are unitarily formed from an elastic rubber. The flange portions C362 is inserted into the mounting groove C333 and the outer and inner protrusions are tightly in contact with the inner wall of the mounting groove C333, so as to be maintained on the match plane.

Moreover, the diaphragm film C36 includes a functional protrusion C362c as shown in FIG. 39 and FIG. 40(B). This functional protrusion C362c is used not only for removal but also as a valve member.

FIG. 41(A) shows the diaphragms C35 and C36 when subjected to a positive pressure from the oscillating air pressure generator C20, and FIG. 41(B) shows the diaphragms C35 and C36 when subjected to a negative pressure from the oscillating air pressure generator C20.

In FIG. 41(A), the diaphragm C35 pushes the diaphragm C36 and the air contained between the diaphragm C35 and the diaphragm C36 is pushed outside. In this case, the functional protrusion C362c is pushed by the air to make a clearance between the diaphragm C35 and the functional protrusion.

In FIG. 41(B), the diaphragm film C35 pulls the diaphragm film C36 and accordingly, the clearance between the diaphragm films 35 and C36 tends to expand. Consequently, the air pressure between the diaphragm films C35 and C36 is lowered than the atmospheric pressure. However, the functional protrusion C362c is pushed by the atmospheric air to be in tight contact with the diaphragm film C35 to prevent intrusion of the outer atmospheric air.

Thus, the functional protrusion C362c prevents air intrusion while the diaphragm films C35 and C36 moves reciprocally, enabling to maintain the small clearance between the diaphragm films C35 and C36. This prevents irregular collision between the diaphragm films C35 and C36, which in tern prevents wearing of the diaphragm films. Thus, it is possible to increase the service life of the diaphragm films.

Next, explanation will be given on the support unit C40 referring back to FIG. 36. The support unit C40 includes a first support frame C41 for supporting the first diaphragm section, a second support frame C42 for supporting the second diaphragm section, a linkage body for rotatably linking the first and second support frames C41 and C42, and linkage urging mechanism 44 for urging the support frames C41 and C42 in the direction for bringing into contact the match planes C322 and C332 of the first and the second diaphragm sections C32 and C33.

The first support frame C41 is a sheet-shaped member held vertically with its upper end and lower end firmly fixed to a basement such as a wall of a building, and having at its center a through hole where the first diaphragm section C32 in inserted and fixed with a screw, bolt, and the like. At the back of the support frame C41, the linkage urging mechanism 44 is mounted as will be detailed later.

The second support frame C42 has at its center a through hole where the second diaphragm section is inserted. The second support frame C42 can rotate together with the second diaphragm section around a rotary shaft C431 of a linkage body C43.

The through holes of the support frames C41 and C42 are positioned so that the match planes C322 and C332 of the first and the second diaphragm sections are matched with each other when the first support frame C41 and the second support frame 42 are closed, i.e., they face each other.

A rubber ring C421 is mounted as a cushion in the through hole of the second support frame C42. This rubber ring C421 has a plurality of protrusions C421a at an identical interval inside the rubber ring C421. These protrusions protrude in a vertical direction against the match plane C332 of the second diaphragm section C33. These protrusions are in abutment with the flange portion of the second diaphragm section. When the first support frame C41 and the second frame C42 are closed and the match planes C322 and C332 of the first and the second diaphragm sections are brought into abutment with each other, the elastic protrusions C421a generates a pressure to sandwich the diaphragm films C35 and C36.

The linkage body C43 includes the rotary shaft C431 supported by the first support frame C41 and serves as an axis of rotation of the second support frame C42; a shaft holder C432 capable of moving the rotary shaft C431 toward or away from the first support frame C41; and a bearing (not depicted) mounted on one end of the second support frame C42.

The rotary shaft C431 is supported at one end of the first support frame C41 and connected via the bearing to the one end of the second support frame C42. This rotary shaft C31 has a length almost identical to the width (vertical to the paper surface) of the second support frame C42.

The shaft holder C432 includes: a holder block C432a for holding the rotary shaft C431 parallel to the match plane C322 of the first diaphragm section C32; a guide member C432b for guiding the movement of the holder block toward or away from the first support frame C41; a cylindrical member 432c provided on the first support frame C 41 for slidably holding the guide member C432b; and an extension spring for pulling the holder block C432a toward the first support frame C41.

It should be noted that two of the shaft holders C432 are mounted at the both ends of the rotary shaft C431. The linkage body C43 having the aforementioned configuration, is capable of rotating the second support frame C42 around the support shaft 431 and pulls, via the rotary shaft, the second support frame C42 toward the first support frame C41.

The linkage urging mechanism 44 includes: a claw member C441 arranged on the first support frame C41 in such a manner that the claw member C441 can slide upward and downward along the match plane C322 of the first diaphragm section; an engagement member C442 with which the claw member is engaged; and a slide urging mechanism for urging the slide of the claw member C441.

Figure 42A:
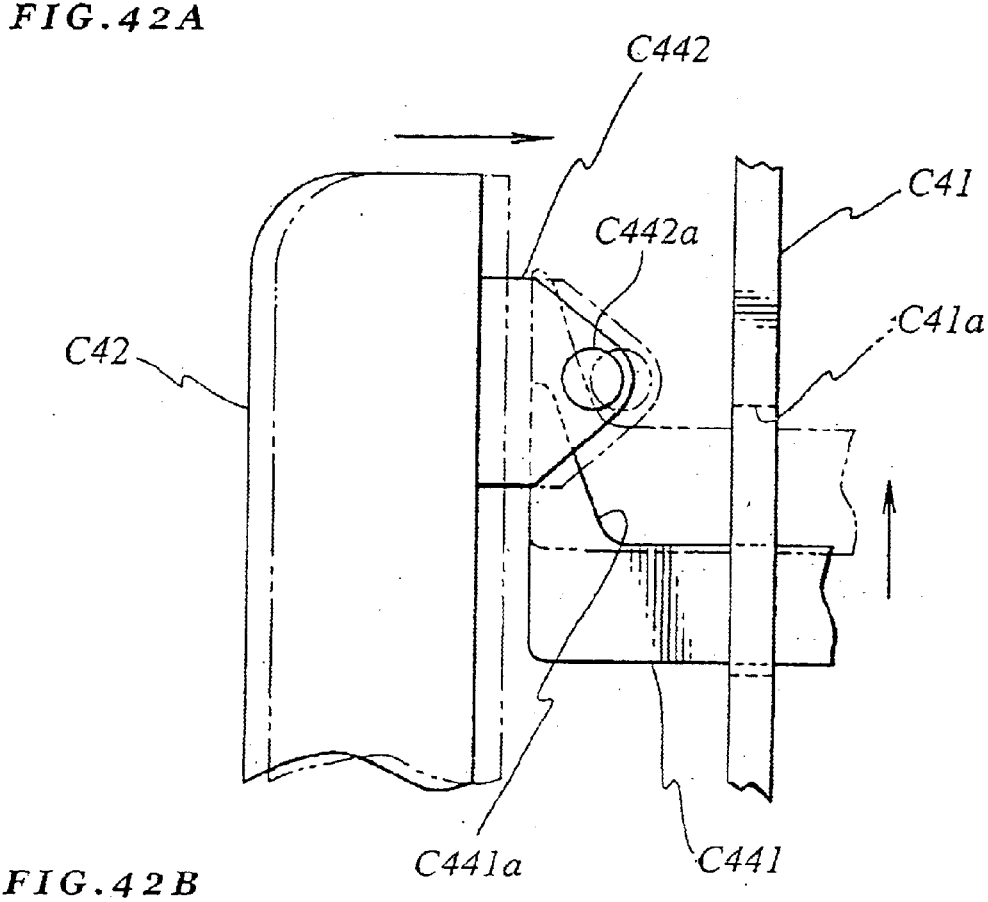
FIG. 42(A) is a front view and FIG. 42(B) is a top view of the claw member with the engagement member.
Figure 42B:
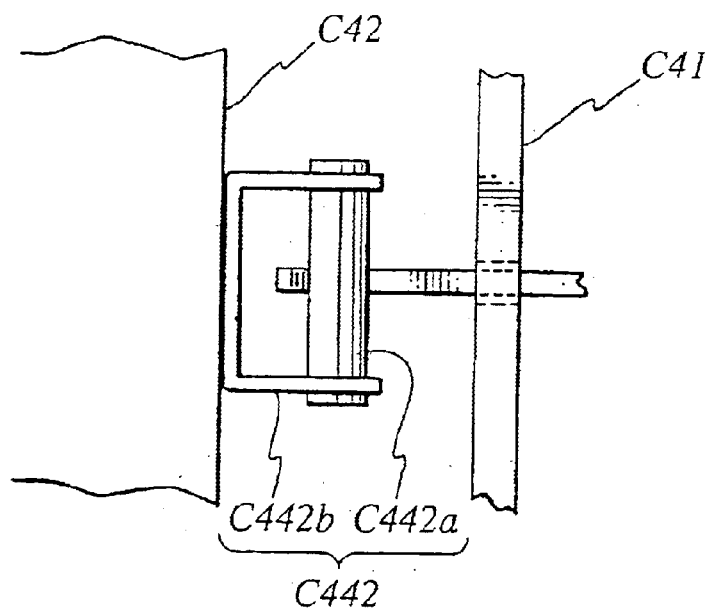

FIG. 42(A) is a front view and FIG. 42(B) is a top view of the claw member C441. As shown in FIG. 42, the claw member C441 is supported by the slide urging mechanism C443 in such a manner that the claw end is directed upward. This claw extends through a longitudinal hole C41a of the first support frame C41 in the vertical direction to the first support frame C41 and its tip end is bent upward. This tip end has a slope C441a and decreases its width upward, i.e., away from the first support frame.

On the other hand, the engagement member C442 is arranged on the second support frame C42 at a position corresponding to the claw member C441. The engagement member C442 includes a round bar C442a and a support member C442 for supporting both ends of the round bar at a predetermined distance from the second support frame C42. The round bar C442a is supported in parallel to the surface of the second support frame C42 facing the first support frame C41 and vertical to the slide direction of the claw member C441. Furthermore, the position of the round bar C442a is positioned as follows. When the first support frame C41 and the second support frame C42 are closed by rotation (as shown in FIG. 36), the round bar C442a is positioned near to the first support frame C41 than the bent tip of the claw member C441.

Accordingly, as shown in FIG. 42(A), when the claw member slides upward, the round bar C442a is brought into abutment with the slope C441a. And if the claw member C441 is further moved upward, the round bar C442a slides along the slope C441a, so that the second support frame C42 is pulled toward the first support frame C41.

It should be noted there are provided four of the pair of the claw member C441 and the engagement member C442.

As shown in FIG. 36, the aforementioned slide urging mechanism C443 includes: a claw holding plate C444 having a prolonged plate form for holding the claw member; a plate holder C445 for holding the claw holding plate C444 in such a manner that the claw holding plate can be moved up and down reciprocally; a manual lever C446 for urging the vertical movement of the claw holding plate; and a lever holder C447 for rotatably holding this manual lever C446.

The claw holding plate C444 has the claw member C441 at the upper end and the lower end. More specifically, the claw holding plate C444 and the claw members C441 are unitarily formed.

A pair of plate holders C445 is arranged at the back of the first support frame C41 at the upper and lower positions of the claw holding plate C444. Moreover, the plate holders C445 are arranged at the depth of the paper sheet, and there are four of the plate holders C445 in all. Each of the plate holders C445 has a prolonged through hole C445a with which a protrusion on the claw holding plate C444 is engaged. While the protrusion moves up and down along the prolonged hole C445a, the claw holding plate C444 can have a stable vertical movement.

The manual lever C446 is supported on a rotary shaft C447a of the lever holder C447. One end (first end) of this manual lever C446 is to be moved manually and the other end (second end) is rotatably linked to the upper ends of the two claw holding plates C444. The second end has a prolonged hole C446a and each of the claw holding plates C444 has a protrusion C444b to be engaged with the prolonged hole.

When the manual lever C446 is manually pushed in the direction of Q, the second end of the manual lever C446 moves upward while the protrusion C44b is slightly moved along the aforementioned prolonged hole so as to raise the claw holding plates C444. In order to lower the claw holding plates C444, the manual lever is moved in the opposite direction of Q.

The lever holder C447 is mounted on the surface of the first support frame C41 facing the second support frame, and supports the manual lever C446 via a rotary shaft C447a. This rotary shaft C447a is arranged horizontally and parallel to the first support frame C41.

Moreover, the lever holder includes an index plunger C47b serving as a stopper to fix the position of the manual lever when the claw members C441 are at their upper positions. This index plunger C447b includes a protrusion extending through the lever holder C447 to reach the manual lever C446; a spring always pushing the protrusion to the side of the manual lever; and a tab to pull back the protrusion. On the other hand, the manual lever C446 has an engagement hole C446b at a position corresponding to the protrusion of the index plunger when the manual lever C446 is pushed down in the direction of Q. Accordingly, when the manual lever C446 is pushed down, the protrusion of the index plunger C447b comes into the engagement hole C446b so that the manual lever C446 is fixed. In order to release this fixed state, it is necessary to pull the tab of the index plunger C447b.

The reference symbol C45 is a stopper for maintaining the second support frame C42 in a horizontal state when it is rotated with respect to the first support frame C41. This stopper 45 has an elastic protrusion to protect the second support frame 42 when it is in abutment with the stopper C45.

Description will now be directed to handling and operation of the diaphragm unit C30 having the aforementioned configuration.

The diaphragm films C35 and C36 are mounted on the first diaphragm section C32 and the second diaphragm section C33 for use in the artificial respiration apparatus C12. After using the artificial respiration apparatus C12, the diaphragm unit C30 is washed as follows.

Firstly, the fixed state of the index plunger C447 is released and the manual lever C446 is pulled up in the opposite direction of Q. This lowers the claw holding plates C444 and simultaneously with this, the claw members C441 are also lowered. Thus, the claw members C441 are disengaged from the engagement members C442. In this state, the second support frame C42 can be rotated with respect to the first support frame C41 (in the direction of W in FIG. 36) to the position shown by the alternate long and two short dashes line.

When the diaphragm films C35 and C36 are adjacent to each other between the first diaphragm section and the second diaphragm section, only the second diaphragm section and the diaphragm C36 mounted thereon may be in contact with the exhaled gas during artificial respiration.

Accordingly, it is possible to maintain a sufficiently hygienic state only by washing and sterilizing the second diaphragm section C33 and the diaphragm C36. The second diaphragm section is removed from the support frame C42 and the diaphragm film C36 is removed from the second diaphragm section so as to be washed and sterilized.

Here, the first diaphragm section C32 has the diaphragm film C35 mounted thereon and there is no danger of intrusion of dust into the first diaphragm section. This also obviates the need to remove the first diaphragm section C32 from the oscillating air pressure generator C20 and facilitates washing and sterilization of the diaphragm unit C30, reducing the load on the user.

Moreover, because the diaphragm films C35 and C36 are detachably mounted on the match plane C322 and C332 of the first and the second diaphragm sections, it is possible to prevent removal of the diaphragm film C35 from the first diaphragm section C32 during the washing and sterilization of the second diaphragm section. It is also possible to prevent intrusion of dusts into the first diaphragm section.

Furthermore, the support unit includes the first support frame C41 for supporting the first diaphragm section and the second support frame C42 for supporting the second diaphragm section which are connected and disconnected via the claw member 441. Thus, it is possible to connect and disconnect the first diaphragm section C32 and the second diaphragm section C33 only by the reciprocal sliding of the claw member C441. That is, the diaphragm unit C30 can be disassembled by an easy operation, reducing load on the user when washing and sterilizing the second diaphragm section C33.

Next, explanation will be given on the oscillating air pressure generator C20 with reference to FIG. 43 through FIG. 51.

Figure 43:
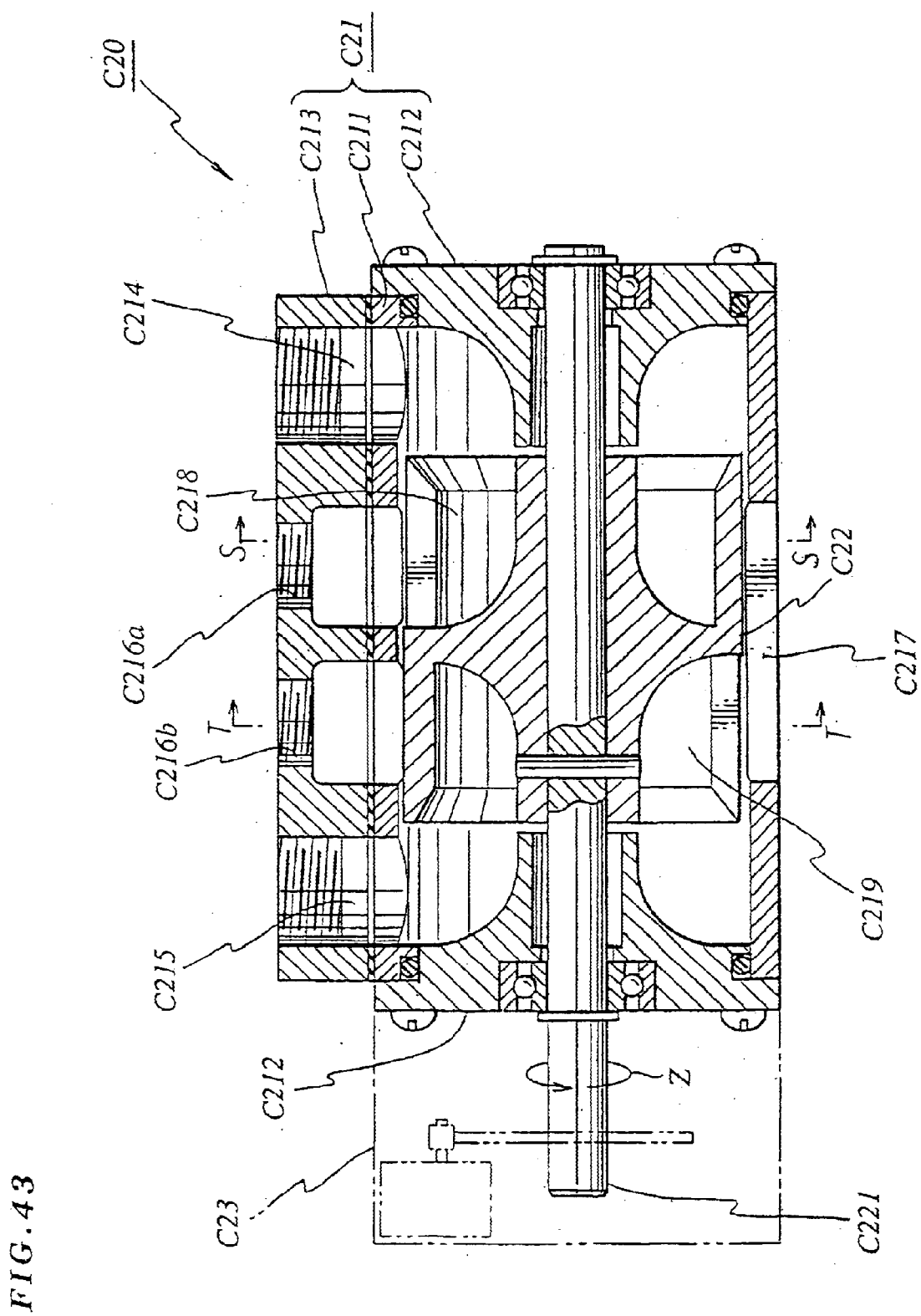
FIG. 43 is a cross sectional view of the oscillating air pressure generator of FIG. 35 along the rotary shaft.
Figure 44A:
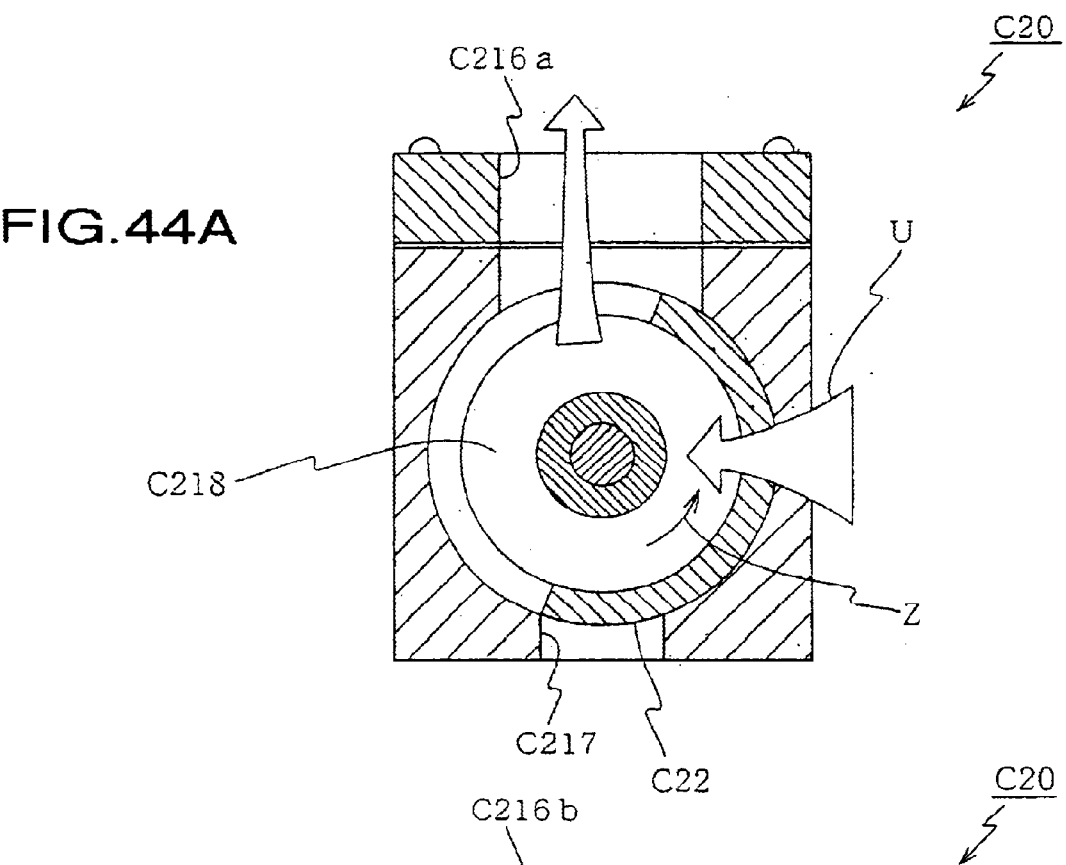
FIG. 44(A) is a cross sectional view about the line S—S in FIG. 36.
Figure 44B:
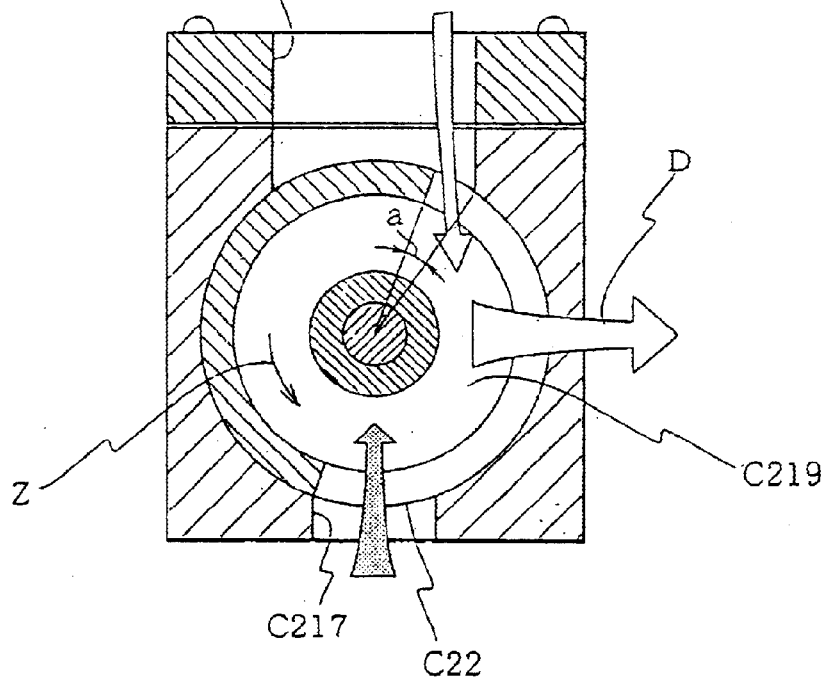
FIG. 44(B) is a cross sectional view about the line T—T in FIG. 36.

FIG. 43 is a cross sectional view of the oscillating air pressure generator C20 about a rotary shaft which will be detailed later. FIG. 44(A) is a cross sectional view of the air pressure supplier C20 about the line S—S in FIG. 43, and FIG. 44(B) is a cross sectional view about the line T—T in FIG. 43.

The oscillating air pressure generator C20 includes: a frame body C21 having a predetermined inner space; a cylindrical switching member C22 rotatably mounted in the inner space of the frame body C21; and a drive unit C23 for urging rotation of the switching member C22.

The frame body C21 includes a cylindrical member C211 having an inner diameter slightly greater than the outer diameter of the switching member C22; lids C212 for closing the both ends of the cylindrical member C211; and a pipe connector C213 where ports are formed as will be detailed later. The switching member C22 is supported on the rotary shaft C221 mounted on the lids C212 via a bearing and is arranged at the center of the cylindrical member C211.

Furthermore, the frame body C21 includes: a positive pressure input port C214 to which the aforementioned positive pressure pipe C521 is connected; a negative pressure input port C215 to which the negative pressure pipe C522 is connected; atmospheric ports C216a and C216b which are open to the atmospheric air; and an output port C217 for outputting an oscillating air pressure to the diaphragm unit C56 via the oscillating air pressure pipe C546.

The positive pressure input port C214 and the negative pressure input port C215 are formed through the both ends of the frame body C21 and respectively communicate with the both ends of the switching member C22. Moreover, the output port C217 and the atmospheric ports C216a and C216b are formed through the center of the cylindrical member C211 and each of them faces the outer circumference of the switching member C22. Moreover, the output port C217 and the atmospheric port C216 are positioned symmetrically with respect to the rotary shaft C221.

The rotary shaft C221 is inserted into the center of the switching member C22 and fixed by a pin, so that the switching member is rotated together with the rotary shaft C221. The switching member C22 has two cut-off portions, a first cut-off portion and a second cut-off portion, cut off respectively from the end surfaces and the outer circumference. These cut-off portions are cut off by 180 degrees of the outer circumference around the rotary shaft C221. The two cut-off portions are at positions shifted by 180 degrees to sandwich the rotary shaft C221. One of the cut-off portions, The cut-off portions selectively face the output port C217 and the atmospheric ports C216a and C216b with the rotation of the switching member C22. Accordingly, the first cut-off portion cut-off from the end surface of the switching member communicating with the positive pressure input port C214 forms a first flow path C218 selectively communicating the positive input port C214 with the output port C217 or the atmospheric port C216a. Similarly, the second cut-off portion cut off from the end surface of the switching member C22 communicating with the negative pressure input port forms a second flow path selectively communicating the negative input port C215 with the output port C217 or the atmospheric port C216b.

The switching member C22 having the flow paths C218 and C219, during its rotation, can switch between a first state and a second state. In the first state, the positive pressure input port C214 is connected to the output port and the negative pressure input port C215 is connected to the atmospheric port C216b. In the second state, the positive pressure input port C214 is connected to the atmospheric port C216a and the negative pressure input port C215 is connected to the output port C217.

The drive unit C23 is positioned adjacent to the frame body C21 and engaged with one end of the rotary shaft C221 extending outward from the frame body C21. That is, the drive unit C23 includes a drive motor and a reduction gear set for reducing the rpm transmitted to the rotary shaft C221. Since the artificial respiration apparatus C12 requires an oscillating air pressure at frequency of 15 Hz, the drive unit C23 rotates the rotary shaft C221 at 900 rpm. Moreover, the drive unit C23 makes the switching member C22 rotate constantly in the direction of Z as shown in FIG. 43.

Furthermore, in this oscillating air pressure generator C20, as shown in FIG. 44, the atmospheric ports C216a and C216b have a greater width than the output port C217. Accordingly, during the rotation of the switching member C22, when the first flow path C218 is to start connection with the output port, the second flow path C219 is already connected to the atmospheric port C216b. In other words, when the first flow path C218 communicates the positive pressure input port C214 with the output port C217 and the second flow path communicates the negative pressure input port C215 with the atmospheric port C216b, the communication between the negative pressure input port C215 and the atmospheric port C216b starts earlier than the communication between the positive pressure input port C214 and the output port C217.

Referring to FIG. 44, with rotation of the switching member C22, when the upstream end of the first flow path C218 is positioned immediately before the output port C217, the upstream end of the second flow path C219 has already reached the atmospheric port C217 and precedes by the angle "a". This angle "a" is may be 10 to 50 degrees and more preferably, 20 to 50 degrees.

FIG. 44 through FIG. 51 successively show a gas flow into the respective ports generated according to the rotation of the switching member C22. In this figures, (A) shows a gas flow in the first flow path C218 and (B) shows a gas flow in the second flow path C219. Moreover, in the figures, the arrow U indicates a gas flow from the positive pressure input port C214 into the oscillating air pressure generator, and the arrow D indicates a gas flow from the negative pressure input port C215 sucked into the oscillating air pressure generator C20.

Referring to FIG. 44 through FIG. 51, explanation will be given on the operation of the oscillating air pressure generator C20. When the first flow path connects the positive pressure input port C214 with the output port C217 and the second flow path C219 connects the negative pressure input port C215 with the atmospheric port C216b (FIG. 46 to FIG. 49), an atmospheric air is taken in from the atmospheric port C216b and supplied via the negative pressure input port C215 into the blower C52. Moreover, the air taken in is output as a positive pressure from the output port C217 via the positive pressure input port C214 into the diaphragm unit C56.

With rotation of the switching member C22, when the first flow path C218 connects the positive pressure input port C214 with the atmospheric port C216a and the second flow path C219 connects the negative pressure input port C215 with the output port C217 (FIGS. 50, 51, 44, and 45), the gas in the diaphragm unit C56 is sucked at the output port C217. Furthermore, the gas taken in is sucked by the blower C52 via the negative pressure input port C215, and exhausted into the atmosphere via the positive pressure input port C214 and the atmospheric port C216a.

The switching member C22 is driven by the drive unit C23 to successively repeat the aforementioned connection states. At the output port C217, gas is taken in and out successively so as to apply an oscillating air pressure to the diaphragm unit C56.

Figure 45A:
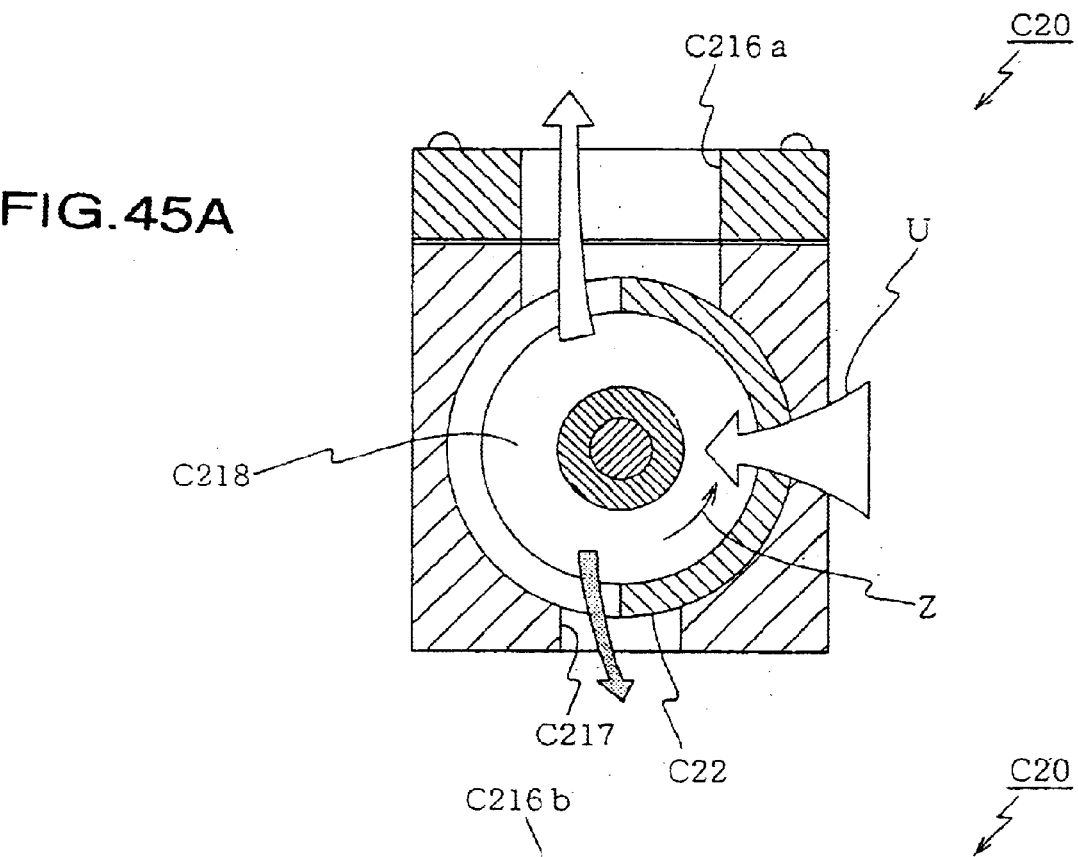
FIG. 45(A) shows a gas flow in a first flow path and FIG. 45(B) shows a gas flow in a second flow path.
Figure 45B:
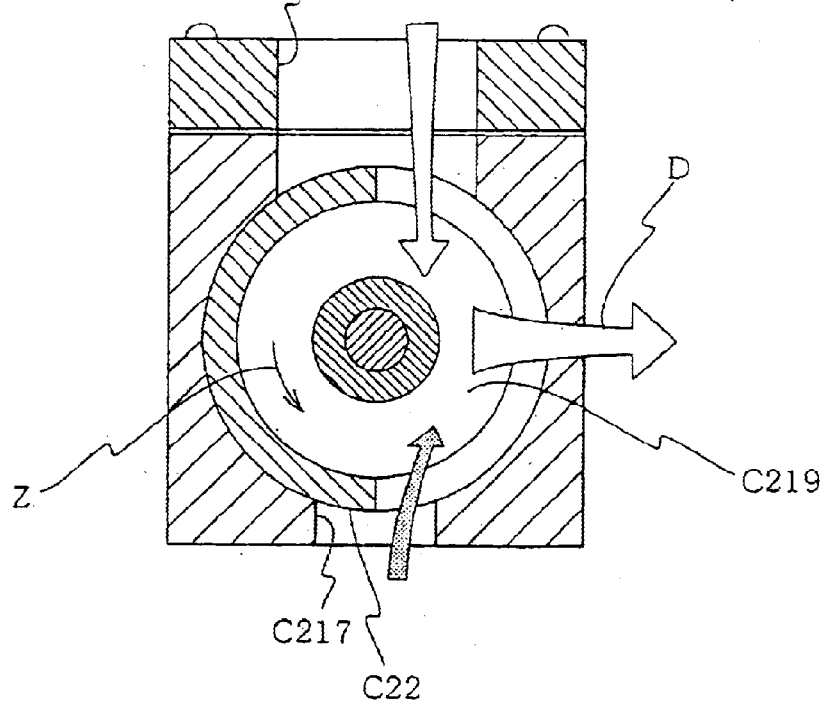
Figure 46A:
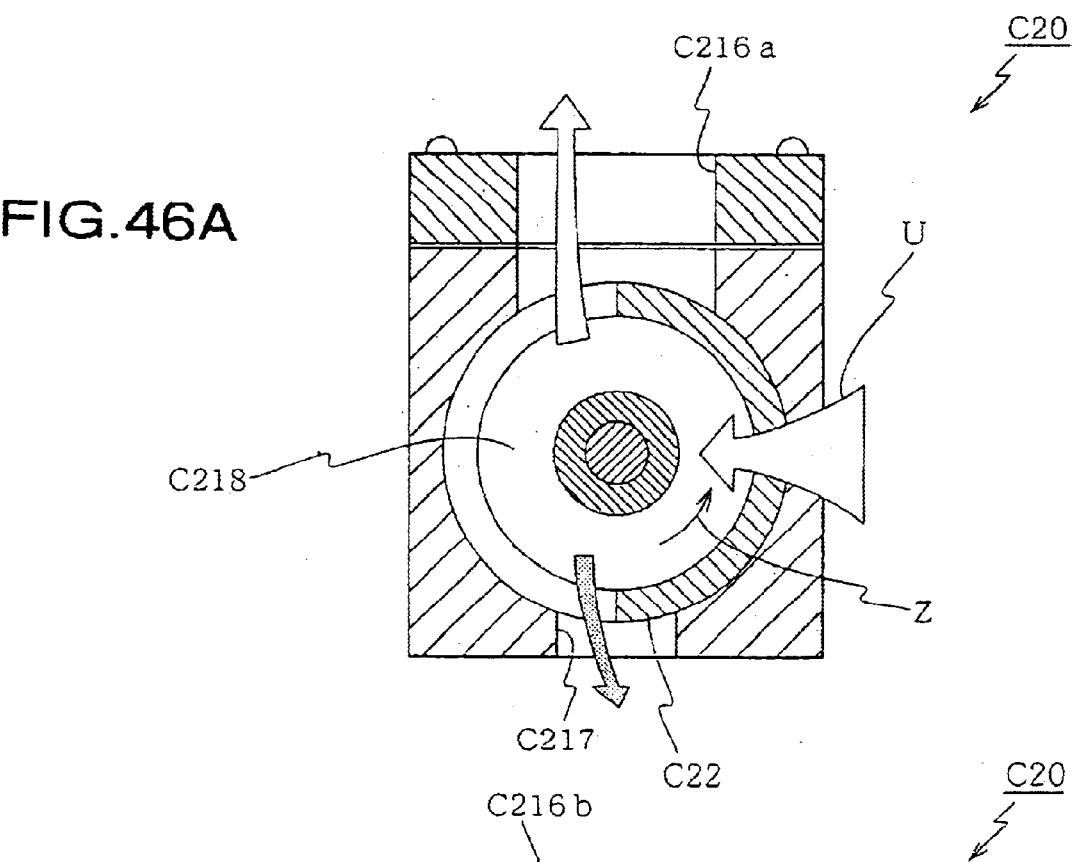
FIG. 46(A) shows a gas flow in the first flow path and FIG. 46(B) shows a gas flow in the second flow path.
Figure 46B:
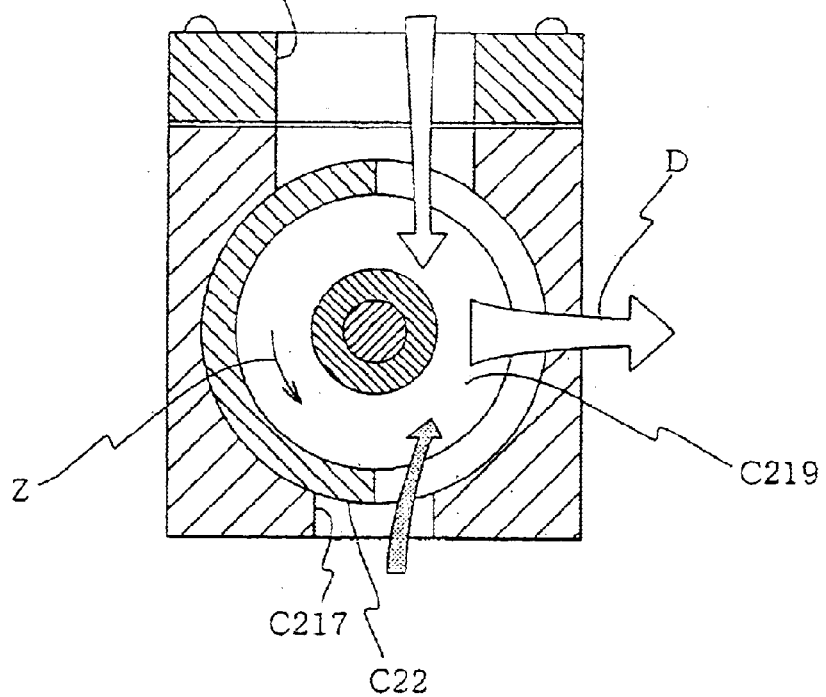
Figure 47A:
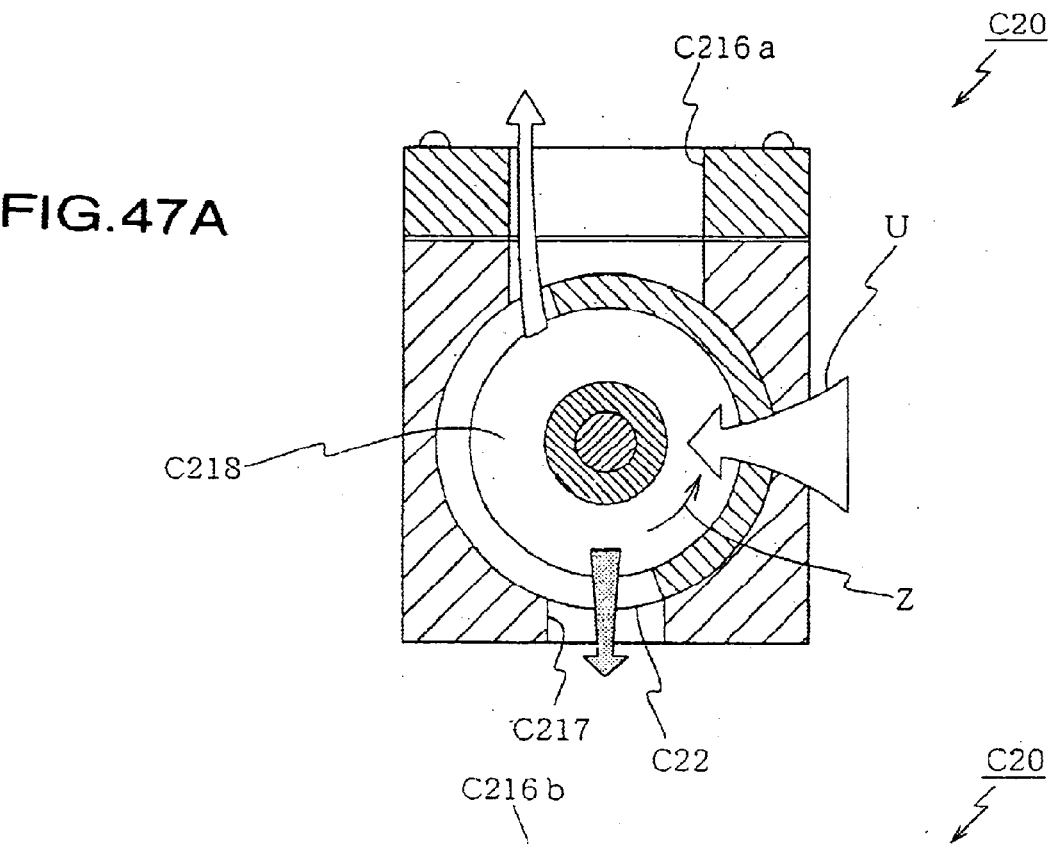
FIG. 47(A) shows a gas flow in the first flow path and FIG. 47(B) shows a gas flow in the second flow path.
Figure 47B:
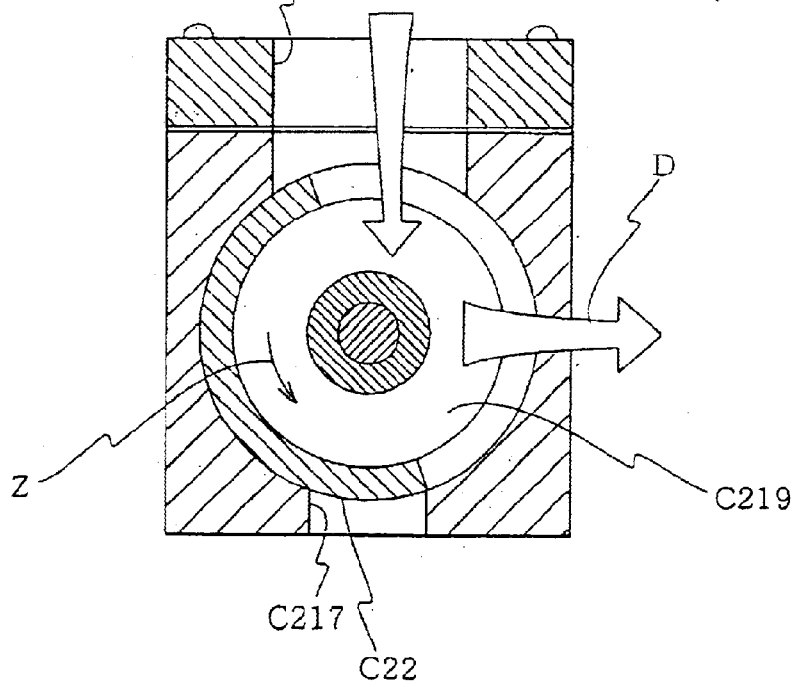
Figure 48A:
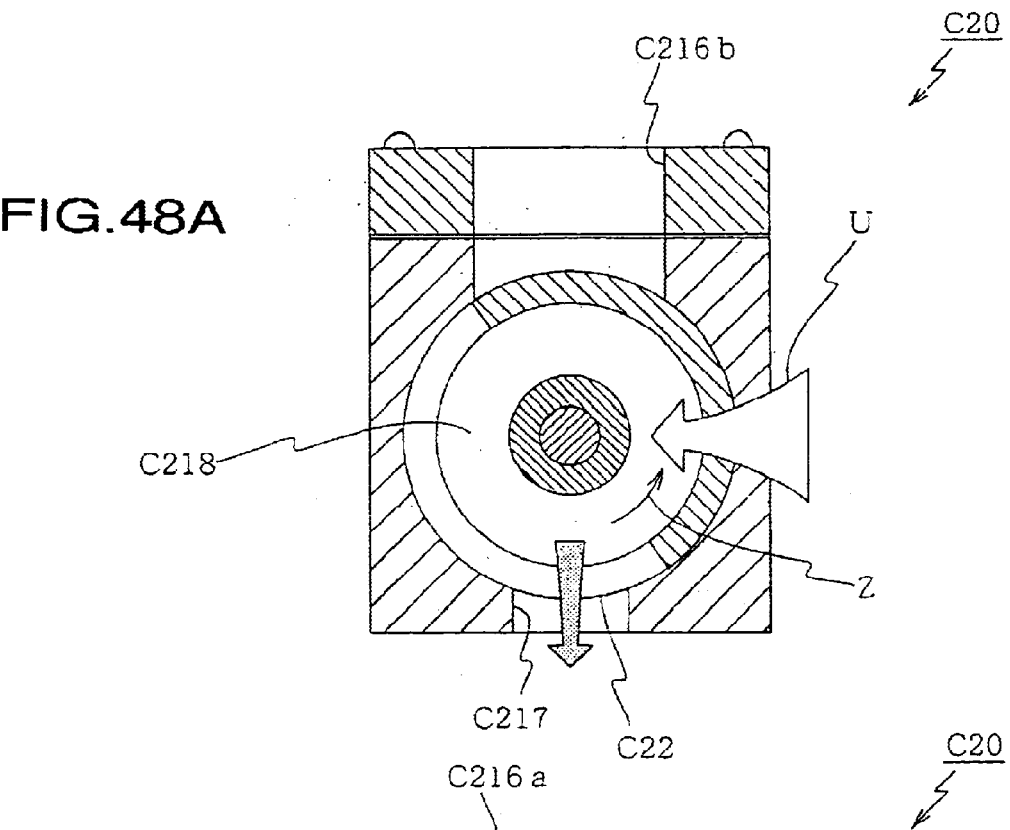
FIG. 48(A) shows a gas flow in the first flow path and FIG. 48(B) shows a gas flow in the second flow path.
Figure 48B:
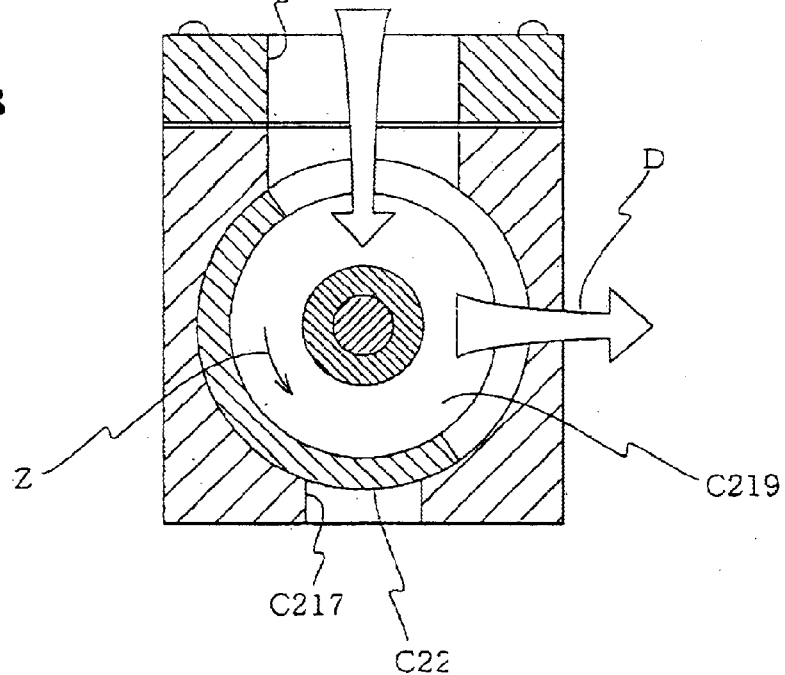
Figure 49A:
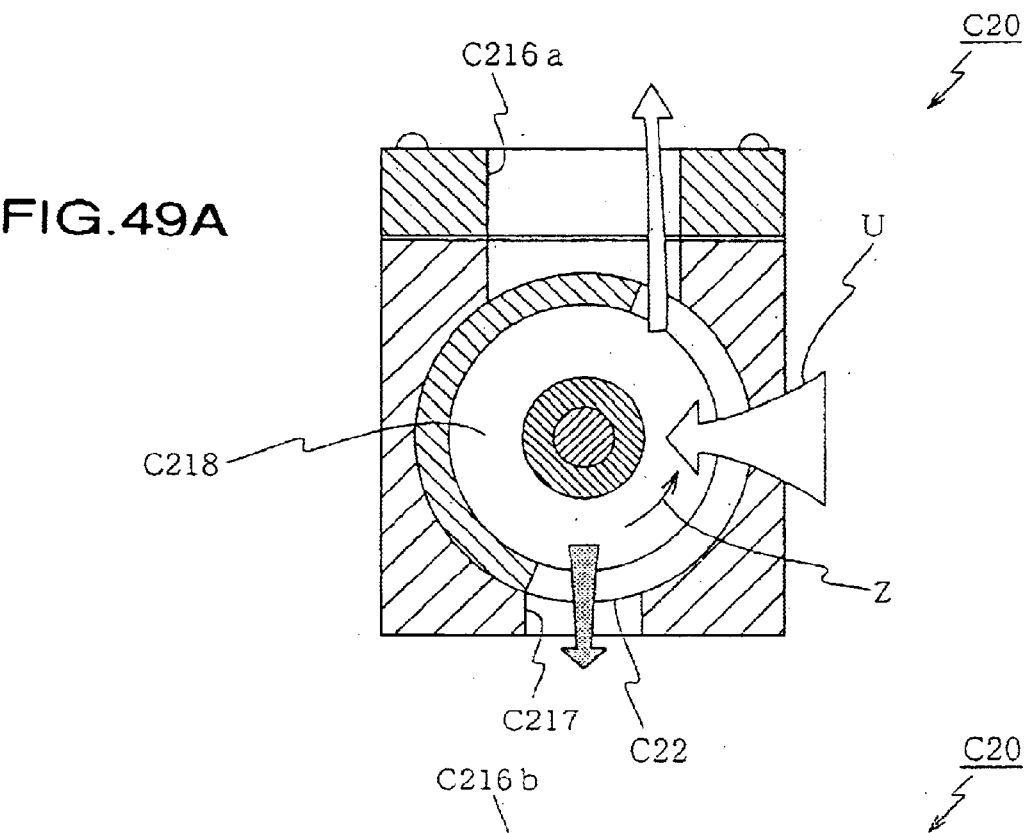
FIG. 49(A) shows a gas flow in the first flow path and FIG. 49(B) shows a gas flow in the second flow path.
Figure 49B:
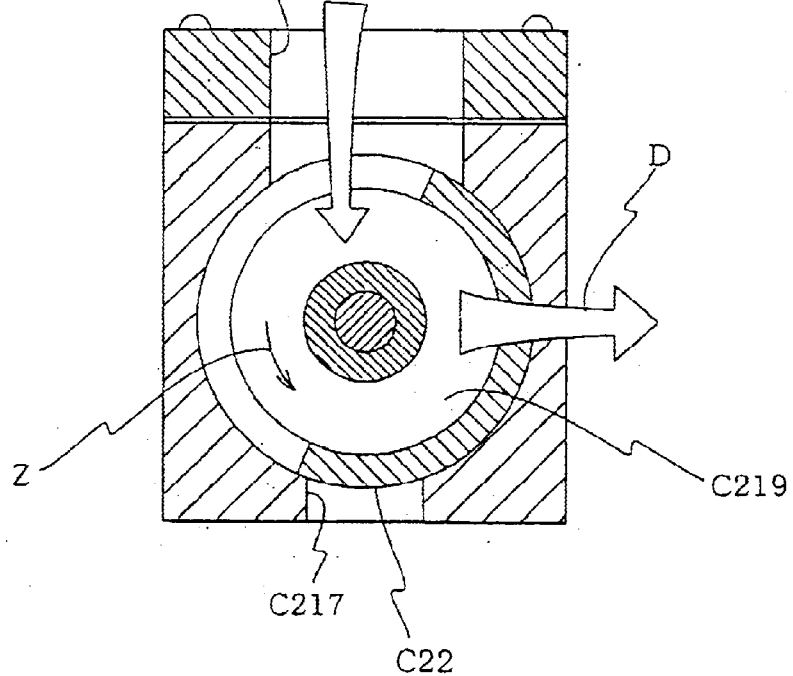
Figure 50A:
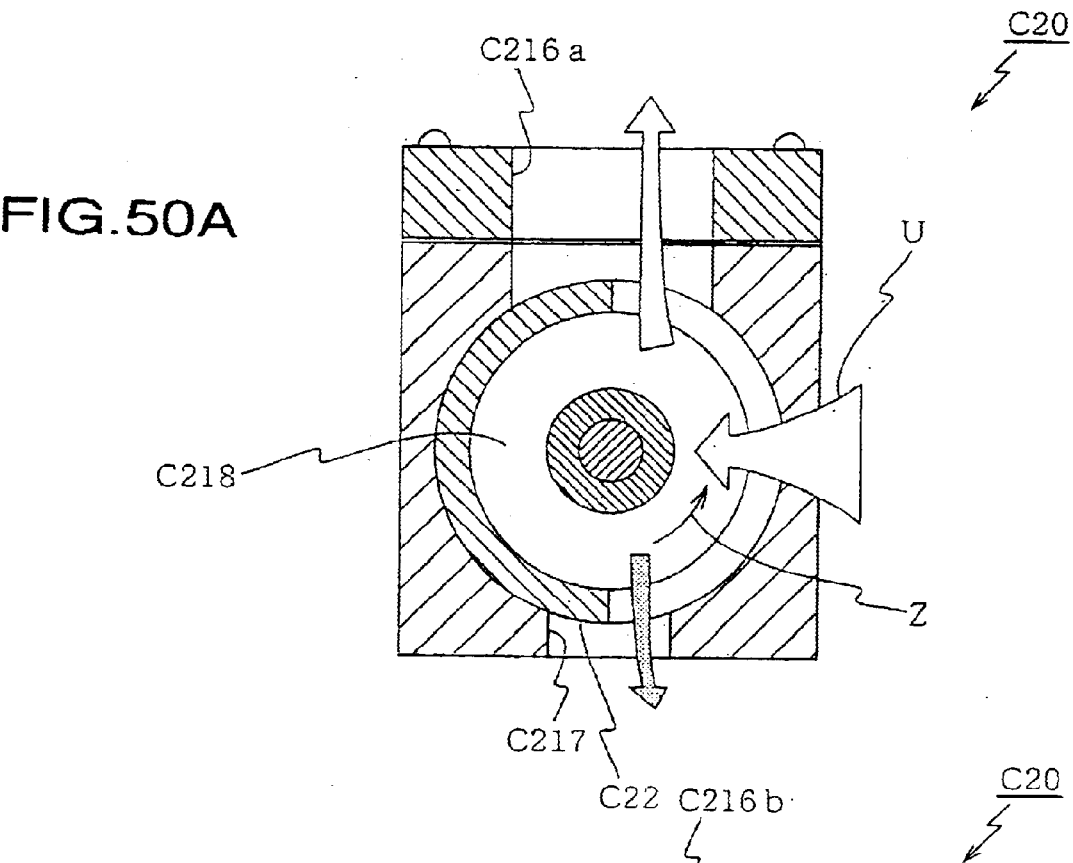
FIG. 50(A) shows a gas flow in the first flow path and FIG. 50(B) shows a gas flow in the second flow path.
Figure 50B:
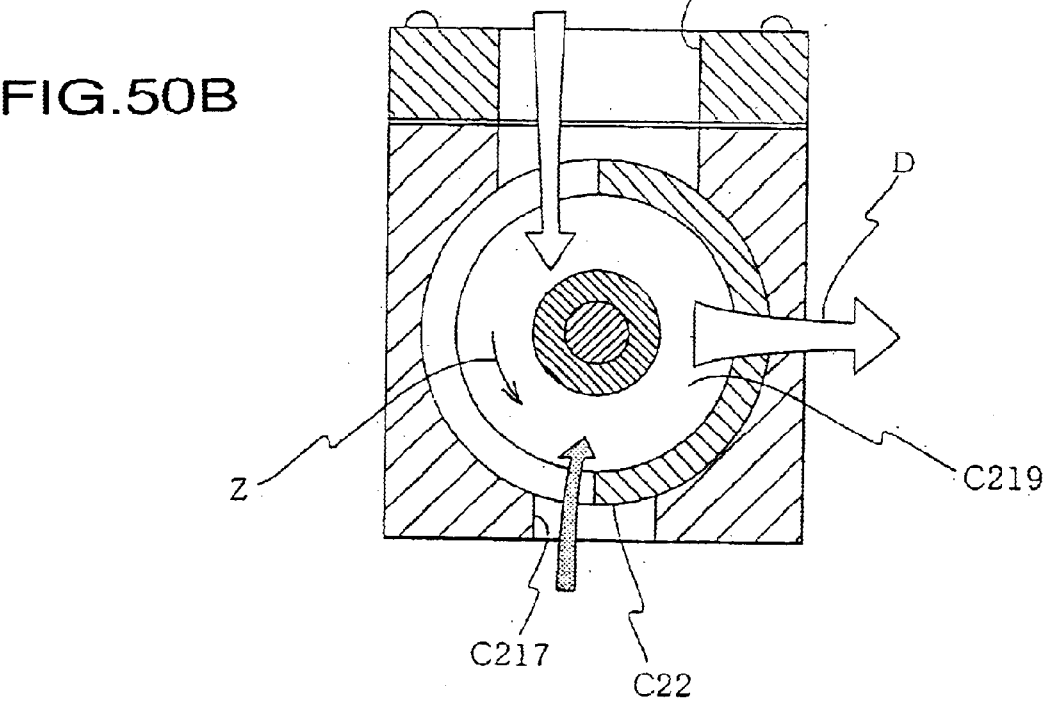
Figure 51A:
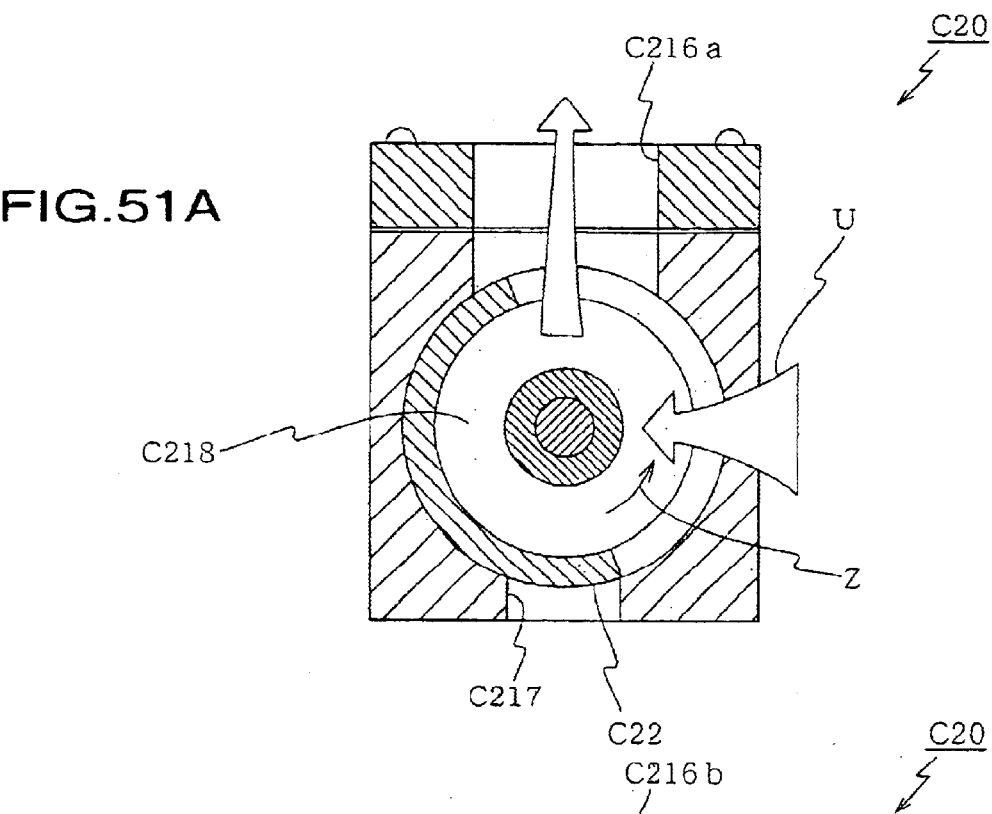
FIG. 51(A) shows a gas flow in the first flow path and FIG. 51(B) shows a gas flow in the second flow path.
Figure 51B:
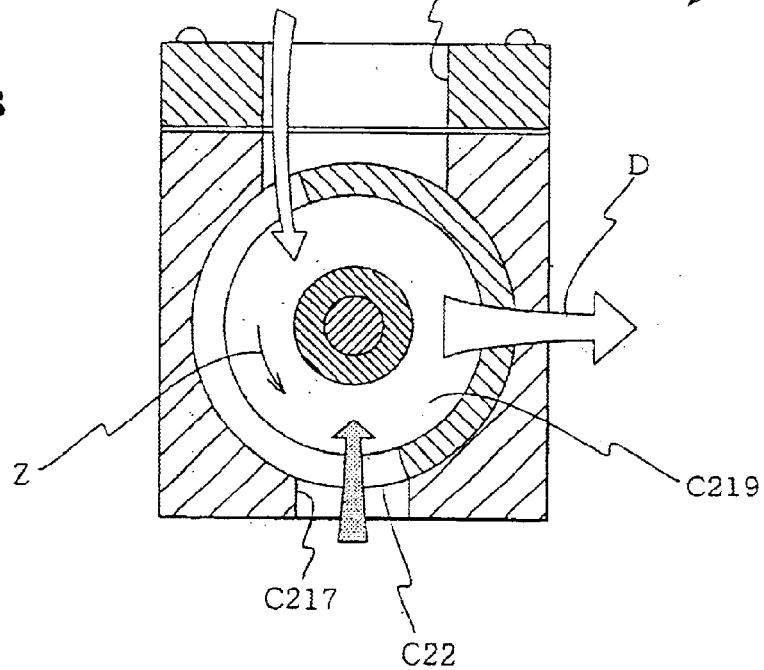
Figure 52:
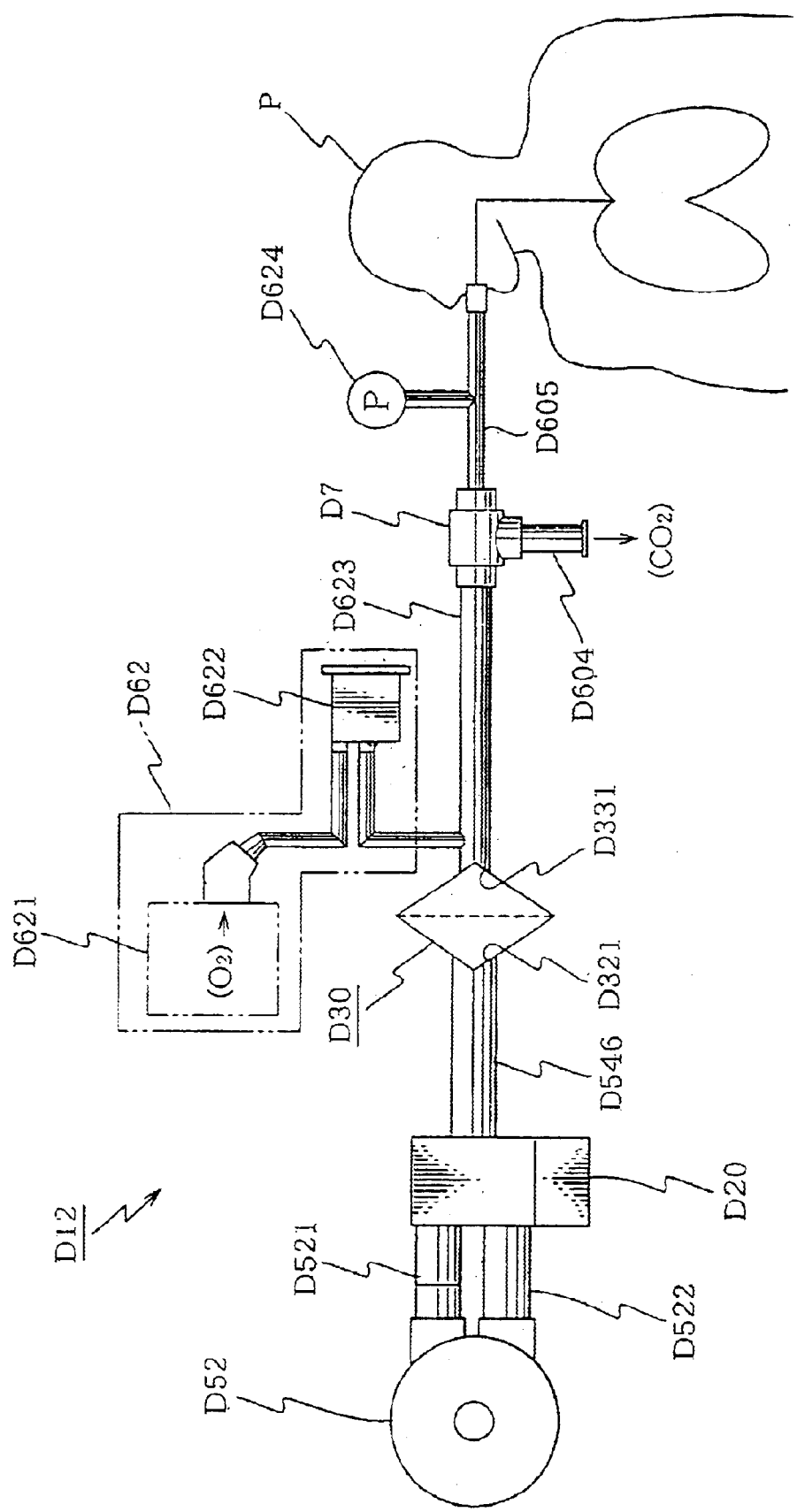
FIG. 52 shows configuration of an artificial respiration apparatus according to the fourth embodiment of the present invention.

During generation of the oscillating air pressure, when the first flow path of the switching member C22 is to start connection between the positive pressure input port C217 and the output port C217, the second flow path C219 has already connected the negative pressure input port C215 with the atmospheric port C216b (FIG. 45). Thus, firstly, the air to be supplied to the blower is taken in so that the air circulates in the blower. When the positive pressure input port C214 is connected to the output port C217, positive pressure is quickly applied to the diaphragm unit C56.

Thus, it is possible to suppress the time loss in the conventional oscillating air pressure generator, i.e., the time loss of the air taken in from the atmospheric port and circulating in the blower to reach the output port. Thus, without increasing the size of the blower, it is possible to maintain a high positive pressure of the oscillating air pressure so as to increase the oscillation amplitude.

Now, explanation will be given on the operation of the high-frequency artificial respiration apparatus C12 having the aforementioned configuration. The inhale gas supply unit C62 starts inhale gas (oxygen) supply and the blower C52 starts operation. The positive pressure and negative pressure generated by the blower C52 are converted into an oscillating air pressure by the oscillating air pressure generator and transmitted to the diaphragm unit C30. In the diaphragm unit C30, the diaphragm films C35 and C36 are simultaneously oscillated by the oscillating air pressure, so as to change the pressure in the inhale pipe C623.

Here, the diaphragm film C35 has a thicker portion at the center of the film and this thicker portion oscillates forward and backward, reducing waving of the film as in the conventional diaphragm film. Thus, it is possible to effectively transmit the oscillating air pressure from the oscillating air pressure generator C20 to the inhale pipe C623.

The inhale gas passing through the inhale pipe C623 is subjected to the oscillating air pressure, so as to reach lungs of a patient who cannot breath by himself or herself, and the oxygen in the inhale gas reaches the lungs. The inhale gas reaches the lungs in an oscillating state. Moreover, the exhaled gas containing carbon dioxide from the lungs advances in the inhale end pipe C605 in the opposite direction to the inhale gas and is exhausted through the exhaust pipe. Here, the three-way branched pipe C7 functions as a guide to separate the interior of the inhale end pipe C605 into a region for passing the inhale gas and a region for passing the exhaled gas.

Embodiment 4

Description will now be directed to a fourth embodiment of the present invention. In this embodiment, a diaphragm unit D30 is mounted on an artificial respiration apparatus D12 of the high-frequency oscillating ventilation (HFO) method for performing oxygen inhale and exhaled gas exhaust. The artificial respiration apparatus D12 includes: an inhale gas supply unit D62 as an oxygen supply source; a blower(air pressure supplier) D52 for simultaneously generating a positive pressure and a negative pressure; an oscillating air pressure generator D20 for alternately selecting the positive or the negative pressure from the blower D52 and converts them into a predetermined oscillating air pressure; a diaphragm unit D30 urged to operate by the oscillating air pressure from the oscillating air pressure generator D20 for applying an oscillating air pressure to the oxygen (oxygen mixed with air) supplied to a patient P from the inhale gas supply unit D62; and a piping for supplying oxygen to the patient and exhausting exhaled gas.

The inhale gas supply unit D62 includes: a blender D621 for mixing the atmospheric air with oxygen prepared in advance; and a humidifier D622 for humidifying the air transmitted from the blender D621. The humidifier D622 is connected to an inhale pipe D6223 for supplying to the patient the inhale gas which has passed through the humidifier. The inhale pipe D623 has one end connected to an output opening D331 of the diaphragm unit D30 and the other end connected to the inhale end pipe D605 via the three-way branched pipe D7. A pressure sensor D624 is attached in the middle of the inhale end pipe D605 for detecting an inhale state of the patient P. Moreover, the three-way branched pipe D7 is also connected to an exhaust pipe D604 for exhausting exhaled gas.

The input opening D321 of the diaphragm unit D30 is connected via an oscillating air pressure pipe D546 to the oscillating air pressure generator D20. Furthermore, the oscillating air pressure generator D20 is connected to the blower D52 via a positive pressure pipe D521 and a negative pressure pipe D522. The blower takes in the air from the negative pressure pipe D522 and discharges the air through the positive pressure pipe D521.

The oscillating air pressure generator D20 is a so-called rotary valve. The oscillating air pressure generator D20 includes: a positive pressure input port connected to the positive pressure pipe D521; a negative pressure input port connected to the negative pressure pipe D522; and an output port for alternately outputting the positive pressure and negative pressure at a predetermined periodicity (15 Hz). This output port is connected to the input opening D321 of the diaphragm unit D30.

According to the present invention, the connection between the negative pressure input port and the atmospheric port precedes the connection between the positive pressure input port and the output port by the switching member. Accordingly, atmospheric air to be supplied to the air pressure supplier such as a blower can be taken in and made to circulate in the air pressure supplier before the positive pressure input port is connected to the output port.

Accordingly, it is possible to suppress the time loss caused by the atmospheric air circulating in the air pressure supplier and reaching the output port in the conventional oscillating air pressure generator. Without increasing the size of the air pressure supplier, it is possible to maintain a high oscillating air pressure, increasing the oscillation amplitude.

By applying the present invention to the artificial respiration apparatus, it is possible to supply an inhale gas with a greater pressure amplitude than in the conventional apparatus, and to increase the ventilation amount. Moreover, as there is no need of increasing size of the air pressure supplier, it is possible to reduce the power consumption and production costs as well as to reduce the size of the apparatus.

Moreover, an atmospheric port is provided for each of the positive pressure input port and the negative pressure input port. This prevents the positive pressure gas supplied from the positive pressure input port from being sucked by the negative pressure input port via the atmospheric port. Thus, by providing two separate atmospheric ports, it is possible to effectively prevent a high-temperature gas from being supplied to the air pressure supplier. This enables to increase the service life of the air pressure supplier.

According to another aspect of the present invention, the oscillating air pressure generator of a high-frequency artificial respiration apparatus includes an exhaust opening for an excessive positive pressure air and an entrance opening for taking air in; and an exhaust silencer for reducing noise caused at the exhaust opening and an inhale silencer for reducing noise caused at the entrance opening. The two separate silencers reduce the noises of two frequency characteristics. This effectively reduces the noise of the oscillating air pressure generator of the high-frequency artificial respiration apparatus.

Furthermore, with this configuration, it is possible to obviate intrusion of a high-temperature positive pressure air into the air pressure supplier, which in turn enables to increase the service life of the air pressure supplier.

Moreover, when the inhale silencer includes a sound absorbing path and a resonance chamber in combination, it is possible to reduce a noise over the entire sound region, especially a low frequency portion of the noise. This effectively lower the noise at the entrance opening.

Furthermore, when the inhale silencer includes an air filter, it is possible to remove dusts from the atmospheric air as well as to reduce the noise by making the atmospheric air pass through a clearance between a lid and a filter section.

Furthermore, when the inhale silencer has a sound absorbing path of a predetermined length, it is possible to further reduce the noise of the entire frequency region. When this sound absorbing path is formed in spiral, it is possible to provide the sound absorbing path in a small space, enabling to reduce the size of the apparatus and to increase the sound reduction effect.

Moreover, when the exhaust silencer has an expansion chamber and a sound absorbing path in combination, it is possible to reduce the noise over the entire sound region and especially a high frequency portion, which is effective for the noise generated at the exhaust opening.

Moreover, when the exhaust silencer has a resonance chamber, it is possible to reduce especially the noise of a low frequency portion, enabling to further reduce the noise.

According to another aspect of the present invention, one of the diaphragm films has a thicker portion at its center portion than the peripheral portion. When the film is subjected to an oscillating air pressure, the film center portion reciprocally moves in the vertical direction to the film, which makes the entire film and the other film simultaneously reciprocally move, so that the oscillating air pressure is effectively transmitted to the oxygen. This prevents the conventional waving phenomenon, and supplies a sufficient amount of oxygen to a patient, effectively performing ventilation in the lungs.

Furthermore, when the connection between the negative pressure input port and the atmospheric port precedes the connection between the positive pressure input port and the output port by the switching member, atmospheric air to be supplied to the air pressure supplier is taken in beforehand and can circulate in the air pressure supplier by the timing when the positive input port is connected to the output port.

This obviates the need of waiting for the atmospheric air circulating in the air pressure supplier before reaching the output port. Thus, it is possible to maintain a high positive air pressure and increase the oscillation amplitude without increasing the size of the air pressure supplier. Thus, it is possible to supply a sufficient amount of oxygen to a patient and effectively ventilate in the lungs.

Moreover, since two diaphragm films are used for the first diaphragm section and the second diaphragm section, respectively, it is possible to wash and sterilize only the diaphragm film of the second diaphragm section which is in contact with the exhaled gas, leaving the other diaphragm film of the first diaphragm section as it is.

This also prevents intrusion of dusts into the first diaphragm section. Moreover, the first diaphragm section need not be removed from the oscillating air pressure generator. This facilitates washing and sterilization of the diaphragm unit, reducing the load on the user.

Moreover, in the oscillating air pressure generator, when the atmospheric port is provided for each of the take-in opening and the exhaust opening, the positive gas of a high temperature discharged from the air pressure supplier is exhausted at a different position from the atmospheric air take-in position. Accordingly, it is possible to prevent intrusion of the high-temperature gas back into the air pressure supplier, which would deteriorate of inner components such as bearings. Thus, the service life can be increased.

Moreover, since the diaphragm film of the first diaphragm section is detachably mounted on the match plane of the first diaphragm section, it is possible to prevent disconnection of the diaphragm film while washing and sterilizing the second diaphragm section. Also, it is possible to prevent intrusion of dusts into the first diaphragm section.

The diaphragm films respectively may have an insert portion and each of the corresponding match planes may have a mounting groove, so that the insert portions can be inserted into or pulled out of the mounting grooves. Thus, it is possible to easily mount or remove the diaphragm films into/from the mounting grooves.

Moreover, the diaphragm films may have a tab, so that the diaphragm films can be grasped easily by the user.

One of the diaphragm films may have a protrusion serving as a check valve, which prevent intrusion of atmospheric air between the two diaphragm films while moving reciprocally. This enables to maintain a small clearance between the diaphragm films. This prevent friction between the diaphragm films caused when the diaphragm films irregularly collide each other. Thus, the service life of the diaphragm films can be increased.

Furthermore, when the first diaphragm section is held by the first support frame and the second diaphragm section is held by the second support frame, and the first support frame is connected and disconnected to/from the second support frame by a sliding claw member, the first and the second frames can easily be connected and disconnected. That is, with an easy operation it is possible to disassemble the diaphragm unit for washing and sterilization.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 10-347512 (Filed on Dec. 7th, 1998), Japanese Patent Application No. 10-356668 (Filed on Dec. 15th, 1998), Japanese Patent Application No. 10-359300 (Filed on Dec. 17th, 1998), Japanese Patent Application No. 10-366721 (Filed on Dec. 24th, 1998), including specification, claims, drawings and summary are incorporated herein by reference in its entirety.

What is claimed is:

1. An oscillating air pressure generator connected to an air pressure supplier for simultaneously generating a positive pressure and a negative pressure, said oscillating air pressure generator alternately selecting the positive pressure and the negative pressure to output for generating an oscillating air pressure, said oscillating air pressure generator comprising:

a frame including a positive pressure input port fed by the positive pressure from the air pressure supplier, a negative pressure input port fed by the negative pressure from the air pressure supplier, an atmospheric port open to the atmosphere, and an output port for outputting the oscillating air pressure;

a switching member that selectively switches between a connection state where the positive pressure input port is connected to the output port while the negative pressure input port is connected to the atmospheric port and a connection state where the positive pressure input port is connected to the atmospheric port while the negative pressure input port is connected to the output port; and a drive unit that continuously drives the switching member;

wherein the connection between the positive pressure input port and the output port and the connection between the negative pressure input port and the atmospheric port are performed by the switching member such that the connection between the negative pressure input port and the atmospheric port slightly precedes the connection between the positive pressure input port and the output port.

2. An oscillating air pressure generator as claimed in claim 1, wherein the switching member includes a cylindrical body rotatably mounted on the frame by a center shaft and driven to rotate in a predetermined direction by the drive unit;

the positive pressure port faces one end of the switching member, the negative pressure port faces the other end of the switching member, and the output port and the atmospheric port are arranged to face the outer circumference of the switching member so as to sandwich the center shaft;

a first flow path extends from one end of the switching member to the outer circumference of the switching member, and a second flow path extends from the other end of the switching member to the outer circumference of the switching member;

one of the second flow path and the atmospheric port being configured such that the second flow path has already made connection with the atmospheric port when the first flow path is at a position to start connection with the output port.

3. An oscillating air pressure generator as claimed in claim 1, wherein the switching member is a body of revolution mounted rotatably on the frame and the drive unit urges the switching member to rotate in a predetermined direction;

the switching member defining a first flow path for connecting the positive pressure input port with the output port, a second flow path for connecting the positive pressure input port with the atmospheric port, a third flow path for connecting the negative pressure input port with the output port, and a fourth flow path for connecting the negative input port with the atmospheric port;

wherein when the switching member is at a first rotation angle, the second flow path and the third flow paths are established;

when the switching member is at a second rotation angle, the fourth flow path is established, and when the switching member is at a third rotation angle, the first flow path is established, wherein a difference between the first rotation angle and the second rotation angle is slightly smaller than the difference between the first rotation angle and the third rotation angle.

4. An oscillating air pressure generator as claimed in claim 1, wherein the switching member includes a rotary disc rotatably mounted on the frame and driven to rotate in a predetermined direction by the drive unit, one side of the rotary disc is divided into an inner area and an outer area by a cylinder having a smaller diameter than the rotary disc, so that the output port is provided in one of the inner area and the outer area, and the atmospheric port is provided in the other of the inner area and the outer area, the other side of the rotary disc is divided into two semicircles serving as the positive pressure input port and the negative pressure input port, the rotary disc including diametrically opposed through holes formed in diametrically opposed segments thereof defined by sectors having an angle of 90 degrees or less, one of the through holes extending in the inner area and facing one of the output port and the atmospheric port, and the other of the through holes extending in the outer area and facing the other of the output port and the atmospheric port, and the through hole facing the atmospheric port has a continuous additional opening portion extending in the predetermined direction of rotation of the rotary disc.

5. An oscillating air pressure generator as claimed in claim 1, wherein the switching member includes a rotary disc rotatably mounted on the frame and driven to rotate in a predetermined direction by the drive unit, one side of the rotary disc is divided into an inner area and an outer area by a cylinder having a smaller diameter than the rotary disc, so that the positive pressure input port is provided in one of the inner area and the outer area, and the negative pressure input port is provided in the other of the inner area and the outer area, the other side of the rotary disc is divided into two semicircles serving as the output port and the atmospheric port, the rotary disc including diametrically opposed through holes formed in diametrically opposed segments thereof defined by sectors having an angle of 90 degrees or less, one of the through holes extending in the inner area and facing one of the positive pressure input port and the negative pressure input port, and the other of the through holes extending in the outer area and facing the other of the positive pressure input port and the negative pressure input port, and the through hole facing the negative pressure input port has a continuous additional opening portion extending in the predetermined direction of rotation of the rotary disc.

6. An oscillating air pressure generator as claimed in claim 1, wherein two of the atmospheric ports are provided, one for connection with the positive pressure input port and the other for connection with the negative pressure input port.

7. An oscillating air pressure generator for use in a high-frequency artificial respiration apparatus, said oscillating air pressure generator being connected to an air pressure supplier for simultaneously generating a positive pressure and a negative pressure, said oscillating air pressure generator alternately selecting the positive pressure and the negative pressure to output for generating an oscillating air pressure, said oscillating air pressure generator comprising:

a take-in opening for taking in atmospheric air and an exhaust opening for exhausting an excess positive pressure air, wherein the take-in opening has an inhale silencer based on the frequency characteristic of a noise generated at the take-in opening and the exhaust opening has an exhaust silencer based on the frequency characteristic of a noise generated at the exhaust opening, the inhale silencer including a sound absorbing path forming a flow path for the atmospheric air, and a resonance chamber having a partition to form a closed space adjacent to the atmospheric air flow path, and a single communication hole provided in this partition for communication between the closed space and the atmospheric air flow path.

8. An oscillating air pressure generator as claimed in claim 7, wherein the inhale silencer includes an air filter having a net filter portion of a cylindrical shape for preventing dusts and a cover portion of a cylindrical shape.

9. An oscillating air pressure generator as claimed in claim 7, wherein the inhale silencer has a sound absorbing path having a length substantially larger than its width.

10. An oscillating air pressure generator as claimed in claim 9, wherein the sound absorbing path is formed in a spiral shape.

11. An oscillating air pressure generator for use in a high-frequency artificial respiration apparatus, said oscillating air pressure generator being connected to an air pressure supplier for simultaneously generating a positive pressure and a negative pressure, said oscillating air pressure generator alternately selecting the positive pressure and the negative pressure to output for generating an oscillating air pressure, said oscillating air pressure generator comprising:

a take-in opening for taking in atmospheric air and an exhaust opening for exhausting an excess positive pressure air, wherein the take-in opening has an inhale silencer based on the frequency characteristic of a noise generated at the take-in opening and the exhaust opening has an exhaust silencer based on the frequency characteristic of a noise generated at the exhaust opening, the exhaust silencer including a sound absorbing path surrounded by a sound absorbing material for passing the excess positive pressure air, and an expansion chamber having a partition to define a closed space and an entrance and an exit formed in this partition for the excess positive pressure air.

12. An oscillating air pressure generator as claimed in claim 11, wherein the exhaust silencer includes:

a resonance chamber having a single communication opening provided in the partition for communication between the closed space and the resonance chamber.

13. A high-frequency artificial respiration apparatus comprising: an inhale gas supply unit for supplying oxygen to a patient; an air pressure supplier for simultaneously generating a positive pressure air and a negative pressure air; an oscillating air pressure generator for alternately selecting the positive pressure air and the negative pressure air to output an oscillating air pressure; a diaphragm unit urged by the oscillating air to apply the oscillating air pressure to the oxygen to be supplied to the patient from the inhale gas supply unit;

the oscillating air pressure generator including:

a frame having a positive pressure input port fed by the positive pressure from the air pressure supplier, a negative pressure input port fed by the negative pressure from the air pressure supplier, an atmospheric port open to the atmosphere, and an output port for outputting the oscillating air pressure;

a switching member that selectively switches between a connection state where the positive pressure input port is connected with the output port while the negative pressure input port is connected with the atmospheric port, and a connection state where the positive pressure input port is connected to the atmospheric port while the negative pressure input port is connected to the output port; and a drive unit that successively drives the switching member;

wherein the switching member operates such that the connection between the negative pressure input port and the atmospheric port slightly precedes the connection between the positive pressure input port and the output port.

14. A high-frequency artificial respiration apparatus as claimed in claim 13, wherein the diaphragm unit includes:

a hollow container having an input opening for taking in the oscillating air pressure and an output opening for outputting the oscillating air pressure to the oxygen;

and an elastic diaphragm film to divide the container into an input opening side and an output opening side, and the diaphragm film has a thicker portion at a center portion thereof than at a peripheral portion thereof.

15. A high-frequency artificial respiration apparatus as claimed in claim 14, wherein the hollow container of the diaphragm unit is divided into a first diaphragm section having the input opening and a second diaphragm section having the output opening, each having a match plane when connected with each other, and the diaphragm unit further includes a holding mechanism for maintaining the first and second diaphragm sections together, and two diaphragm films, at least one of the diaphragm films having a thicker portion at a center portion thereof than at a peripheral portion thereof.

16. A high-frequency artificial respiration apparatus as claimed in claim 13, wherein the switching member includes a cylindrical body rotatably mounted on the frame and urged to rotate in a predetermined direction by the drive unit, one end of the switching member faces the positive pressure input port and the other end of the switching member faces the negative pressure input port, and the output port and the atmospheric port are arranged to face the outer circumference of the switching member and to sandwich a rotary shaft of the switching member, the switching member has a first flow path extending from one end toward the outer circumference of the switching member and a second flow path extending from the other end toward the outer circumference of the switching member, one of the second flow path and the atmospheric port being positioned such that when the first flow path is at a position to start connection with the output port, the second flow path is offset by 25 to 50 degrees in the predetermined direction of rotation from a position at which connection with the atmospheric port is started.

17. A high-frequency artificial respiration apparatus as claimed in claim 13, wherein the atmospheric port of the oscillating air pressure generator includes a take-in opening for taking in the atmospheric air and an exhaust opening for exhausting an excessive positive pressure air.

18. A high-frequency artificial respiration apparatus as claimed in claim 17, wherein the take-in opening has an inhale silencer based on the frequency characteristic of the noise caused at the in-take opening, and the exhaust opening has an exhaust silencer based on the frequency characteristic of the noise caused at the exhaust opening.

19. A diaphragm unit for use in a high-frequency artificial respiration apparatus for transmitting an oscillating air pressure generated from an oscillating air pressure generator, to oxygen to be supplied to a patient, the diaphragm unit comprising:

a hollow container having an input opening for introducing an oscillating air pressure from the oscillating air pressure generator and an output opening for outputting the oscillating air pressure to the oxygen to be supplied to the patient, the hollow container being divided into a first diaphragm section having the input opening and a second diaphragm section having the output opening, each having a match plane to face each other when the first diaphragm section and the second diaphragm section are connected, and the diaphragm unit including a holding mechanism for maintaining the first and second diaphragm sections together, and each of the first diaphragm section and the second diaphragm section has a diaphragm film.

20. A diaphragm unit as claimed in claim 19, wherein the diaphragm film to be arranged on the first diaphragm section can be detachably mounted on the match plane of the first diaphragm section.

21. A diaphragm unit as claimed in claim 19, wherein the diaphragm film to be arranged on the second diaphragm section can be detachably mounted on the match plane of the second diaphragm section.

22. A diaphragm unit as claimed in claim 19, wherein each of the diaphragm films has a flange portion at its periphery and each of the match planes has an insert groove for inserting the diaphragm film.

23. A diaphragm unit as claimed in claim 22, wherein at least one of the diaphragm films has a tab.

24. A diaphragm unit as claimed in claim 22, wherein one of the diaphragm films has a protrusion continuously arranged around a periphery thereof to serve as a check valve.

25. A diaphragm unit as claimed in claim 19, wherein the holding mechanism includes: a first holding frame for holding the first diaphragm section; a second holding frame for holding the second diaphragm section; a linkage body for rotatably linking the holding frames; and a connection urging mechanism for urging the first diaphragm section and the second diaphragm section to each other in a direction for bringing the match planes to be in contact with each other;

the linkage body is arranged on one of the holding frames and includes: a rotary shaft arranged in the vicinity of one of the holding frames and capable of moving toward the holding frame; and an engagement member rotatably engaged with the rotary shaft;

the connection urging mechanism includes: a claw member arranged on one of the holding frames so as to be slidable along the matching plate of the diaphragm section held by the holding frame; an engagement member arranged on the other holding frame, where the claw member is to be engaged; and a lever unit to move the claw member by a user;

the claw member has a slanting portion to guide the claw into the engagement member.

* * * * *